(12) United States Patent
Palsson et al.

(10) Patent No.: US 7,734,420 B2
(45) Date of Patent: Jun. 8, 2010

(54) METHODS AND SYSTEMS TO IDENTIFY OPERATIONAL REACTION PATHWAYS

(75) Inventors: Bernhard O. Palsson, La Jolla, CA (US); Markus W. Covert, San Diego, CA (US); Markus Herrgard, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1387 days.

(21) Appl. No.: 10/367,248

(22) Filed: Feb. 14, 2003

(65) Prior Publication Data

US 2004/0072723 A1 Apr. 15, 2004

Related U.S. Application Data

(60) Provisional application No. 60/419,023, filed on Oct. 15, 2002.

(51) Int. Cl.
G06F 19/00 (2006.01)
G06F 17/10 (2006.01)
G06G 7/58 (2006.01)

(52) U.S. Cl. .............................. 702/19; 703/2; 703/11

(58) Field of Classification Search ...................... None
See application file for complete search history.

(56) References Cited

U.S. PATENT DOCUMENTS

| | | | |
|---|---|---|---|
| 5,273,038 A | 12/1993 | Beavin et al. | |
| 5,556,762 A | 9/1996 | Pinilla et al. | |
| 5,639,949 A | 6/1997 | Ligon et al. | |
| 5,689,633 A | 11/1997 | Cotner et al. | |
| 5,914,891 A | 6/1999 | Arkin et al. | |
| 5,930,154 A | 7/1999 | Thalhammer-Reyero | |
| 5,947,899 A | 9/1999 | Scollan et al. | |
| 5,980,096 A | 11/1999 | Thalhammer-Reyero | |
| 6,132,969 A | 10/2000 | Stoughton et al. | |
| 6,165,709 A | 12/2000 | Friend et al. | |
| 6,200,803 B1 | 3/2001 | Roberts | |
| 6,221,597 B1 | 4/2001 | Roberts | |
| 6,302,302 B1 | 10/2001 | Albisetti | |
| 6,326,140 B1 | 12/2001 | Rine et al. | |
| 6,329,139 B1 | 12/2001 | Nova et al. | |
| 6,351,712 B1 | 2/2002 | Stoughton et al. | |
| 6,370,478 B1 | 4/2002 | Stoughton et al. | |
| 6,379,964 B1 | 4/2002 | Del Cardayre | |
| 6,983,227 B1 | 1/2006 | Thalhammer-Reyero | |
| 7,127,379 B2 | 10/2006 | Palsson et al. | 703/2 |
| 2002/0012939 A1 | 1/2002 | Palsson et al. | |
| 2002/0051998 A1 | 5/2002 | Schmidt et al. | |
| 2002/0168654 A1 | 11/2002 | Maranas et al. | |
| 2003/0059792 A1 | 3/2003 | Palsson et al. | |
| 2003/0113761 A1 | 6/2003 | Tan et al. | 435/6 |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2006/0147899 A1 | 7/2006 | Famili et al. | |
| 2007/0111294 A1 | 5/2007 | Burgard et al. | |
| 2008/0176327 A1 | 7/2008 | Palsson et al. | |

FOREIGN PATENT DOCUMENTS

| | | |
|---|---|---|
| WO | WO 92/09300 | 6/1992 |
| WO | WO 00/46405 | 8/2000 |
| WO | WO 01/36658 A2 | 5/2001 |
| WO | WO 01/36658 A3 | 5/2001 |
| WO | WO 01/57775 | 8/2001 |
| WO | WO 02/055995 | 7/2002 |
| WO | WO 02/061115 | 8/2002 |
| WO | WO 03/106998 | 12/2003 |

OTHER PUBLICATIONS

Covert et al. (Journal of Theor. Biol. (2001) vol. 213, pp. 73-88).*
Covert et al., Metabolic Modeling of Microbial Strains *in silico*, *TIBS* Mar. 2001. vol. 26, No. 3, pp. 179-186.
Schilling et al., Assessment of the Metabolic Capabilities of *Heamophilis influenza* Rd through a Genome-scale Pathway Analysis, *J. Theoretical Biology*, 2000, vol. 203, pp. 249-273.
Schilling et al., The underlying pathway structure of biochemical reaction networks, *PNAS*, Apr. 1998, vol. 95, pp. 4193-4198.
Mendes et al., Non-linear optimization of biochemical pathways: Applications to metabolic engineering and parameter estimation, *Bioinformatics*, 1998, vol. 14, No. 10, pp. 869-883.
Edwards et al., In silico predictions of *Escherichia coli* metabolic capabilities are consistent with experimental data., *Nature Biotechnology*, Feb. 2001, vol. 19, pp. 125-130.
Bialy, H., Living on the Edges, *Nature Biotechnology*, Feb. 2001, vol. 19, pp. 111-112.
Varner et al., Mathematical models of metabolic pathways, *Current Opinion in Biotechnology*, 1999, vol. 10, pp. 146-150.
Jamshidi et al., In silico model-driven assessment of the effects of single nucleotide polymorphisms (SMPs) on human red blood cell-metabolism, *Genome Research*, Nov. 2002, vol. 12, No. 11, pp. 1687-1692.
Edwards et al., The *Escherichia coli* MG1655 in silico metabolic genotype: Its definition, characteristics, and capabilities. *PNAS*, May 2000, vol. 97, No. 10, pp. 5528-5533.
Beard et al., "Energy Balance for Analysis of Complex Metabolic Networks", *Biophysical Journal*, 83:79-86 (2002).
Delgado et al., "Identifying Rate-Controlling Enzymes in Metabolic Pathways without Kinetic Parameters", *Biotechnology Progress*, 7:15-20 (1991).

(Continued)

*Primary Examiner*—Lori A Clow
(74) *Attorney, Agent, or Firm*—DLA Piper LLP (US)

(57) ABSTRACT

The present invention provides a method for identifying an operational reaction pathway of a biosystem. The method includes (a) providing a set of systemic reaction pathways through a reaction network representing said biosystem; (b) providing a set of phenomenological reaction pathways of said biosystem, and (c) comparing said set of systemic reaction pathways with said set of phenomenological reaction pathways, wherein a pathway common to said sets is an perational reaction pathway of said biosystem. Also described is a method of refining a biosystem reaction network; a method of reconciling biosystem data sets; a method of determining the effect of a genetic polymorphism on whole cell function; and a method of diagnosing a genetic polymorphism-mediated pathology.

31 Claims, 21 Drawing Sheets

OTHER PUBLICATIONS

Forst C.V., "Network genomics—A novel approach for the analysis of biological systems in the post-genomic era", *Molecular Biology Reports*, 29:265-280 (2002).

Price et al., "Network-based analysis of metabolic regulation in the human red blood cell", *Journal of Theoretical Biology*, 225:185-194 (2003).

Adamowicz, et al., "Nutritional complementation of oxidative glucose metabolism in *Escherichia coli* via pyrroloquinoline quinone-dependent glucose dehydrogenase and the Entner-Doudoroff pathway," *Appl Environ Microbiol*, 57(7):2012-2015 (1991).

Alberty, "Calculation of Biochemical Net Reactions and Pathways by Using Matrix Operations," *Biophys J*, 71(1):507-515 (1996).

Alm, et al., "Genomic-sequence comparison of two unrelated isolates of the human gastric pathogen Helicobacter pylori," *Nature*, 397(6715):176-80 (1999).

Alon, et al., "Broad patterns of gene expression revealed by clustering analysis of tumor and normal colon tissues probed by oligonucleotide arrays,"*Proc Natl Acad Sci U.S.A.*, 96(12):6745-6750 (1999).

Alter, et al., "Singular value decomposition for genome-wide expression data processing and modeling," *Proc Natl Acad Sci U.S.A.*, 97(18):10101-10106 (2000).

Altschul, et al., "Gapped BLAST and PSI-BLAST: A New Generation of Protein Database Search Programs," *Nucl Acids Res*, 25(17):3389-3402 (1997).

Alves, et al., "Systemic properties of ensembles of metabolic networks: application of graphical and statistical methods to simple unbranched pathways," *Bioinformatics*, 16(6):534-547(2000).

Andre, "An overview of membrane transport proteins in *Saccharomyces cerevisiae,*" *Yeast*, 11(16):1575-1611 (1995).

Anonymous, "The yeast genome directory" *Nature*, 387(6632 Suppl):5 (1997).

Appel, et al., "A new generation of information retrieval tools for biologists: the example of the ExPASy WWW server," *Trends Biochem Sci*, 19(6):258-260 (1994).

Arigoni, et al., "A Genome-Based Approach for the Identification of Essential Bacterial Genes," *Nature Biotechnology*, 16(9):851-856 (1998).

Attanoos, et al., "Ileostomy polyps, adenomas, and adenocarcinomas," *Gut*, 37(6):840-844 (1995).

Baba, et al., "Construction of *Escherichia coli* K-12 in-frame, single-gene knockout mutants: the Keio collection," *Mol Syst Biol*, 2:2006-2008 (2006).

Bailey, "Complex Biology With No Parameters," *Nat Biotechnol*, 19(6):503-504 (2001).

Bailey, TL and Elkan, C, "Fitting a mixture model by expectation maximization to discover motifs in biopolymers," *Proc Int Conf Intell Syst Mol Biol*, 2:28-36 (1994).

Bailey, TL and Gribskov, M, "Combining evidence using p-values: application to sequence homology searches," *Bioinformatics*, 14(1):48-54 (1998).

Bairoch, A, and Apweiler, R, "The SWISS-PROT Protein Sequence database and its supplement TrEMBL in 2000," *Nucleic Acids Res*, 28(1):45-48 (2000).

Ball, et al., "Integrating functional genomic information into the *Saccharomyces* genome database," *Nucleic Acids Res*, 28(1):77-80 (2000).

Baltz, et al., "DNA Sequence Sampling of the *Streptococcus* Pneumonia Genome to Identify Novel Targets for Antibiotic Development," *Microbial Drug Resistance*, 4(1):1-9 (1998).

Ban, et al., "Thymine and uracil catabolism in *Escherichia coli*," *J Gen Microbiol*, 73(2):267-272 (1972).

Bansal, "Integrating co-regulated gene-groups and pair-wise genome comparisons to automate reconstruction of microbial pathways,"*Bioinformatics and Bioengineering Conference*, 209-216 (2001).

Bard, et al., "Sterol mutants of *Saccharomyces cerevisiae*: chromatographic analyses," *Lipids*, 12(8):645-654 (1977).

Baxevanis, "The Molecular Biology Database Collection: 2002 update," *Nucleic Acids Res*, 30:1-12 (2002).

Beckers, et al., "Large-Scale Mutational Analysis for the Annotation of the Mouse Genome," *Curr Opin Chem Biol*, 6(1)17-23 (2002).

Bell, et al., "Composition and functional analysis of the *Saccharomyces cerevisiae* trehalose synthase complex," *J Biol Chem.*, 273(50):33311-33319 (1998).

Benjamini and Hochberg, "Controlling the false discovery rate: a practical and powerful approach to multiple testing," *J Roy Stat Soc Ser B (Methodological)* , 57:289-300 (1995).

Benson, et al., "GenBank," *Nucleic Acids Res*, 28(1):15-18 (2000).

Berry, "Improving production of aromatic compounds in *Escherichia coli* by metabolic engineering," *Trends Biotechnol*, 14(7):250-256 (1996).

Bianchi, P, and Zanella, A, *Blood Cells, Molecules, and Diseases*, 15:47-53 (2000).

Biaudet, et al., "Micado—A network-oriented database for microbial genomes," *Comput Appl Biosci*, 13(4):431-438 (1997).

Birkholz, "Fumarate reductase of Helicobacter pylori—an immunogenic protein," *J Med Microbiol*, 41(1):56-62 (1994).

Birner, et al., "Roles of phosphatidylethanolamine and of its several biosynthetic pathways in *Saccharomyces cerevisiae,*" *Mol Biol Cell*, 12(4):997-1007 (2001).

Blackstock, WP and Weir, MP, "Proteomics: quantitative and physical mapping of cellular proteins," *Trends Biotechnol*, 17(3):121-127 (1999).

Blattner, et al., "The Complete Genome Sequence of *Escherichia coli* K-12," *Science*, 277(5331):1453-1474 (1997).

BMES/EMBS Conference, Proceedings of the First Joint, vol. 2, p. 1217 (1999).

Bochner, "New technologies to assess genotype-phenotype relationships," *Nat Rev Genet*, 4(4):309-314 (2003).

Boles, E, et al., "Identification and characterization of MAE 1 ,the *Saccharomyces cerevisiae* structural gene encoding mitochondrial malic enzyme," *J Bacteriol.*, 180(11):2875-2882 (1998).

Boles, et al "A family of hexosephosphate mutases in *Saccharomyces cerevisia*," *Eur J Biochem*, 220(1):83-96 (1994).

Boles, et al., "Characterization of a glucose-repressed pyruvate kinase (Pyk2p) in *Saccharomyces cerevisiae* that is catalytically insensitive to fructose-1,6-bisphosphate," *J Bacteriol*, 179(9):2987-2993 (1997).

Bonarius, et al., "Flux Analysis of Underdetermined Metabolic Networks: The Quest for the Missing Constraints," *Trends Biotechnol*, 15(8):308-314 (1997).

Bonarius, et al., "Metabolic flux analysis of hybridoma cells in different culture media using mass balances," *Biotechnol Bioeng*, 50(3):299-318 (1996).

Bono, et al., "Reconstruction of amino acid biosynthesis pathways from the complete genome sequence," *Genome Research*, 8(3):203-210 (1998).

Bottomley, et al., "Cloning, sequencing, expression, purification and preliminary characterization of a type II dehydroquinase from *Helicobacter pylori*," *Biochem. J*, 319(Pt 2):559-565 (1996).

Bourot, S and Karst, F, "Isolation and characterization of the *Saccharomyces cerevisiae* SUT1 gene involved in sterol uptake," *Gene*, 165(1):97-102 (1995).

Burgard, AP and Maranas, CD, "Probing the Performance Limits of the *Escherichia coli* Metabolic Network Subject to Gene Additions or Deletions," *Biotechnol Bioeng*, 74(5):364-375 (2001).

Burgard, AP and Maranas, CD, "Review of the Enzymes and Metabolic Pathways (EMP) Database," *Metab Eng*, 3(3):193-194(2) (2001).

Burgard, et al., "Minimal reaction sets for *Escherichia coli* metabolism under different growth requirements and uptake environments," *Biotechnol Prog*, 17(5):791-797 (2001).

Burgard, et al., "Optknock: a bilevel programming framework for identifying gene knockout strategies for microbial strain optimization," *Biotechnol Bioeng*, 84(6):647-657 (2003).

Burns, "Acetyl-CoA carboxylase activity in Helicobacter pylori and the requirement of increased CO2 for growth," *Microbiology*, 141(Pt 12):3113-3118 (1995).

Chadha, et al., "Hybrid process for ethanol production from rice straw," *Acta Microbiol Immunol Hung*, 42(1):53-59 (1995).

Chadha, et al., "Simultaneous saccharification and fermentation of rice straw into ethanol," *Acta Microbiol Immunol Hung.*, 42(1):71-75 (1995).

Chalker, et al., "Systematic identification of selective essential genes in Helicobacter pylori by genome prioritization and allelic replacement mutagenesis," *J Bacteriol*, 183(4):1259-1268 (2001).

Chen, et al., "Characterization of the respiratory chain of Helicobacter pylori," *FEMS Immunol Med Microbiol*, 24(2):169-174 (1999).

Cherry, et al., "SGD: Saccharomyces Genome Database," *Nucleic Acids Res*, 26(1):73-79 (1998).

Christensen, B and Nielsen, J, "Metabolic network analysis. A powerful tool in metabolic engineering," *Advances in Biochemical Engineering/Biotechnology*, 66:209-231 (2000).

Ciriacy, M and Breitenbach, I, "Physiological effects of seven different blocks in glycolysis in Saccharomyces cerevisiae," *J Bacteriol*, 139(1):152-160 (1979).

Clarke, "Complete set of steady states for the general stoichiometric dynamical system," *J Chem Phys*, 75(10):4970-4979 (1981).

Clarke, "Stoichiometric network analysis," *Cell Biophys*, 12:237-253 (1988).

Clarke, *Stability of Complex Reaction Networks. Advances in Chemical Physics*, 43:1-125 (1980).

Clifton, D and Fraenkel, DG, "Mutant studies of yeast phosphofructokinase.," *Biochemistry*, 21(8):1935-1942 (1982).

Clifton, et al., "Glycolysis mutants in Saccharomyces cerevisiae.," *Genetics*, 88(1):1-11 (1978).

Compan, I and Touati, D, et al., "Anaerobic activation of arcA transcription in Escherichia coli: roles of Fnr and ArcA," *Mol Microbiol*, 11(5):955-964 (1994).

Costanzo, et al., "YPD, PombePD and WormPD: model organism volumes of the BioKnowledge library, an integrated resource for protein information," *Nucleic Acids Res*, 29(1):75-9 (2001).

Cotter, et al., "Aerobic regulation of cytochrome d oxidase (cydAB) operon expression in Escherichia coli: roles of Fnr and ArcA in repression and activation," *Mol Microbiol*, 25(3):605-615 (1997).

Cover, TL and Blaser, MJ, "Helicobacter pylori infection, a paradigm for chronic mucosal inflammation: pathogenesis and implications for eradication and prevention," *Adv Intern Med*, 41:85-117 (1996).

Covert and Palsson, "Constraints-based models: regulation of gene expression reduces the steady-state solution space" *J Theor Biol*, 216 (2003).

Covert and Palsson, "Transcriptional regulation in constraints-based metabolic models of Escherichia coli," *J Biol Chem*, 277(31):28058-28064 (2002).

Cupp, JR and McAlister-Henn, L, "Cloning and Characterization of the gene encoding the IDH1 subunit of NAD(+)-dependent isocitrate dehydrogenase from Saccharomyces cerevisiae," *J Biol Chem*, 267(23):16417-16423 (1992).

D'Haeseleer, et al., "Genetic network inference: from co-expression clustering to reverse engineering," *Bioinformatics*, 16(8):707-726 (2000).

Danchin, "Comparison Between the Escherichia coli and Bacillus subtilis Genomes Suggests That a Major Function of Polynucleotide Phosphorylase is to Synthesize CDP," *DNA Research*, 4(1):9-18 (1997).

Dandekar, et al., "Pathway Alignment: Application to the Comparative Analysis of Glycolytic Enzymes," *Biochem J*, 343(Pt 1):115-124 (1999).

Dantigny, et al., "Transition rate kinetics from ethanol oxidation to glucose utilisation within a structured model of baker's yeast," *Appl Microbiol Biotechnol*, 36:352-357 (1991).

Datsenko, KA and Wanner, BL, "One-step inactivation of chromosomal genes in Escherichia coli K-12 using PCR products," *Proc Natl Acad Sci U.S.A.*, 97(12):6640-6645 (2000).

Daum, et al., "Biochemistry, cell biology and molecular biology of lipids of Saccharomyces cerevisiae," *Yeast*, 14(16):1471-1510 (1998).

Daum, et al., "Systematic analysis of yeast strains with possible defects in lipid metabolism," *Yeast*, 15(7):601-614 (1999).

Dauner, et al., "Bacillus subtilis Metabolism and Energetics in Carbon-Limited and Excess-Carbon Chemostat Culture," *J Bacteriol*, 183(24):7308-7317 (2001).

Dauner, et al., "Metabolic Flux Analysis with a Comprehensive Isotopomer Model in Bacillus subtilis," *Biotechnol Bioeng*, 76(2):144-156 (2001).

Dauner, M and Sauer, U, "Stoichiometric Growth Model for Riboflavin-Producing Bacillus subtilis," *Biotechnol Bioeng*, 76(1):132-143 (2001).

de Jong, H., "Modeling and simulation of genetic regulatory systems: a literature review," *J Comput Biol*, 9(1):67-103 (2002).

De Reuse, et al., "The Helicobacter pylori ureC gene codes for a phosphoglucosamine mutase," *J Bacteriol*, 179(11):3488-3493 (1997).

Demain, et al., "Cellulase, *clostridia*, and ethanol," *Microbiol Mol Biol Rev*, 69(1):124-154 (2005).

Department of Energy, *Breaking the Biological Barriers to Cellulosic Ethanol* (2006).

DeRisi et al.,"Exploring the Metabolic and Genetic Control of Gene Expression on a Genomic Scale," *Science*, 278(5338):680-686 (1997).

Devine, KM, "The Bacillus subtilis Genome Project: Aims and Progress," *Trends Biotechnol*, 13(6):210-216 (1995).

Dickson, "Sphingolipid functions in Saccharomyces cerevisiae: comparison to mammals," *Annu Rev Biochem*, 67:27-48 (1998).

Dickson, et al., "Serine palmitoyltransferase," *Methods Enzymol*, 311:3-9 (2000).

DiRusso, CC and Black, PN, "Long-chain fatty acid transport in bacteria and yeast. Paradigms for defining the mechanism underlying this protein-mediated process," *Mol Cell Biochem*, 192(1-2):41-52 (1999).

Dooley, et al., "An all D-amino acid opiod peptide with central analgesic activity from a combinatorial library," *Science*, 266(5193):2019-2022 (1994).

Edwards, et al., "Characterizing the Metabolic Phenotype: A Phenotype Phase Plane Analysis," *Biotech Bioeng*, 77(1):27-36 (2002).

Edwards, JS and Palsson, BO, "How Will Bioinformatics Influence Metabolic Engineering," *Biotechnol Bioeng*, 58(2-3):162-169 (1998).

Edwards, JS and Palsson, BO, "Robustness analysis of the Escherichia coli metabolic network," *Biotechnol Prog*, 16(6):927-939 (2000).

Edwards, JS and Palsson, BO, "Systems properties of the Haemophilus influenzae Rd metabolic genotype," *J Biol Chem*, 274(25):17410-17416 (1999).

Edwards, JS, and Palsson, BO, "Metabolic flux balance analysis and the *in silico* analysis of Escherichia colia K-12 gene deletions," *BMC Bioinformatics*, 1:1-10 (2000).

Edwards, et al., "Genomically Based Comparative Flux Balance Analysis of Escherichia coli and Haemophilus Influenza," Abstract of Papers, *American Chemical Society*, 213(1-3):BIOT 50. San Francisco (13-17, 1997).

Eisen, et al., "Cluster analysis and display of genome-wide expression patterns," *Proc Natl Acad Sci U.S.A.*, 95:14863-14868 (1998).

Eisenberg, et al., "Protein Function in the Post-Genomic Era," *Nature*, 405(6788):823-826 (2000).

Ermolaeva, et al., "Prediction of Operons in Microbial Genomes," *Nucl Acids. Research*, 29(5):1216-1221 (2001).

Everett, et al., "Pendred Syndrome is Caused by Mutations in a Putative Sulphate Transporter Gene (PDS)," *Nat Genet*, 17:411-422 (1997).

Fell, DA and Small, JR, "Fat Synthesis in Adipose Tissue. An Examination of Stoichiometric Constraints," *Biochem J*, 238(3):781-786 (1986).

Fiehn, "Metabolomics—the link between genotypes and phenotypes," *Plant Mol Biol*, 48(1-2):155-171 (2002).

Finel, "Does NADH play a central role in energy metabolism in Helicobacter pylori?," *Trends Biochem Sci*, 23(11):412-413 (1998).

Fiorelli, et al., "Chronic non-spherocytic haemolytic disorders associated with glucose-6-phosphate dehydrogenase variants," *Bailliere's Clinical Haematology*, 13:39-55 (2000).

Fleischmann, "Whole-genome random sequencing and assembly of Haemophilus influenzae Rd," *Science*, 269(5223):496-512 (1995).

Flikweert, et al., "Pyruvate decarboxylase: an indispensable enzyme for growth of Saccharomyces cerevisiae on glucose.," *Yeast*, 12(3):247-257 (1996).

Forster, et al., "Large-scale evaluation of in silico gene deletions in *Saccharomyces cerevisiae*," *Omics*, 7(2)193-202 (2003).

Fraenkel, "The accumulation of glucose 6-phosphate from glucose and its effect in an *Escherichia coli* mutant lacking phosphoglucose isomerase and glucose 6-phosphate dehydrogenase," *J Biol Chem*, 243(24):6451-6457 (1968).

Fraser, et al., "Microbial genome sequencing," *Nature*, 406:799-803 (2000).

Fromont-Racine, et al., "Toward a functional analysis of the yeast genome through exhaustive two-hybrid screens," *Nat Genet*, 16(3):277-282 (1997).

Fukuchi, et al., "Isolation, overexpression and disruption of a *Saccharomyces cerevisiae* YNK gene encoding nucleoside diphosphate kinase," *Genes*, 129(1):141-146 (1993).

Gaasterland, T. and Selkov, E., "Reconstruction of Metabolic Networks Using Incomplete Information," *Proc Int Conf Intell Syst Mol Biol*, 3:127-135 (1995).

Galperin, MY and Brenner, SE, "Using Metabolic Pathway Databases for Functional Annotation," *Trends Genet*, 14(8):332-333 (1998).

Gancedo, C and Delgado, MA, "Isolation and characterization of a mutant from *Saccharomyces cerevisiae* lacking fructose 1,6-bisphosphatase," *Eur J Biochem*, 139:651-655 (1984).

Gangloff, et al., "Molecular cloning of the yeast mitochondrial aconitase gene (ACO1) and evidence of a synergistic regulation of expression by glucose plus glutamate.," *Mol Cell Biol*, 10(7):3551-3561 (1990).

Ge, et al., "Cloning and functional characterization of Helicobacter pylori fumarate reductase operon comprising three structural genes coding for subunits C, A and B," *Gene*, 204(1-2):227-234 (1997).

Glasner, et al., "ASAP, a systematic annotation package for community analysis of genomes," *Nucleic Acids Res*, 31(1):147-151 (2003).

Goffeau, A, "Four years of post-genomic life with 6000 yeast genes," *FEBS Lett*, 480(1):37-41 (2000).

Goryanin, et al., "Mathematical simulation and analysis of cellular metabolism and regulation," *Bioinformatics*, 15(9):749-758 (1999).

Goto, et al., "LIGAND database for enzymes, compounds and reactions," *Nucleic Acids Res*, 27(1):377-379 (1999).

Goto, et al., "LIGAND: chemical database for enzyme reactions," *Bioinformatics*, 14(7):591-599 (1998).

Grewal, et al., "Computer Modelling of the Interaction Between Human Choriogonadotropin and Its Receptor," *Protein Engineering*, 7(2):205-211 (1994).

Griffin, et al., "Complementary profiling of gene expression at the transcriptome and proteome levels in *Saccharomyces cerevisiae*," *Mol Cell Proteomics*, 1:323-333 (2002).

Grundy, et al., "Regulation of the *Bacillus subtilis* acetate kinase gene by CcpA." *J Bacteriol*, 175(22):7348-7355 (1993).

Guelzim, et al., "Topological and causal structure of the yeast transcriptional regulatory network," *Nat Genet*, 31(1):60-63 (2002).

Guetsova, et al., "The isolation and characterization of *Saccharomyces cerevisiae* mutants that constitutively express purine biosynthetic genes," *Genetics*, 147(2):383-397 (1997).

Halvorson, et al., *American Society for Microbiology*, Washington, D.C., pp. 212-224 (1972).

Hardison, et al., "Globin Gene Server: A Prototype E-Mail Database Server Featuring Extensive Multiple Alignments and Data Compilation for Electronic Genetic Analysis," *Genomics*, 21(2):344-353 (1994).

Hartig, et al., "Differentially regulated malate synthase genes participate in carbon and nitrogen metabolism of *S. cerevisiae*.," *Nucleic Acids Res*, 20(21):5677-5686 (1992).

Hasty, et al., "Computational Studies of Gene Regulatory Networks: In Numero Molecular Biology," *Nat Rev Genet*, 2(4):268-279 (2001).

Hata, et al., "Characterization of a *Saccharomyces cerevisiae* mutant, N22, defective in ergosterol synthesis and preparation of [28-14C]ergosta-5,7-dien-3 beta-ol with the mutant," *J Biochem*, 94(2):501-510 (1983).

Hatzimanikatis, et al., "Analysis and Design of Metabolic Reaction Networks Via Mixed-Interger linear Optimization," *AIChE Journal*, 42(5):1277-1292 (1996).

Hazell, et al., "How Helicobacter pylori works: an overview of the metabolism of Helicobacter pylori," Helicobacter, 2(1):1-12 (1997).

Heijnen, et al., "Application of balancing methods in modeling the penicillin fermentation," *Microbiol Biochem*, 21:1-48 (1979).

Heinisch, et al., "Investigation of two yeast genes encoding putative isoenzymes of phosphoglycerate mutase.," *Yeast*, 14(3):203-213 (1998).

Heinrich, et al., "Metabolic regulation and mathematical models," *Prog Biophys Mol Biol*, 32(1):1-82 (1977).

Heinrich, et al., "Stoichiometric Analysis," *The Regulation of Cellular Systems*, xix:75-111 and 372, Chapman & Hall, New York (1996).

Henriksen, et al., "Growth energetics and metabolism fluxes in continuous cultures of *Penicillium chrysogenum*," *J of Biotechnol*, 45(2):149-164 (1996).

Heyer, et al., "Exploring expression data: identification and analysis of coexpressed genes," *Genome Res*, 9(11):1106-1115 (1999).

Holter, et al., "Dynamic modeling of gene expression data," *Proc Natl Acad Sci U.S.A.*, 98(4):1693-1698 (2001).

Holter, et al., "Fundamental patterns underlying gene expression profiles: simplicity from complexity," *Proc Natl Acad Sci U.S.A.*, 97:8409-9414 (2000).

Houghten, "Generation and use of synthetic peptide combinatorial libraries for basic research and drug discovery," *Nature*, 354(6348):84-86 (1991).

Hughes, et al., "Functional discovery via a compendium of expression profiles," *Cell*, 102(1):109-126 (2000).

Hughes, et al., "Helicobacter pylori porCDAB and oorDABC genes encode distinct pyruvate: flavodoxin and 2-oxoglutarate:acceptor oxidoreductases which mediate electron transport to NADP," *J Bacteriol*, 180(5):1119-1128 (1998).

Ideker, et al., "Integrated Genomic and Proteomic Analyses of a Systematically Perturbed Metabolic Network," *Science*, 292(5518):929-934 (2001).

Ince, JE and Knowles, CJ, "Ethylene formation by cell-free extracts of *Escherichia coli*," *Arch Microbiol*, 146(2):151-158 (1986).

Ishii, et al., "DBTBS: A database of *Bacillus subtilis* promoters and transcription factors," *Nucleic Acids Res*, 29(1):278-280 (2001).

Iyer, et al., "Genomic binding sites of the yeast cell-cycle transcription factors SBF and MBF," *Nature*, 409(6819):533-538 (2001).

Jamshidi, et al., "Dynamic simulation of the human red blood cell metabolic network," *Bioinformatics*, 17(3):286-287 (2001).

Jamshidi, et al., "In silico model-driven assessment of the effects of single nucleotide polymorphins (SNPs) on human red blood cell-metabolism," *Genome Research*, 12(11):1687-1692 (2002).

Jenkins, LS and Nunn, WD, "Genetic and molecular characterization of the genes involved in short-chain fatty acid degradation in *Escherichia coli*: the ato system," *J Bacteriol*, 169(1):42-52 (1987).

Jenssen, et al., "A Literature Network of Human Genes for High-Throughput Analysis of Gene Expression," *Nat Genet*, 28(1):21-28 (2001).

Johnson, RA and Wichern, DW, *Applied Multivariate Statistical Analysis*, 5th Ed., Prentice Hall, New Jersey (2002).

Jorgensen, et al., "Metabolic flux distributions in *Penicillium chrysogenum* during fed-batch cultivations." *Biotechnol Bioeng*, 46(2):117-131 (1995).

Joshi, A and Palsson, BO, "Metabolic dynamics in the human red cell. Part I—A comprehensive kinetic model," *J Theor Biol*, 141(4):515-528 (1989).

Juty, et al., "Simultaneous Modeling of Metabolic, Genetic, and Product-Interaction Networks," *Briefings in Bioinformatics*, 2(3):223-232 (2001).

Kanehisa, M and Goto, S, "Kyoto Encyclopedia of Genes and Genomes database (KEGG)," *Nucleic Acids Res*, 28(1):27-30 (2000).

Karp, "An ontology for biological function based on molecular interactions," *Bioinformatics*, 16(3):269-285 (2000).

Karp, "Metabolic Databases," *Trends Biochem Sci*, 23(3):114-116 (1998).

Karp, et al., "Eco Cyc: encyclopedia of *Escherichia coli* genes and metabolism," *Nucleic Acids Res*, 27(1):55-58 (1999).

Karp, et al., "EcoCyc: Encyclopedia of *Escherichia coli* Genes and Metabolism," *Nucleic Acids Research*, 25(1):43-50 (1997).

Karp, et al., "HinCyc: A knowledge base of the complete genome and metabolic pathways of H. influenzae," *Proc Int Conf Intell Syst Mol Biol*, 4:116-124 (1996).

Karp, et al., "Integrated pathway-genome databases and their role in drug discovery," *Trends Biotechnol*, 17(7):275-281 (1999).

Karp, et al., "The EcoCyc and MetaCyc databases," *Nucleic Acids Resarch*, 28(1):56-59(2000).

Kather, et al., "Another unusual type of citric acid cycle enzyme in Helicobacter pylori: the malate:quinone oxidoreductase," *J Bacteriol*, 182(11):3204-3209 (2000).

Keating, et al., "An ethanologenic yeast exhibiting unusual metabolism in the fermentation of lignocellulosic hexose sugars," *J Ind Microbiol Biotechnol*, 31(5):235-244.

Kelly, "The physiology and metabolism of the human gastric pathogen Helicobacter pylori," *Adv Microb Physiol*, 40:137-189 (1998).

Kim, et al., "*Saccharomyces cerevisiae* contains two functional citrate synthase genes.," *Mol Cell Biol*, 6(6):1936-1942 (1986).

Kirkman, et al., "Red cell NADP+and NADPH in glucose-6-phosphate dehydrogenase deficiency," *Journal of Clinical Investigation*, 55(4):875-878 (1975).

Kremling, et al., "The organization of metabolic reaction networks. III. Application for diauxic growth on glucose and lactose," *Metab Eng*, 3(4):362-379 (2001).

Kunst, et al., "The Complete Genome Sequence of the Gram-positive Bacterium *Bacillus subtilus*," *Nature*, 390(6557):249-256 (1997).

Lacroute, "Regulation of pyrimidine biosynthesis in *Saccharomyces cerevisiae*" *J Bacteriol*, 95(3):824-832 51968).

Latif, F and Rajoka, MI, "Production of ethanol and xylitol from corn cobs by yeasts," *Bioresour Technol*, 77(1):57-63 (2001).

Lendenmann, U and Egli, T, "Is *Escherichia coli* growing in glucose-limited chemostat culture able to utilize other sugars without lag?," *Microbiology*, 141(Pt 1):71-78 (1995).

Leyva-Vasquez, MA and Setlow, P, "Cloning and nucleotide sequences of the genes encoding triose phosphate isomerase, phosphoglycerate mutase, and enolase from Bacillus subtilis," *J Bacteriol*, 176(13):3903-3910 (1994).

Li, C and Wong, WH, "Model-based analysis of oligonucleotide arrays: expression index computation and outlier detection," *Proc Natl Acad Sci U.S.A.*, 98(1):31-36 (2001).

Liao, et al., "Pathway Analysis, Engineering, and Physiological Considerations for Redirecting Central Metabolism," *Biotechnol Bioeng*, 52(1):129-140 (1996).

Liao, JC and Oh, MK, "Toward predicting metabolic fluxes in metabolically engineered strains," *Metab Eng*,1(3):214-223 (1999).

Link, et al., "Methods for generating precise deletions and insertions in the genome of wild-type *Escherichia coli*: Application to open reading frame characterization," *J Bacteriol*, 179(20):6228-6237 (1997).

Loftus, et al., "Isolation, characterization, and disruption of the yeast gene encoding cytosolic NADP-specific isocitrate dehydrogenase," *Biochemistry*, 33(32):9661-9667.

Lopez, et al., "The yeast inositol monophosphatase is a lithium- and sodium-sensitive enzyme encoded by a non-essential gene pair," *Mol Microbiol*, 31(4):1255-1264 (1999).

Mahadevan, R and Schilling, CH, "The effects of alternate optimal solutions in constraint-based genome-scale metabolic models," *Metab Eng*, 5(4):264-276 (2003).

Maier, et al., "Hydrogen uptake hydrogenase in Helicobacter pylori," *FEMS Microbiol Lett*, 141(1):71-76 (1996).

Majewski, RA and Domach, MM, "Simple Constrained-Optimization View of Acete Overflow in *E. Coli*," *Biotechnol Bioeng*, 35(7):732-738 (1990).

Marcelli, et al., "The respiratory chain of Helicobacter pylori: identification of cytochromes and the effects of oxygen on cytochrome and menaquinone levels," *FEMS Microbiol Lett*, 138(1):59-64 (1996).

Marshall, B.J and Warren, J.R., "Unidentified curved *bacilli* in the stomach of patients with gastritis and peptic ulceration," *Lancet*, 1(8390):1311-1315 (1984).

McAdams, HH and Arkin, A, "Simulation of Prokaryotic Genetic Circuits," *Annual Review of Biophysics and Biomolecular Structure*, 27:199-224 (1998).

McAdams, HH and Shapiro, L, "Circuit simulation of genetic networks." *Science*, 269(5224):650-656 (1995).

McAlister-Henn, L and Thompson, LM, "Isolation and expression of the gene encoding yeast mitochondrial malate dehydrogenase.," *J Bacteriol*, 169(11):5157-5166 (1987).

McGee, D.J., "Helicobacter pylori rocF is required for arginase activity and acid protection in vitro but is not essential for colonization of mice or for urease activity," *J Bacteriol*, 165(1):65-76 (1998).

Meldrum, "Automation for genomics, part one: preparation for sequencing," *Genome Res*, 10(8):1081-1092 (2000).

Mendz, et al., "Characterisation of glucose transport in Helicobacter pylori," *Biochim Biophys Acta*, 1244(2-3):269-276 (1995).

Mendz, et al., "Characterization of fumarate transport in Helicobacter pylori," *J Membr Biol*, 165(1):65-76 (1998).

Mendz, et al., "De novo synthesis of pyrimidine nucleotides by Helicobacter pylori," *J Appl Bacteriol*, 77(1):1-8 (1994).

Mendz, et al., "Fumarate reductase: a target for therapeutic intervention against Helicobacter pylori," *Arch Biochem Biophys*, 321(1):153-159 (1995).

Mendz, et al., "Glucose utilization and lactate production by Helicobacter pylori," *J Gen Microbiol*, 139(12):3023-3028 (1993).

Mendz, et al., "In situ characterization of Helicobacter pylori arginase," *Biochim Biophys Acta*, 1388(2):465-477 (1998).

Mendz, et al,."Purine metabolism and the microaerophily of Helicobacter pylori," *Arch Microbiol*, 168(6):448-456 (1997).

Mendz, et al., "The Entner-Doudoroff pathway in Helicobacter pylori," *Arch Biochem Biophys*, 312(2):349-356 (1994).

Mendz, GL and Hazell SL, "Aminoacid utilization by Helicobacter pylori," *Int J Biochem Cell Biol*, 27(10):1085-1093 (1995).

Mendz, GL and Hazell, SL, "Fumarate catabolism in Helicobacter pylori," *Biochem Mol Biol Int*, 31(2):325-332 (1993).

Mendz, GL and Hazell, SL, "Glucose phosphorylation in Helicobacter pylori," *Arch Biochem Biophys*, 300(1):522-525 (1993).

Mendz, GL, et al., "Pyruvate metabolism in Helicobacter pylori," *Arch Microbiol*, 162(3):187-192 (1994).

Mendz, GL, et al., "Salvage synthesis of purine nucleotides by Helicobacter pylori," J Appl Bacteriol, 77(6):674-681 (1994).

Mewes, et al., "MIPS: A database for genomes and protein sequences," *Nucleic Acids Research*, 30(1):31-34 (2002).

Mitchell, "The GLN1 locus of *Saccharomyces cerevisiae* encodes glutamine synthetase," *Genetics*, 111(2):243-258 (1985).

Moszer, "The Complete Genome of *Bacillus subtilis*: From Sequence Annotation to Data Management and Analysis," *FEBS Lett*, 430(1-2):28-36 (1998).

Moszer, et al., "SubtiList: the reference database for the *Bacillus subtilis* genome," *Nucleic Acids Res*, 30(1):62-65 (2002).

Mulquiney, PJ and Kuchel, PW, "Model of 2,3-bisphosphoglycerate metabolism in the human erythrocyte based on detailed enzyme kinetic equations: computer simulation and metabolic control analysis," *Biochem J*, 342(Pt 3):597-604 (1999).

Murray, M and Greenberg, ML, "Expression of yeast INM1 encoding inositol monophosphatase is regulated by inositol, carbon source and growth stage and is decreased by lithium and valproate," *Mol Microbiol*, 36(3):651-661 (2000).

Nedenskov, "Nutritional requirements for growth of Helicobacter pylori," *Appl Environ Microbiol*, 60(9):3450-3453 (1994).

Nissen, et al., "Expression of a cytoplasmic transhydrogenase in *Saccharomyces cerevisiae* results information of 2-oxoglutarate due to depletion of the NADPH pool," *Yeast*, 18(1):19-32 (2001).

Nissen, et al., "Flux distributions in anaerobic, glucose-limited continuous cultures of *Saccharomyces cerevisiae*," *Microbiology*, 143(Pt 1):203-218 (1997).

Ogasawara, "Systematic function analysis of *Bacillus subtilis* genes," *Res Microbiol*, 151(2):129-134 (2000).

Ogata, et al., "KEGG: Kyoto Encyclopedia of Genes and Genomes," *Nucleic Acids Res*, 27(1):29-34 (1999).

Oh, MK and Liao, JC, "Gene expression profiling by DNA microarrays and metabolic fluxes in *Escherichia coli*," *Biotech Prog*, 16:278-286 (2000).

Olsson, et al., "Separate and simultaneous enzymatic hydrolysis and fermentation of wheat hemicellulose with recombinant xylose utilizing *Saccharomyces cerevisiae*," *Appl Biochem Biotechnol*, 129-132:117-129 (2006).

Otto, et al., "A mathematical model for the influence of fructose 6-phosphate, ATP, potassium, ammonium and magnesium on the phosphofructokinase from rat erythrocytes," *Eur J Biochem*, 49(1):169-178 (1974).

Ouzounis, CA and Karp, PD, "Global Properties of the Metabolic Map of *Escherichia coli*," *Genome Res*, 10(4):568-576 (2000).

Overbeek, et al., "WIT: Integrated System for High-Throughput Genome Sequence Analysis and Metabolic Reconstruction"*Nucleic Acids Res*, 28(1):123-125 (2000).

Overkamp, et al., "In vivo analysis of the mechanisms for oxidation of cytosolic NADH by *Saccharomyces cerevisiae* mitochondria," *J Bacteriol*, 182(10):2823-2830 (2000).

Ozcan, S., Freidel, K., Leuker, A. & Ciriacy, M., "Glucose uptake and catabolite repression in dominant HTR1 mutants of *Saccharomyces cerevisiae*," *J Bacteriol*, 175(17):5520-5528 (1993).

Pallotta, et al., "*Saccharomyces cerevisiae* mitochondria can synthesise FMN and FAD from externally added riboflavin and export them to the extramitochondrial phase," *FEBS Lett*, 428(3):245-249 (1998).

Palmieri, et al., "Identification and functions of new transporters in yeast mitochondria," *Biochim Biophys Acta*, 1459(2-3):363-369 (2000).

Palmieri, et al., "Identification of the yeast ACR1 gene product as a succinate-fumarate transporter essential for growth on ethanol or acetate," *FEBS Lett*, 417(1):114-118 (1997).

Palmieri, et al., "Identification of the yeast mitochondrial transporter for oxaloacetate and sulfate," *J Biol Chem*, 274(32):22184-22190 (1999).

Palmieri, et al., "Yeast mitochondrial carriers: bacterial expression, biochemical identification and metabolic significance," *J Bioenerg Biomembr*, 32(1):67-77 (2000).

Palsson, "The Challenges of in Silico Biology," *Nat Biotechnol*, 18(10:1147-1150 (2000).

Palsson, "What Lies Beyond Bioinformatics," *Nat Biotechnol*, 15:3-4 (1997).

Papin, et al., "The genome-scale metabolic extreme pathway structure in Haemophilus influenzae shows significant network redundancy," *J Theor Biol*, 215(1):67-82 (2002).

Parks, "Metabolism of sterols in yeast," *CRC Crit Rev Microbiol*, 6(4):301-341 (1978).

Parks, et al., "Use of sterol mutants as probes for sterol functions in the yeast, *Saccharomyces cerevisiae*," *Crit Rev Biochem Mol Biol*, 34(6):399-404 (1999).

Patel, BN and West, TP, ",Degradation of the pyrimidine bases uracil and thymine by *Escherichia coli* B" *Microbios*, 49(199):107-113 (1987).

Paulsen, et al., "Unified inventory of established and putative transporters encoded within the complete genome of *Saccharomyces cerevisiae*," *FEBS Lett*, 430(1-2):116-125 (1998).

Pearson, et al., "Comparison of DNA Sequences With Protein Sequences," *Genomics*, 46(1):24-36 (1997).

Pennisi, "Laboratory Workhouse Decoded," *Science*, 277(5331):1432-1434 (1997).

Persson, et al., "Phosphate permeases of *Saccharomyces cerevisiae*: structure, function and regulation," *Biochim Biophys Acta*, 1422(3):255-272 (1999).

Peterson, et al., "The Comprehensive Microbial Resource," *Nucleic Acids Res*, 29(1):123-125 (2001).

Pharkya, et al., "Exploring the overproduction of amino acids using the bilevel optimization framework OptKnock," *Biotechnol Bioeng*, 84(7):887-899 (2003).

Phelps, et al., "Metabolomics and microarrays for improved understanding of phenotypic characteristics controlled by both genomics and environmental constraints," *Curr Opin Biotechnol*, 13(1):20-24 (2002).

Pitson, et al., "The tricarboxylic acid cycle of Helicobacter pylori," *Eur J Biochem*, 260(1):258-267 (1999).

Pramanik, J and Keasling, J, "Stoichiometric Model of *Escherichia coli* Metabolism: Incorporation of Growth-Rate Dependent Biomass Composition and Mechanistic Energy Requirements," *Biotechnol Bioeng*, 56(4):398-421 (1997).

Price, et al., "Determination of redundancy and systems properties of the metabolic network of Helicobacter pylori using genome-scale extreme pathway analysis," *Genome Res*, 12(5):760-769 (2002).

Price, et al., "Genome-scale models of microbial cells: evaluating the consequences of constraints," *Nat Rev Microbiol*, 2(11):886-897 (2004).

Price, et al., "Network-based analysis of metabolic regulation in the human red blood cell," *J Theor Biol*, 225(2):185-194 (2003).

Przybyla-Zawislak, et al., "Genes of succinyl-CoA ligase from *Saccharomyces cerevisiae*.," *Eur J Biochem*, 258(2):736-743 (1998).

Qian, et al., "Ethanol production from dilute-Acid softwood hydrolysate by co-culture," *Appl Biochem Biotechnol*, 134(3):273-284 (2006).

Reed, et al., "An expanded genome-scale model of *Escherichia coli* K-12 (iJR904 GSM/GPR)," *Genome Biol*, 4(9):R54 (2003).

Reed, JL and Palsson, BO, "Thirteen years of building constraint-based in silico models of *Escherichia coli*" *J Bacteriol*, 185(9):2692-2699 (2003).

Regenberg, et al., "Substrate specificity and gene expression of the amino-acid permeases in *Saccharomyces cerevisiae*," *Curr Genet*, 36(6):317-328 (1999).

Remize, et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl Environ Microbiol*, 66(8):3151-3159 (2000).

Ren, et al., "Genome-wide location and function of DNA binding proteins," *Science*, 290(5500):2306-2309 (2000).

Repetto, B and Tzagoloff, A, "In vivo assembly of yeast mitochondrial alphaketoglutarate dehydrogenase complex," *Mol Cell Biol*, 11(8):3931-3939 (1991).

Reynolds, DJ and Penn, CW, "Characteristics of *Helicobacter pylori* growth in a defined medium and determination of its amino acid requirements," *Microbiology*, 140(Pt 10):2649-2656 (1994).

Rhee, et al., "Activation of gene expression by a ligand-induced conformational change of a protein-DNA complex," *J Biol Chem*, 273(18):11257-11266 (1998).

Romero, PR and Karp, P, "Nutrient-Related Analysis of Pathway/Genome Databases," *Pac Symp Biocomput*, 471-482 (2001).

Saier, MH, "Genome sequencing and informatics: new tools for biochemical discoveries," *Plant Physiol*, 117(4):1129-1133 (1998).

Salgado et al., "RegulonDB (version 3.2): transcriptional regulation and operon organization in *Escherichia coli* K-12," *Nucleic Acids Res*, 29(1):72-74 (2001).

Salmon, et al., "Global gene expression profiling in *Escherichia coli* K12. The effects of oxygen availability and FNR," *J Biol Chem*, 278(32):29837-29855 (2003).

Sauer, et al., "Metabolic Capacity of *Bacillus subtilis* for the Production of Purine Nucleosides, Riboflavin, and Folic Acid," *Biotechnol Bioeng*, 59(2):227-238 (1998).

Sauer, et al., "Metabolic flux ratio analysis of genetic and environmental modulations of *Escherichia coli* central carbon metabolism," *J Bacteriol*, 181(21):6679-6688 (1999).

Sauer, U and Bailey, JE, "Estimation of P-to-O Ratio in *Bacillus subtilis* and Its Influence on Maximum Riboflavin Yield," *Biotechnol Bioeng*, 64(6):750-754 (1999).

Sauer, Uwe, "Evolutionary Engineering of Industrially Important Microbial Phenotypes," *Adv in Biochem Eng Biotechnol*, 73:129-169 (2001).

Savageau, "Biochemical systems analysis. I. Some mathematical properties of the rate law for the component enzymatic reactions," *J Theor Biol*, 25(3):365-369 (1969).

Schaaff-Gerstenschlager, I and Zimmermann, FK, "Pentose-phosphate pathway in *Saccharomyces cerevisiae*: analysis of deletion mutants for transketolase, transaldolase, and glucose 6-phosphate dehydrogenase," *Curr Genet*, 24(5):373-376 (1993).

Schaff, et al., "The Virtual cell" *Proceedings of the Pacific Symposium on Biocomputing*, 228-239 (1999).

Schena, et al., "Quantitative monitoring of gene expression patterns with a complementary DNA microarray," *Science*, 270(5235):467-470 (1995).

Schilling, et al., "Combining Pathway Analysis with Flux Balance Analysis for the Comprehensive Study of Metabolic Systems," *Biotechnol Bioeng*, 71(4):286-306 (2000-2001).

Schilling, et al., "Genome-scale metabolic model of Helicobacter pylori 26695," *J Bacteriol*, 184(16):4582-4593 (2002).

Schilling, et al., "Metabolic Pathway Analysis: Basic Concepts and Scientific Applications in the Post-genomic Era," *Biotechol Prog*, 15(3):296-303 (1999).

Schilling, et al., "Theory for the Systematic Definition of Metabolic Pathways and Their Use in Interpreting Metabolic Function from a Pathway-Oriented Perspective," *J Theor Biol*, 203(3):229-248 (2000).

Schilling, et al., "Toward Metabolic Phenomics: Analysis of Genomic Data Using Flux Balances," *Biotechnol Prog*, 15(3):288-295 (1999).

Schneider, et al., "The *Escherichia coli* gabDTPC operon: specific gamma-aminobutyrate catabolism and nonspecific induction," *J Bacteriol*, 184(24):6976-6986 (2002).

Schuster, et al., "A general definition of metabolic pathways useful for systematic organization and analysis of complex metabolic networks," *Nature Biotechnol*, 18(3):326-332 (2000).

Schuster, et al., "Detection of elementary flux modes in biochemical networks: a promising tool for pathway analysis and metabolic engineering," *Trends Biotechnol*, 17(2):53-60 (1999).

Schuster, et al., "Exploring the pathway structure of metabolism: decomposition into subnetworks and application to Mycoplasma pneumoniae," *Bioinformatics*, 18(2):351-361 (2002).

Schuster, S and Hilgetag, C, "On elementary flux modes in biochemical reaction systems at steady state," *J Biol Syst*, 2(2):165-182 (1994).

Schwikowski, et al., "A network of protein-protein interactions in yeast," *Nature Biotechnol*, 18(12):1257-1261 (2000).

Scott, et al., "The Pendred Syndrome Gene Encodes a Chloride-Iodide Transport Protein," *Nat Genet*, 21(4):440-443 (1999).

Sedivy, JM and Fraenkel, DG, "Fructose bisphosphatase of *Saccharomyces cerevisiae*. Cloning, disruption and regulation of the FBP1 structural gene.," *J Mol Biol*, 186(2):307-319 (1985).

Selkov, et al., "A reconstruction of the metabolism of *Methanococcus jannaschii* from sequence data.," *Gene*, 197(1-2):GC11-26 (1997).

Selkov, et al., "Functional Analysis of Gapped Microbial Genomes: Amino Acid Metabolism of Thiobacillus Ferroxidans," *Proc Natl Acad Sci U.S.A.*, 97(7):3509-3514 (2000).

Selkov, et al., "MPW: the metabolic pathways database," *Nucleic Acids Res*, 26(1):43-45 (1998).

Selkov, et al., "The metabolic pathway collection from EMP: the enzymes and metabolic pathways database," *Nucleic Acids Res*, 24(1):26-28 (1996).

Shen-Orr, et al., "Network motifs in the transcriptional regulation network of *Escherichia coli*," *Nat Genet*, 31(1):64-68 (2002).

Sherlock, et al., "Analysis of large-scale gene expression data," *Curr Opin Immunol*, 12:201-205 (2000).

Shipston, N and Bunch, AW, "The physiology of L-methionine catabolism to the secondary metabolite ethylene by *Escherichia coli*," *J Gen Microbiol*, 135(6), 1489-1497 (1989).

Silve, et al., The immunosuppressant SR 31747 blocks cell proliferation by inhibiting a steroid isomerase in *Saccharomyces cerevisiae*, *Mol Cell Biol*, 16(6):2719-2727 (1996).

Skouloubris, et al., "The Helicobacter pylori UreI protein is not involved in urease activity but is essential for bacterial survival in vivo," *Infect Immun*, 66(9):4517-4521 (1998).

Smith, et al., "Functional analysis of the genes of yeast chromosome V by genetic footprinting.," *Science*, 274(5295):2069-2074 (1996).

Sorlie, et al., "Gene expression patterns of breast carcinomas distinguish tumor subclasses with clinical implications," *Proc Natl Acad Sci U.S.A.*, 98(19):10869-10874 (2001).

Stark, et al., "Amino acid utilisation and deamination of glutamine and asparagine by Helicobacter pylori," *J Med Microbiol*, 46(9):793-800 (1997).

Stephanopoulos, "Metabolic Engineering," *Biotechnol Bioeng*, 58(2-3):119-120 (1998).

Stephanopoulos, "Metabolic Engineering," *Curr Opin Biotechnol*, 5(2):196-200 (1994).

Summers, et al., "*Saccharomyces cerevisiae* cho2 mutants are deficient in phospholipid methylation and cross-pathway regulation of inositol synthesis" *Genetics*, 120(4):909-922 (1988).

Swartz, "A PURE approach to constructive biology.," *Nat Biotechnol*, 19(8):732-733 (2001).

Syvanen, "Accessing genetic variation: Genotyping single nucleotide polymorphisms.," *Nat Rev Genet*, 2(12):930-942 (2001).

Szambelan, et al., "Use of Zymomonas mobilis and *Saccharomyces cerevisiae* mixed with Kluyveromyces fragilis for improved ethanol production from Jerusalem artichoke tubers,"*Biotechnol Lett*, 26(10):845-848 (2004).

Tamayo, et al., "Interpreting patterns of gene expression with self-organizing maps: methods and application to hematopoietic differentiation," *Proc Natl Acad Sci U.S.A,*. 96(6):2907-2912 (1999).

Tanaka, KR, and Zerez, CR, "Red cell enzymopathies of the glycolytic pathway," *Semin Hematol*, 27(2):165-185 (1990).

Taniguchi, M and Tanaka, T, "Clarification of interactions among microorganisms and development of co-culture system for production of useful substances," *Adv Biochem Eng Biotechnol*, 90:35-62 (2004).

Tao, et al., "Engineering a homo-ethanol pathway in *Escherichia coli*: increased glycolytic flux and levels of expression of glycolytic genes during xylose fermentation," *J Bacteriol*, 183(10):2979-2988 (2001).

ter Linde, et al., "Genome-wide transcriptional analysis of aerobic and anaerobic chemostat cultures of *Saccharomyces cerevisiae*," *J Bacteriol*, 181(24):7409-7413(1999).

Thomas, "Boolean Formalization of Genetic Control Circuits," *J Theor Biol*, 42(3):563-585 (1973).

Thomas, "Logical Analyses of Systems Comprising Feedback Loops," J Theor Biol, 73(4):631-656 (1978).

Thomas, D and Surdin-Kerjan, Y, "Metabolism of sulfur amino acids in *Saccharomyces cerevisiae*," *Microbiol Mol Biol Rev*, 61(4):503-532 (1997).

Tomb, et al., "The complete genome sequence of the gastric pathogen Helicobacter pylori," *Nature*, 388(6642):539-547 (1997).

Tomita, et al., "E-Cell: Software Environment for Whole-Cell Simulation," *Bioinformatics,*15(1):72-84 (1999).

Trotter, et al., "A genetic screen for aminophospholipid transport mutants identifies the phosphatidylinositol 4-kinase, STT4p, as an essential component in phosphatidylserine metabolism," *J Biol Chem*, 273(21):13189-13196 (1998).

Uetz, et al., "A comprehensive analysis of protein-protein interactions in *Saccharomyces cerevisiae*," *Nature*, 403(6770):623-627 (2000).

Van den Berg, MA and Steensma, HY, "ACS2, a *Saccharomyces cerevisiae* gene encoding acetyl-coenzyme A synthetase, essential for growth on glucose," *Eur J Biochem*, 231(3):704-713 (1995).

van Dijken, et al., "Alcoholic fermentation by 'non-fermentative' yeasts," *Yeast*, 2(2):123-127 (1986).

van Dijken, et al., "Kinetics of growth and sugar consumption in yeasts," *Antonie Van Leeuwenhoek*, 63(3-4):343-352 (1993).

Vanrolleghem, et al., "Validation of a Metabolic Network for *Saccharomyces cerevisiae* Using Mixed Substrate Studies," *Biotechnol Prog*, 12(4):434-448 (1996).

Varma, A and Palsson, BO, "Metabolic capabilities of *Escherichia coli* II: Optimal Growth Patterns.," *J Theor Biol*, 165:503-522 (1993).

Varma, A and Palsson, BO, "Metabolic capabilities of *Escherichia coli*: I. Synthesis of Biosynthetic Precursors and Cofactors," *J Theor Biol*, 165:477-502 (1993).

Varma, A and Palsson, BO, "Parametric sensitivity of stoichiometric flux balance models applied to wild-type *Escherichia coli* metabolism," *Biotechnol Bioeng*, 45(1):69-79 (1995).

Varma, A and Palsson, BO, "Predictions for Oxygen Supply Control to Enhance Population Stability of Engineered Production Strains," *Biotechnol Bioeng*, 43(4):275-285 (1994).

Varma, A and Palsson, BO, "Stoichiometric flux balance models quantitatively predict growth and metabolic by-product secretion in wild-type *Escherichia coli* W3110," *Appl Environ Microbiol*, 60(10):3724-3731 (1994).

Varma, A., et al., "Metabolic Flux Balancing: Basic Concepts, Scientific and Practical Use," *Biotechnology*, 12:994-998 (1994).

Varma, et al., "Biochemical Production Capabilities of *Escherichia coli*," Biotechnol Bioeng, 42(1):59-73 (1993).

Varma, et al., "Stoichiometric Interpretation of *Escherichia coli* Glucose Catabolism Under Various Oxygenation Rates.," *Appl Environ Microbiol*, 59(8):2465-2473 (1993).

Velculescu, et al., "Analysing uncharted transcriptomes with SAGE," *Trends Genet*, 16(10):423-425 (2000).

Venter, et al., "Shotgun sequencing of the human genome," *Science*, 280(5369):1540-1542 (1998).

Verduyn, "Physiology of yeasts in relation to biomass yields," *Antonie Van Leeuwenhoek*, 60(3-4):325-353 (1991).

Verduyn, et al., "A theoretical evaluation of growth yields of yeasts," *Antonie Van Leeuwenhoek*, 59(1):49-63 (1991).

Verduyn, et al., "Energetics of *Saccharomyces cerevisiae* in anaerobic glucose-limited chemostat cultures," *J Gen Microbiol*, 136:405-412 (1990).

Vissing, et al., "Paradoxically Enhanced Glucose Production During Exercise in Humans with Blocked Glycolysis Caused by Muscle Phosphofructokinase Deficiency," *Neurology*, 47(3):766-771 (1996).

Wang, et al., "Computer-aided baker's yeast fermentations," *Biotechnol and Bioeng*, 19(1):69-86 (1977).

Wang, et al., "Computer control of bakers' yeast production," *Biotechnol and Bioeng*, 21:975-995 (1979).

Waterston, R and Sulston, JE, "The Human Genome Project: reaching the finish line," *Science*, 282(5386):53-54 (1998).

Wen, et al., "Large-scale temporal gene expression mapping of central nervous system development," *Proc Natl Acad Sci U.S.A.*, 95(1):334-339 (1998).

Wiback, SJ and Palsson, BO, "Extreme pathway analysis of human red blood cell metabolism," *Biophys J*, 83:808-818 (2002).

Wieczorke, et al., "Concurrent knock-out of at least 20 transporter genes is required to block uptake of hexoses in *Saccharomyces cerevisiae*," *FEBS Lett*, 464(3):123-128 (1999).

Wills, C and Melham, T, "Pyruvate carboxylase deficiency in yeast: a mutant affecting the interaction between the glyoxylate and Krebs cycles.," *Arch Biochem Biophys*, 236(2):782-791 (1985).

Wingender, et al., "The TRANSFAC system on gene expression regulation," *Nucleic Acids Res*, 29(1):281-283 (2001).

Winzeler, et al., "Functional characterization of the *S. cerevisiae* genome by gene deletion and parallel analysis," Science, 285(5429):901-906 (1999).

Wong, P., et al., "Mathematical Model of the Lac Operon: Inducer Exclusion, Catabolite Repression, and Diauxic Growth on Glucose and Lactose," *Biotechnol Prog*, 13(2):132-143 (1997).

Xie, L and Wang, D, "Integrated Approaches to the Design of Media and Feeding Strategies for Fed-Batch Cultures of Animal Cells," *Trends Biotechnol*, 15(3):109-113 (1997).

Yamada, et al., "Effects of common polymorphisms on the properties of recombinant human methylenetetrahydrofolate reductase,"*Proc Natl Acad Sci U.S.A.*, 98(26):14853-14858 (2001).

Yeung, et al., "Reverse engineering gene networks using singular value decomposition and robust regression," *Proc Natl Acad Sci U.S.A.*, 99(9):6163-6168 (2002).

Yeung, et al., *Bioinformatics*, "Model-based clustering and data transformations for gene expression data," 17(10)977-87 (2001).

Yoshida, et al., "Combined transcriptome and proteome analysis as a powerful approach to study genes under glucose repression in *Bacillus subtilis*," *Nucleic Acids Res*, 29(3):683-692 (2001).

Zanella, A and Bianchi, P. "Red cell pyruvate kinase deficiency: from genetics to clinical manifestations," *Bailliere's Best Pract Res Clin Haematol* 13(1):57-81 (2000).

Zeng, et al., "Use of respiratory quotient as a control parameter for optimum oxygen supply and scale-up of 2,3-butanediol production under microaerobic conditions,"*Biotechnol Bioeng*, 44(9):1107-1114 (1994).

Zhu, J and Zhang, MQ, "SCPD: a promoter database of the yeast *Saccharomyces cerevisiae*," Bioinformatics, 15(7-8):607-611 (1999).

Zigova, "Effect of RQ and pre-seed conditions on biomass and galactosyl transferase production during fed-batch culture of *S. cerevisiae* BT150," *J Biotechnol*, 80(1):55-62 (2000).

Zweytick, et al., "Biochemical characterization and subcellular localization of the sterol C-24(28) reductase, erg4p, from the yeast *Saccharomyces cerevisiae*," *FEBS Lett*, 470(1):83-87 (2000).

URL Genome.jp Website, KEGG *Bacillus subtillis*, 1-7 (2005).

URL mips.gsf.de/proj/yeast/pathways/ on 06/06/08, MIPS, website: Comprehensive Yeast Genome Database—Pathways (1998).

Akutsu, "Estimation Algorithm of Genetic Network," Mathmatical Science (Suri-Kagaku) *Science* 37(6)40-46 (1999).

Aristidou and Penttila, "Metabolic engineering applications to renewable resource utilization," *Curr Opin in Biotech* 11(2)187-198 (2000).

Callis "Regulation of Protein Degradation," *The Plant Cell* 7:845-857 (1995).

Carrier and Keasling, "Investigating Autocatalytic Gene Expression Systems through Mechanistic Modeling," *J Theor Biol* 201(1):25-36 (1999).

Chartrain, et al., "Metabolic engineering and directed evotion for the production of pharmaceuticals," Curr Opin in Biotech 11(2):209-214 (2000).

Dafoe, et al., "In Silico Knowledge Discovery Biomedical databases," Proceedings of the SPIE Fifth Workshop on Neural Networks, San Francisco, Nov. 7-10, 1993.

DeRisi, et al., "Use of cDNA microarray to analyse gene expression patters in human cancer," Nat Gene 14:457-460 (1996).

Duarte, et al., "Reconstruction and validation of *Saccharomyces cerevisiae* iND750, a fully compartmentalized genome-scale metabolic model," *Genome Res* 14(7):1298-1309 (2004).

Feist and Palsson "The growing scope of applications of genome-scale metabolic reconstructions using *Escherichia coli*," *Natural Biotech* 26(6):659-667 (2008).

Fotheringham, "Engineering biosynthetic pathways: new routes to chiral amino acids," *Curr Opin in Chem Biology* 4(1):120-124 (2000).

Gombert and Nielsen, "Mathematical modeling of metabolism," *Curr Opin in Biotech* 11(2):180-186 (2000).

Guardia, et al., "Cybernetic modeling and regulation of metabolic pathways in multiple steady states of hybridoma cells," *Biotech Progress* 16(5):847-853 (2000).

Kaufman, et al., "Towards a logical analysis of the immune response," *J of Theoretical Biology* 114(4):527-561 (1985).

Kunst and Devine, "The project of sequencing the entire *Bacillus substilis* genome," *Res in Microbiology* 142:905-912 (1991).

Lee, et al., "Incorporating qualitative knowledge in enzyme kinetic models using fuzzy logic," *Biotech and Bioengineer* 62(6):722-729 (1999).

Lynd, et al., "Biocommodity Enginering," *Biotechnology Progress* 15:777-793 (1999).

McAdams and Shapiro, "Circuit simulation of genetic networks," *Science* 269:651-656 (1995).

McAdams and Arkin, "Stochastic mechanisms in gene expression," *Proc of the National Academy of Sciences of the USA* 94(3):814-819 (1997).

McAdams and Arkin, "It's a noisy business! Genetic regulation at the nanomolar scale," *Trends in Genetics* 15(2):65-69 (1999).

Ostergaard, et al., "Increasing galactose consumption by *Saccharomyces cerevisiae* through metabolic engineering of the GAL gene regulatory network," *Nat Biotech* 18:1283-1286 (2000).

Pieper and Reineke, "Engineering bacteria for bioremediation," *Curr Opin in Biotech* 11(3):262-270 (2000).

Raclot, et al., "Selective release of human adipocyte fatty acids according to molecular structure," *Biochem J* 324 (Pt3):911-915 (1997).

Rao and Arkin, "Control motifs for intracellular regulatory networks," *Annual Rev of Biomed Engineer* 3:391-419 (2001).

Savageau, "Development of fractal kinetic theory for enzyme-catalysed reactions and implications for the design of biochemical pathways," *Biosystems* 47(1-2):9-36 (1998).

Savinell and Palsson, "Network Analysis of Intermediary Metabolism using Linear Optimization. II. Interpretation of Hybridoma Cell Metabolism," *J Theor Biol* 154:455-473 (1992).

Savinell and Palsson, "Network Analysis of Intermediary Metabolism using Linear Optimization. I. Development of Mathematical Formalism," *J Theor Biol*, 154:421-454 (1992).

Somogyi and Sniegoski "Modeling the complexity of genetic networks: understanding the multigenic and pleitropic regulation," *Complexity* 1(6):45-63 (1996).

Tandeitnik, et al., "Modeling of biological neurons by artificial neural networks," *Nineteenth Convention of Electrical and Electronics Engineers in Israel, Jerusalem, Israel, New York, NY USA*, pp. 239-242 (1996).

Thieffry and Thomas, "Dynamical behavior of biological regulatory networks II. Immunity control in bacteriophage lambda," *Bulletin of Math Biology* 57(2):277-297(1995).

Varner, "Large-scale prediction of phenotype: concept," *Biotech and Bioengineer* 69(6):664-678 (2000).

Vaseghi, et al., "In vivo Dynamics of the pentose phosphate pathway in *Saccharomyces cerevisiae*," *Metabolic Engineer* 1:128-140 (1999).

Vo, et al., "Reconstruction and functional characterization of the human mitochondrial metabolic network abased on proteomic and biochemical dataz," *J Biol Chem* 279(38):39532-39540 (2004).

Xie and Wang, "Material Balance Studies on Animal Cell Metabolism Using a Stoichiometrically Based Reaction Network," *Biotech and Bioengineer* 52:579-590 (1996).

Xie and Wang, "Energy Metabolism and ATP Balance in Animal Cell Cultivation Using a Stoichiometrically Based Reaction Network," Biotech and Bioengineer, 52:591-601 (1996).

url. www.i-sis.org.uk/WITBRL.php; Hoppert, M. (2004).

* cited by examiner

FIG. 19

METHODS AND SYSTEMS TO IDENTIFY OPERATIONAL REACTION PATHWAYS

RELATED APPLICATIONS

This application claims priority under 35 U.S.C. §119(e) to U.S. Provisional Application Ser. No. 60/419,023 filed Oct. 15, 2002, the contents of which are incorporated herein by reference in its entirety.

BACKGROUND OF THE INVENTION

This invention relates generally to the construction of in silico model organisms and, more specifically, methods and systems specifying operational reaction pathways and for the generation of optimal in silico models of actual organisms.

Therapeutic agents, including drugs and gene-based agents, are being rapidly developed by the pharmaceutical industry with the goal of preventing or treating human disease. Dietary supplements, including herbal products, vitamins and amino acids, are also being developed and marketed by the nutraceutical industry. Additionally, efforts for faster and more effective methods for biological fermentation and other bioprocessing of food stuffs and industrial compounds has been under development. Faster and more efficient production of crops and other agricultural products is also yet another area of intense development in the food industry.

Because of the complexity of biochemical reaction networks in and between cells of an organism, even relatively minor perturbations caused by a therapeutic agent, change in a dietary component or environmental or growth conditions, can affect hundreds of biochemical reactions. Such changes or perturbations can lead to both desirable and undesirable effects in any therapeutic, industrial or agricultural process involving living cells. It would therefore be beneficial if a particular process could predict the effects on a living system such as a cell or organism of such perturbations.

However, current approaches to therapeutic, industrial and agricultural development for compounds and processes used therein do not take into account the effect of perturbations on cellular behavior at the level of accuracy needed for efficient and economical production of products. In order to design effective methods of manipulating cellular activities for the optimization of such processes or to achieve the optimal intended effect of an applied a compound, it would be helpful to understand cellular behavior from an integrated perspective.

However, cellular behaviors involve the simultaneous function and integration of many interrelated genes, gene products and chemical reactions. Because of this interconnectivity, it is difficult to predict a priori the effect of a change in a single gene or gene product, or the effect of a drug or an environmental factor, on cellular behavior. The ability to accurately predict cellular behavior under different conditions would be extremely valuable in many areas of medicine and industry. For example, if it were possible to predict which gene products are suitable drug targets, it would considerably shorten the time it takes to develop an effective antibiotic or anti-tumor agent. Likewise, if it were possible to predict the optimal fermentation conditions and genetic make-up of a microorganism for production of a particular industrially important product, it would allow for rapid and cost-effective improvements in the performance of these microorganisms.

Thus, there exists a need for models and modeling methods that can be used to accurately simulate and effectively analyze the behavior of cells and organisms under a variety of conditions. The present invention satisfies this need and provides related advantages as well.

SUMMARY OF THE INVENTION

The invention provides a method of identifying an operational reaction pathway of a biosystem. The method consists of: (a) providing a set of systemic reaction pathways through a reaction network representing said biosystem; (b) providing a set of phenomenological reaction pathways of said biosystem, and (c) comparing said set of systemic reaction pathways with said set of phenomenological reaction pathways, wherein a pathway common to said sets is an perational reaction pathway of said biosystem.

Also provided is a method of refining a biosystem reaction network. The method consists of: (a) providing a mathematical representation of a biosystem; (b) determining differences between observed behavior of a biosystem and in silico behavior of said mathematical representation of said biosystem under similar conditions; (c) modifying a structure of said mathematical representation of said biosystem; (d) determining differences between said observed behavior of said biosystem and in silico behavior of said modified mathematical representation of said biosystem under similar conditions, and (e) repeating steps (d) and (e) until behavioral differences are minimized, wherein satisfaction of a predetermined accuracy criteria indicates an improvement in said biosystem reaction network.

Further provided is a method of reconciling biosystem data sets. The method consists of: (a) providing a first reaction network reconstructed from legacy data comprising a plurality of hierarchical reaction categories; (b) providing a second reaction network obtained from empirical data, and (c) determining a consistency measure between said hierarchical reaction categories in said first reaction network and elements in said second reaction network, wherein a high degree of said consistency measure for said hierarchical reaction categories indicates the validity of said first reaction network or a sub-component thereof.

A method of determining the effect of a genetic polymorphism on whole cell function is also provided. The method consists of: (a) generating a reaction network representing a biosystem with a genetic polymorphism-mediated pathology; (b) applying a biochemical or physiological condition stressing a physiological state of said reaction network, and (c) determining a sensitivity to said applied biochemical or physiological condition in said stressed physiological state compared to a reaction network representing a normal biosystem, wherein said sensitivity is indicative of a phenotypic consequence of said genetic polymorphism-mediated pathology.

The invention additionally provides a method of diagnosing a genetic polymorphism-mediated pathology. The method consists of: (a) applying a biochemical or physiological condition stressing a physiological state of a reaction network representing a biosystem with a genetic polymorphism-mediated pathology, said applied biochemical or physiological condition correlating with said genetic polymorphism-mediated pathology, and (b) measuring one or more biochemical or physiological indicators of said pathology within said reaction network, wherein a change in said one or more biochemical or physiological indicators in said stressed state compared to an unstressed physiological state indicates the presence of a genetic polymorphism corresponding to said pathology.

BRIEF DESCRIPTION OF THE DRAWINGS

FIG. 19 shows calculation of the expression of regulated genes in an actual organism and model system resulting from phase I of an iterative process of the invention.

DETAILED DESCRIPTION OF THE INVENTION

The invention provides methods and systems for determining the interaction, integration and coordination of a set of components of a biosystem. The invention can thus be used to rapidly and systematically specify a reconstructed biochemical reaction network at the genome-scale and to relate the activity of the components and their interaction to a specific phenotype or physiological state. Understanding which components are operational under particular conditions allows for improved methods of engineering desirable functions into living cells, fixing malfunctioning circuits, and controlling endogenous circuits by the proper manipulation of the cells' environment. Furthermore, a rapid method for characterizing a biochemical network allows for the characterization of a virtually uncharacterized biosystem with a minimum of experimental effort.

Figure 1:
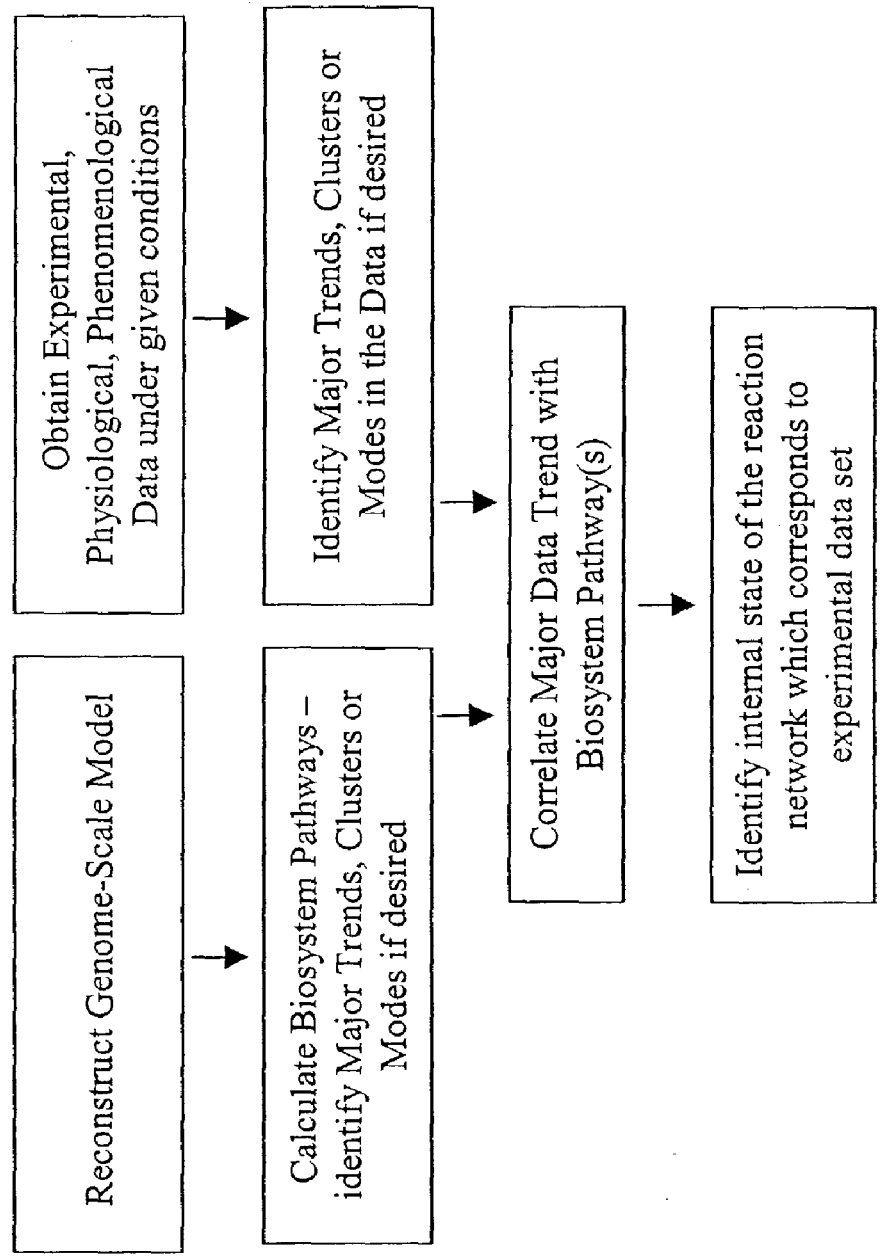
FIG. 1 shows a schematic diagram for steps involved in determining operational pathways of a biochemical reaction network.

The invention provides a method for determining the operational pathways of a biochemical reaction network. The invention method is practiced by (a) providing a biochemical reaction network, comprised of reactions which can be regulated; (b) providing a set of experimental data which represent various physiological or pathological states of the biosystem under given conditions; (c) determining a set of systemic pathways which define the biosystem in whole or in part; (d) determining a set of phenomenological reaction pathways which describe the experimental states of the biosystem; and (e) determining the operational pathways common to both the systemic and phenomenological pathways sets both at whole-genome and biosystem subcomponent scale (FIG. 1).

As used herein, the term "reaction" is intended to mean a chemical conversion that consumes a substrate or forms a product. A conversion included in the term can occur due to the activity of one or more enzymes that are genetically encoded by an organism, or can occur spontaneously in a cell or organism. A conversion included in the term can be, for example, a conversion of a substrate to a product, such as one due to nucleophilic or electrophilic addition, nucleophilic or electrophilic substitution, elimination, reduction or oxidation. A conversion included in the term can also be a change in location, such as a change that occurs when a reactant is transported across a membrane or from one compartment to another. The substrate and product of a reaction can be differentiated according to location in a particular compartment, even though they are chemically the same. Thus, a reaction that transports a chemically unchanged reactant from a first compartment to a second compartment has as its substrate the reactant in the first compartment and as its product the reactant in the second compartment. The term "reaction" also includes a conversion that changes a macromolecule from a first conformation, or substrate conformation, to a second conformation, or product conformation. Such conformational changes can be due, for example, to transduction of energy due to binding a ligand such as a hormone or receptor, or from a physical stimulus such as absorption of light. It will be understood that when used in reference to an in silico biochemical reaction network, a "reaction" is intended to be a representation of a conversion as described above.

As used herein, the term "reactant" is intended to mean a chemical that is a substrate or a product of a reaction. The term can include substrates or products of reactions catalyzed by one or more enzymes encoded by an organism's genome, reactions occurring in an organism that are catalyzed by one or more non-genetically encoded catalysts, or reactions that occur spontaneously in a cell or organism. Metabolites are understood to be reactants within the meaning of the term. It will be understood that when used in the context of an in silico model or data structure, a reactant is understood to be a representation of chemical that is a substrate or product of a reaction.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, reduction or oxidation or that is to change location such as by being transported across a membrane or to a different compartment. The term can include a macromolecule that changes conformation due to transduction of energy.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, reduction or oxidation or that has changed location such as by being transported across a membrane or to a different compartment. The term can include a macromolecule that changes conformation due to transduction of energy.

As used herein, the term "regulatory reaction" is intended to mean a chemical conversion or interaction that alters the activity of a catalyst. A chemical conversion or interaction can directly alter the activity of a catalyst such as occurs when a catalyst is post-translationally modified or can indirectly alter the activity of a catalyst such as occurs when a chemical conversion or binding event leads to altered expression of the catalyst. Thus, transcriptional or translational regulatory pathways can indirectly alter a catalyst or an associated reaction. Similarly, indirect regulatory reactions can include reactions that occur due to downstream components or participants in a regulatory reaction network. When used in reference to a data structure or in silico model, the term is intended to mean a first reaction that is related to a second reaction by a function that alters the flux through the second reaction by changing the value of a constraint on the second reaction.

A regulatory reaction can further include information about inhibitory or inducing effects of an active or inactive regulator on transcription of a gene. For example, a regulatory reaction may have one or more regulators associated with it which effect transcription of a gene.

A regulatory reaction can further include information about the interaction of regulators which influence gene expression. For example a regulatory reaction may have a combination of two or more regulators associated with it which are dependent upon each other to effect transcription of a gene.

A regulatory reaction can further include information in the form of Boolean logic statements which indicates the interaction and dependency of regulators for transcription of a particular gene. For example, a particular gene may have a Boolean logic assigned to it which describes the necessary regulators and regulatory interactions required for expression of that gene.

As used herein, the term "regulator" refers to a substance which regulates transcription, post-transcriptional modification or activity of one or more genes, proteins, mRNA transcripts. Such a regulator may be a regulatory protein, small molecule and the like.

As used herein, the term "regulatory event" is intended to mean a modifier of the flux through a reaction that is independent of the amount of reactants available to the reaction. A modification included in the term can be a change in the presence, absence, or amount of an enzyme that catalyzes a reaction. A modifier included in the term can be a regulatory reaction such as a signal transduction reaction or an environmental condition such as a change in pH, temperature, redox potential or time. It will be understood that when used in reference to an in silico model or data structure a regulatory event is intended to be a representation of a modifier of the flux through a reaction that is independent of the amount of reactants available to the reaction.

As used herein, the term "reaction network" refers to a representation of the functional interrelationships between a collection of reactions and reaction components. Reaction components included in a reaction network can be any component involved in a reaction, such as a substrate, product, enzyme, cofactor, activator, inhibitor, transporter, and the like. Functional interrelationships include, for example, those between a substrate and its product; those between a substrate or product and the enzyme that catalyzes the conversion from substrate to product; those between an enzyme and its cofactor, activator or inhibitor; those between a receptor and a ligand or other pairs of macromolecules that physically interact; those between a macromolecule and its transporter; those between proteins involved in transcriptional regulation and their DNA-binding sites in regulatory regions regulating specific target genes; and the like.

A reaction network can further include information regarding the stoichiometry of reactions within the network. For example, a reaction component can have a stoichiometric coefficient assigned to it that reflects the quantitative relationship between that component and other components involved in the reaction.

A reaction network can further include information regarding the reversibility of reactions within the network. A reaction can be described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

A reaction network can include both intra-system reactions and exchange reactions. Intra-system reactions are the chemically and electrically balanced interconversions of chemical species and transport processes, which serve to replenish or drain the relative amounts of certain reactants. Exchange reactions are those which constitute sources and sinks, allowing the passage of reactants into and out of a compartment or across a hypothetical system boundary. These reactions represent the demands placed on the biological system. As a matter of convention the exchange reactions are further classified into demand exchange and input/output exchange reactions. Input/output exchange reactions are used to allow components to enter or exit the system. A demand exchange reaction is used to represent components that are required to be produced by the cell for the purposes of creating a new cell, such as amino acids, nucleotides, phospholipids, and other biomass constituents, or metabolites that are to be produced for alternative purposes.

A reaction network can further include both metabolic and regulatory reactions. Metabolic reactions can be represented by stoichiometry and reversibility while regulatory reactions can be represented by Boolean logic statements which both depend on and effect the presence or absence, activity or inactivity of metabolic or regulatory proteins.

A reaction network can be represented in any convenient manner. For example, a reaction network can be represented as a reaction map with interrelationships between reactants indicated by arrows. For mathematical manipulation according to the methods of the invention, a reaction network can conveniently be represented as a set of linear algebraic equations or presented as a stoichiometric matrix. A stoichiometric matrix, S, can be provided, which is an m x n matrix where m corresponds to the number of reactants and n corresponds to the number of reactions in the network. Stoichiometric matrices and methods for their preparation and use are described, for example, in Schilling et al., Proc. Natl. Acad. Sci. USA 95:4193-4198 (1998). As a further example, a reaction network can conveniently be represented as a set of linear algebraic equations and Boolean logic equations. The Boolean logic equations may be evaluated and lead to the removal or addition of certain reactions from the stoichiometric matrix, due to the inhibitory or inducing effect of regulatory events. Such a representation is described, for example, in Covert M W, Schilling C H, Palsson B. J Theor Biol. 213:73-88 (2001).

The invention methods can be practiced with reaction networks of either low or high complexity, such as networks that include substantially all of the reactions that naturally occur for a particular biosystem. Thus, a reaction network can include, for example, at least about 10, 50, 100, 150, 250, 400, 500, 750, 1000, 2500, 5000 or more reactions, which can represent, for example, at least about 5%, 10%, 20%, 30%, 50%, 60%, 75%, 90%, 95% or 98% of the total number of naturally occurring reactions for a particular biosystem.

A reaction network represents reactions that participate in one or more biosystems. As used herein, the term "biosystem" refers to an entire organism or cell therefrom, or to a "biological process" that occurs in, to or by the organism or cell. Thus, a reaction network can represent reactions that occur at the whole organismal, whole cell or subcellular level. Additionally, the reaction network may represent interactions between different organisms or cells.

The term "organism" refers both to naturally occurring organisms and to non-naturally occurring organisms, such as genetically modified organisms. An organism can be a virus, a unicellular organism, or a multicellular organism, and can be either a eukaryote or a prokaryote. Further, an organism can be an animal, plant, protist, fungus or bacteria. Exemplary organisms include pathogens, and organisms that produce or can be made to produce commercially important products, such as therapeutics, enzymes, nutraceuticals and other macromolecules. Examples of organisms include *Arabidopsis thaliana, Bacillus subtilis, Bos taurus, Caenorhabditis elegans, Chlamydomonas reihardtii, Danio rerio, Dictyostelium discoideum, Drosophila melanogaster, Escherichia coli,* hepatitis C virus, *Haemophilus influenzae, Helicobacter pylori, Homo sapiens, Mus musculus, Mycoplasma pneumoniae, Oryza sativa, Plasmodium falciparum, Pnemocystis caninii, Rattus norvegicus, Saccharomyces cerevisiae, Schizosaccharomyces pombe, Takifugu rubripes, Xenopus laevis, Zea mays,* and the like.

A "biological process" of an organism or cell refers to a physiological function that requires a series of integrated reactions. A biological process can be, for example, cellular metabolism; cell motility; signal transduction (including transduction of signals initiated by hormones, growth factors, hypoxia, cell-substrate interactions and cell-cell interactions); cell cycle control; transcription; translation; degradation; sorting; repair; differentiation; development; apoptosis; and the like. Biological process are described, for example, in Stryer, L., Biochemistry, W. H. Freeman and Company, New York, 4th Edition (1995); Alberts et al., Molecular Biology of The Cell, Garland Publishing, Inc., New York, 2nd Edition (1989); Kuby, Immunology, 3rd Edition, W. H. Freeman & Co., New York (1997); and Kornberg and Baker, DNA Replication, W. H. Freeman and Company, New York, 2nd Edition (1992).

In one embodiment, the biosystem includes the biological process of cellular metabolism, and the reaction network representing the biosystem, referred to as a "metabolic reaction network," includes cellular metabolic reactions. A basic review of cellular metabolism can be found, for example, in Stryer, L., Biochemistry, W. H. Freeman and Company, New York, 4th Edition (1995). Cellular metabolism can be usefully divided into central and peripheral metabolic reactions. Central metabolism includes reactions that belong to glycolysis, pentose phosphate pathway (PPP), tricarboxylic acid (TCA) cycle and respiration. Peripheral metabolism, which includes all metabolic reactions that are not part of central metabolism, includes reactions involved in the biosynthesis of an amino acid, degradation of an amino acid, biosynthesis of a purine, biosynihesis of a pyrimidine, biosynthesis of a lipid, metabolism of a fatty acid, biosynthesis of a cofactor, metabolism of a cell wall component, transport of a metabolite or metabolism of a carbon source, nitrogen source, phosphate source, oxygen source, sulfur source, hydrogen source or the like.

In another embodiment, the biosystem includes the biological process of transcriptional regulation, and the reaction network representing the biosystem, referred to as a "transcriptional regulatory reaction network," includes cellular transcriptional regulatory reactions. A basic review of cellular transcriptional regulation can be found, for example, in Alberts et al., Molecular Biology of The Cell, Garland Publishing, Inc., New York, 2nd Edition (1989). Transcriptional regulatory events may be grouped by the types of genes regulated, for example those genes associated with metabolism, cell cycle, flagellar biosynthesis and the like.

In another embodiment, the biosystem includes the biological processes of cellular metabolism and transcriptional regulation and the reaction network representing the biosystem includes both metabolic and transcriptional regulatory reactions.

A reaction network that includes substantially all of the reactions of a whole organism or cell, or substantially all of the reactions of a particular biological process of an organism or cell, is referred to as a "genome-scale" reaction network. Genome-scale reaction networks representing the metabolism of various organisms have been described, including *E. coli* (PCT publication WO 00/46405); *H. pylori* (Schilling et al., J. Bacteriol. 184:4582-4593 (2002)); and *H. influenzac* Edwards J. S. and Palsson B. O. J. Biol. Chem. 274:17410-6 (2001)).

For other biosystems, genome-scale reaction networks can be prepared by methods known in the art. Generally, these methods involve first generating a comprehensive list of reactions that are capable of occurring in the organism, cell or biosystem, and determining their interconnectivity. The list can include reactions determined from an analysis of the annotated genome of the organism, supplemented as required from scientific literature and from experimental data. Also included can be transport reactions, biomass composition demands, growth associated energy requirements, and the like.

The genome sequences of a large number of animals, plants, protists, fungi, bacteria and viruses have been completed or are in progress (see, for example, genome entries in The Institute for Genome Research (TIGR) database (World Wide Web at tigr.org/tdb/) and in the NCBI Entrez Genome database (World Wide Web at ncbi.nlm.nih.gov/entrez/query.fcgi?db=Genome)). Other World Wide Web-based sources of annotated genome sequence information and reconstructed network information include EcoCyc, Metabolic pathways database (MPW), Kyoto Encyclopedia of Genes and Genomes (KEGG), What is There (WIT) and Biology Workbench.

For organisms whose genomes have not yet been sequenced, a variety of methods for obtaining the genomic sequence are known in the art. In most large-scale genome sequencing methods, every step from isolating DNA, cloning or amplifying DNA, preparing sequencing reactions, and separating and detecting labeled fragments to obtain sequence, is automated (Meldrum, Genome Res. 10:1081-1092 (2000)). Most methods use a combination of sequencing methods, such as a combination of random shotgun sequencing with a directed finishing phase. Other methods use a whole-genome shotgun approach, in which random fragments of total genomic DNA are subcloned directly, and high-throughput sequencing is used to provide redundant coverage of the genome. Another approach is to sequence each end of every BAC in a genome library, and match a finished sequence to a BAC end sequence to select the next clone (Venter et al., Science 280:1540-1542 (1998); Waterston et al, Science 282:53-54 (1998)).

For a newly sequenced genome, the open reading frames (ORFs) or coding regions may be distinguished from the rest of the DNA sequence by variety of methods. Determining the location of an ORF in a DNA sequence, its strand, and nucleotide composition may be conducted by searching for gene signals (e.g. promoters, binding sites, start and stop codon, etc.) or by analyzing gene content (e.g. codon preference, positional base frequency, etc.), or a combination of both methods. Algorithms and computational tools are available to determine the ORFs of an entire DNA sequence using these methods available through institutes such as the University of Wisconsin Genetics Computer Group and National Center for Biotechnology Information. Furthermore, other computational algorithms have been developed by which bacterial or eukaryotic genes may be identified by algorithmic methods such as hidden Markov models, which routinely find more than 99% of protein-coding regions and RNA genes (Pevzner, "Computational molecular biology: an algorithmic approach," in Computational Molecular Biology. Cambridge, Mass.:MIT Press, xviii, p. 314 (2000); Baldi et al., "Bioinformatics: the machine learning approach," in Adaptive Computation and Machine Learning. Cambridge, Mass.: MIT Press xviii, p. 351 (1998); Fraser et al., Nature 406:799-803 (2000)).

In order to assign function to the coding regions, newly identified ORFs are searched against databases containing genes and protein sequences of known function for sequence similarity. Several algorithms such as the BLAST and FASTA family of programs have been developed and are available publically by which the similarity of a functionally unknown ORF may be determined against functionally annotated genes. A major portion of unidentified genes in a newly sequence organism can be assigned functionally with this procedure.

If the putative function of a gene is not established by gene or protein sequence similarity, other techniques such as gene clustering by function or location may be used to assess the role of a gene in the network. Gene products that participate in the same overall function can constitute a pathway in the cell. "Missing links" in a pathway constructed from an initial sequence annotation suggests the existence of genes that have not yet been identified. Searching the sequence against other organisms provides clues about the possible nucleotide sequence of the missing genes, which in turn facilitates targeting functionality of the unassigned coding regions. Algorithms have been developed that perform this procedure in various genome databases such as KEGG and WIT. In addition, genes of the neighboring location may be clustered into operons that are regulated and function in a coordinated fashion when the DNA sequence is compared to that of other organisms. From the annotated genetic information, together with biochemical and physiological information, the interrelatedness of reactions and reaction components is determined and the reaction network is completed.

In addition to defining the ORFs or coding regions of the genome, regulatory regions can be defined by variety of methods. Regulatory regions contain binding sites for transcriptional regulators and components of the transcriptional machinery. These sites determine the specificity of transcriptional regulation as the ability of transcriptional regulators to regulate the gene controlled by the regulatory region. The methods to identify regulatory regions and sites include comparing non-coding regions of closely related genomes to identify highly conserved segments of the genome that may correspond to regulatory regions. Groups of non-coding regions of a genome can also be searched for commonly occurring sequence fragments to identify specific binding site patterns in the genome. These groups can be defined for example by similarity in biological function of the genes controlled by the regulatory regions. In addition existing definitions of binding site patterns for specific transcriptional regulators stored in specific databases such as Saccharomyces Promoter Database (Zhu and Zhang, Bioinformatics 15:607-611 (1999)) or TRANSFAC (Wingender et al., Nucl. Acids Res. 29:281-283 (2001)) can be used to search the genome for new binding sites for a regulator. Identifying regulatory sites for specific transcription regulators allows establishing potential target genes regulated by these regulators and thus suggesting new regulatory reactions to be added to the regulatory network.

As used herein, the term "reaction pathway" refers to a route through a reaction network through which reaction components, regulatory information or signaling molecules can potentially flow. It will be appreciated that the actual amount and/or rate of substrate to product conversion through a reaction pathway (also known as "flux") is a function of the physiological state of the biosystem under consideration, and that reaction pathways (including operational, extreme and phenomenological reaction pathways as described below) are generally specified in connection with the physiological state of the biosystem. The term "physiological state" is intended to refer to any specified internal and external parameters that affect, or are likely to affect, flux through a biosystem. Parameters that can affect flux include, for example, the actual or intended inputs to the biosystem (such as the carbon, nitrogen, phosphorus, sulfur or hydrogen source; the presence or amount of oxygen, nutrients, hormones, growth factors, inhibitors and the like); the actual or intended outputs of the biological system (such as biomass components, secreted products and the like) and environmental variables (such as temperature, pH and the like). Other parameters that can affect flux include, for example, the state of differentiation or transformation of the cell; cell age; its contact with a substrate or with neighboring cells; the addition or deletion of expressed genes; and the like.

As used herein, term "systemic reaction pathway" refers to a reaction pathway identified by an automated method applied to a suitable representation of a reaction network. The method may involve mathematical or algorithmic operations to identify the reaction pathways, and it may include user definable parameters that influence the identification of reaction pathways. The systemic reaction pathways need not to be unique and they may only apply to a subset of the reaction network.

Methods of identifying systemic reaction pathways using convex analysis have been described in the art. Such methods include, for example, stoichiometric network analysis (SNA) (Clarke, Cell Biophys. 12:237-253 (1988); elementary mode analysis (Schuster et al., Trends Biotech. 17:53-60 (1999); and extreme pathway analysis (Schilling et al., J. Theor. Biol. 203:229-248 (2000); Schilling et al., Biotechnol. Bioeng. 71:286-306 (2001)). The distinctions between these types of analysis are described in Schilling et al. supra (2000).

In one embodiment, the systemic reaction pathway is an extreme pathway. The term "extreme pathway" refers to a systemically independent pathway that spans a convex, high-dimensional space that circumscribes all potential steady state flux distributions achievable by a defined reaction network.

It will be understood that the steps needed to "provide" a set of systemic reaction pathways for use in the invention methods will depend on the amount and type of information already available regarding the biosystem and reaction network. For certain biosystems and physiological states, sets of extreme reaction pathways have been described in the art. For example, extreme pathways for a human red blood cell metabolic network are described in Wiback et al., Biophys. J. 83:808-818 (2002). Extreme pathways for a *H. influenzae* metabolic network are described in Schilling et al., J. Theor. Biol. 203:249-283 (2000) and Papin et al., J. Theor. Biol. 215:67-82 (2002). Extreme pathways for a *H. pylori* metabolic network are described in Price et al., Genome Res. 12:760-769 (2002).

Extreme reaction pathways can also be determined de novo, using methods known in the art (Schilling et al. supra (2000); Schilling et al. supra (2001)). Appropriate stoichiometric and thermodynamic constraints can be imposed on the intrasystem and exchange reactions in the reaction network under steady-state conditions. Constraints can also imposed on the input and output of reactants to and from the biosystem. Optionally, regulatory constraints can also be imposed (Covert et al., J. Theor. Biol. 213:73-88 (2001); Covert et al., J. Biol. Chem. 277:28058-28064 (2002)). This results in a system of linear equalities and inequalities that can be solved using convex analysis. The solution space corresponds geometrically to a convex polyhedral cone in high-dimensional space emanating from the origin, which is referred to as the steady state "flux cone." Within this flux cone lie all of the possible steady-state solutions, and hence all the allowable flux distributions of the biosystem. The extreme pathways correspond to vectors that define the edges of the flux cone.

Figure 2A:
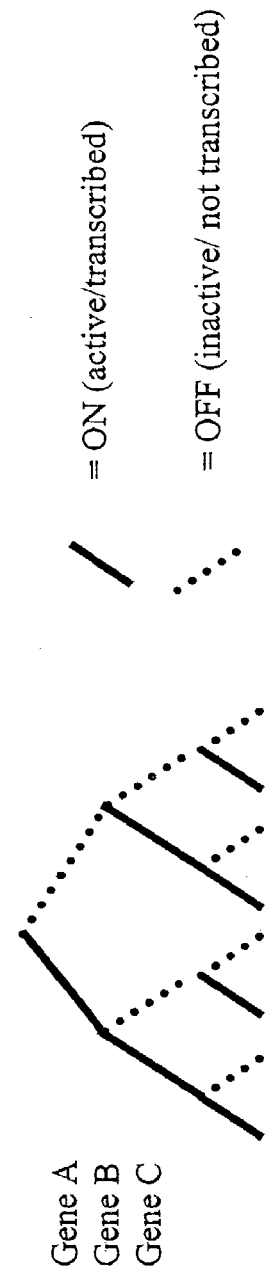
FIG. 2a shows a schematic representation of systemic reaction pathways as one branch of a regulatory tree with the regulated genes shown on the horizontal axis.
Figure 2A:
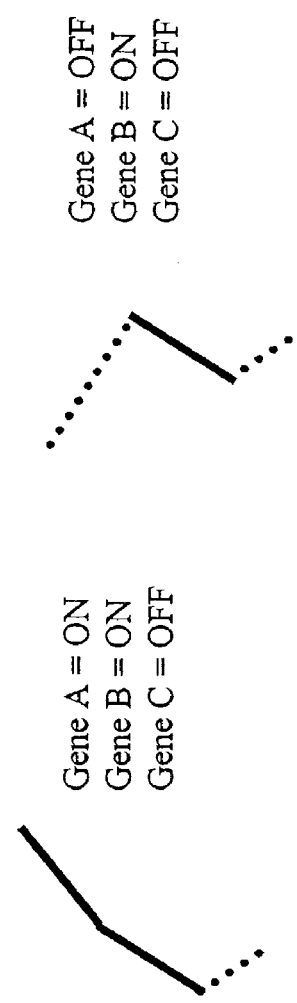

In another embodiment, the systemic reaction pathway is one branch of a regulatory tree. The regulated genes of a biosystem may be depicted as shown in FIG. 2a with the regulated genes shown on the horizontal axis. In a Boolean representation, each protein and each gene may be considered "on" or "off" (active or inactive, respectively). The combination of the activity state of all genes and proteins in a biosystem may be considered a "systemic regulatory pathway" or a "systemic signaling pathway".

In another embodiment, the systemic reaction pathway is a set of regulators and regulatory reactions influencing the activity of a regulated gene or the set of genes regulated by a regulator or a group of regulators. These sets may be identified by analyzing the connectivity of a regulatory network represented as a graph and identifying nodes in the network connected to a particular node (regulator or regulated gene). The smallest possible set of such kind is one involving one regulatory reaction between a regulator and a target gene.

As used herein, the term "phenomenological reaction pathway" refers to a reaction pathway defined through analyzing experimental data to describe the state of the biosystem in whole or part. The data types that can be used to define phenomenological reaction pathways include but are not limited to transcriptomic, proteomic, metabolomic, fluxomic, protein-protein interaction, and DNA-binding site occupancy data. The data analysis methods used to define the phenomenological pathways from the experimental data include but are not limited to systems identification, statistical, algorithmic, or signal processing techniques.

Phenomenological information about the reactions and reactants of a biosystem can be determined by methods known in the art, and can be either qualitative or quantitative. For example, phenomenological information can be obtained by determining transcription of genes, expression or interactions of proteins, production of metabolites or other reactants, or use of reactions in the biosystem. By analogy to the term "genome," such information, when obtained at the scale of substantially the whole organism or cell, is called, respectively, the "transcriptome," "proteome," "metabolome" and "fluxome."

Methods of determining gene expression at the transcriptome scale (also known as "transcriptomics") are known in the art and include, for example, DNA microarray methods, which allow the simultaneous analysis of all transcripts simultaneously (Shena et al., Science 270:467-470 (1995); DeRisi et al., Science 278:680-686 (1997)) and serial analysis of gene expression (SAGE) methods (Velculescu et al., Trends Genet. 16:423-425 (2000)); Methods of determining protein expression (also known as "proteomics") are also known in the art. Expression proteomic methods generally involve separation of proteins, such as by two-dimensional gel electrophoresis, followed by protein imaging using radiolabels, dyes or stains. Separated proteins are then identified using methods such as peptide mass fingerprinting by mass spectrometry and peptide-sequence tag analysis by nano-electrospray (Blackstock et al., Trends Biotechnol. 17:121-127 (1999)).

Method for determining interactions between biological molecules in the cell at a large scale are also known in the art. Protein-protein interaction information, which allows inferences as to a protein's function, can be obtained, for example, using large-scale two-hybrid analysis to identify pairwise protein interactions (FromontRacine et al., Nat. Genet. 16:277-282 (1997). Indirect protein-DNA interaction information can be obtained using chromatin immunoprecipitation chip (ChIP-ChIP) methods, which allows the genome-scale identification of genomic binding sites of DNA-binding proteins and genomic targets of transcription factors (Iyer et al., Nature 409:533-538 (2001)).

Methods of determining the complement of metabolites in a cell (also known as "metabolomics") are also known in the art and include, for example, nuclear magnetic resonance (NMR) spectroscopy such as 13C-NMR; mass spectroscopy such as gas chromatography/time-of-flight mass spectroscopy (GC/TOFMS); and liquid chromatography (Fiehn, Plant Mol. Biol. 48:155-171 (2002); Phelps et al., Curr. Opin. Biotech. 13:20-24 (2002)).

Likewise, methods of measuring the fluxes through reaction pathways (also known as "fluxomics") are known in the art, such as metabolic flux ratio analysis (METAFoR) (Sauer et al., J. Bacteriol. 181:6679-6688 (1999)). METAFoR quantifies the relative abundance of intact carbon bonds in biomass constituents that originate from uniformly isotopically labeled precursor molecules, which reflects the metabolic pathways used.

By repeatedly varying the physiological state of the biosystem, either experimentally or in silico, a series of phenomenological measurements at different states can be obtained or predicted. These data can be organized in vectorial form and represented in matrix or tabular formats. For example, a set of gene array expression data can be organized as a matrix where each row is a gene, each column is an experiment, and each value is an expression level or ratio. As another example, a set of fluxome data can be organized as a matrix where each row is a reaction, each column is an experiment and each value is a flux level or ratio. As a further example, a set of phenotypic data can be organized as a matrix where each row is an experiment, each column is an environmental component (such as nutrients, waste products, or biomass) and each value is a rate of uptake, secretion, or growth.

The phenomenological information can be analyzed by various methods known in the art, such as methods of system identification, statistical data analysis, combinatorial algorithms, or signal processing to determine a set of phenomenological reaction pathways.

Methods of system identification are known in the art and include, for example, various types of clustering analysis methods (reviewed in Sherlock et al., Curr. Opin. Immunol. 12:201-205 (2000)). Clustering methods can be applied to experimental data in matrix or tabular formats to extract groups of genes that are co-expressed. These groups that can either be disjoint or overlapping can be used as definitions of phenomenological pathways. Alternatively, a data vector within each cluster can be chosen to be a representative phenomenological pathway for that cluster—this vector could for example be the mean value of the data points within the cluster also known as the centroid of the cluster.

Clustering analysis methods include, for example, hierarchical clustering analysis (Eisen et al., Proc. Natl. Acad. Sci. USA 95:14863-14868 (1998); Wen et al., Proc. Natl. Acad. Sci. USA 95:334-339 (1998)), whereby single reactant profiles are successively joined to form nodes, which are then joined further. The process continues until all individual profiles and nodes have been joined to form a single hierarchical tree. Clustering analysis methods also include divisive clustering analysis (Alon et al., Proc. Natl. Acad. Sci. USA 96:6745-6750 (1999)), in which two vectors are initialized randomly, and each reactant is assigned to one of the two vectors using a probability function. The vectors are iteratively recalculated to form the centroids of the two clusters, and each cluster is successively split in the same manner until each cluster consists of a single profile. Clustering analysis methods also include methods in which the data is partitioned into reasonably homogeneous groups. Clustering methods that incorporate partitioning include, for example, self-organizing maps (Kohenen, "Self Organizing Maps," Berlin: Springer (1995); Tamayo et al., Proc. Natl. Acad. Sci. USA 96:2907-2912 (1999)) and k-means clustering (Everitt, "Cluster Analysis 122," London: Heinemann (1974).

Another method of system identification is principal component analysis of the data, which is closely related to the singular value decomposition (SVD) of the data matrix (Holter et al., Proc. Natl. Acad. Sci. USA 97:8409-9414 (2000); Alter et al., Proc. Natl. Acad. Sci. USA 97:10101-10106 (2000); Holter et al., Proc. Natl. Acad. Sci. USA 98:1693-1698 (2001)). Principal component analysis is a statistical technique for determining the key variables in a multidimensional data set that explain the differences in the observations, and can be used to simplify the analysis and visualization of multidimensional data sets. SVD is a linear transformation of data, such as gene expression data, from genes×arrays space to reduced diagonalized "eigengenes"× "eigenarrays" space, where the eigengenes (or eigenarrays) are unique orthonormal superpositions of the genes (or arrays). After normalization and sorting of the data, the individual genes and arrays become grouped according to similar regulation and function, or similar physiological state, respectively. Principal component and SVD analysis output a set of vectors in the data space (e.g. n dimensional where n is the number of genes) ordered by how much of the variability in the data each vector each principal component or mode captures. These vectors can each be interpreted as phenomenological pathways describing the major modes of usage of the gene/protein complement of the organism under specific conditions that the experiments analyzed represent.

Software for various tyes of large-scale data analysis, including hierarchical clustering, self-organizing maps, K-means clustering and principal component analysis, is known in the art or can be developed for a particular application. Exemplary analysis software includes "Xcluster" (see genome on the World Wide Web at stanford.edu/sherlock/cluster.html), "Cluster" softare (see rana.lbl.gov/EisenSoftware.htm on the World Wide Web) and "Genesis" software (see genome.tugraz.at/Software/Genesis/Description.html on the World Wide Web).

The skilled person can determine which method, or which combination of methods, is suitable to analyze phenomenological information to determine a set of phenomenological reaction pathways.

As used herein, the term "operational reaction pathway" refers to a systemic reaction pathway of a biosystem that is feasible taking into account the reactants present in, or fluxes through, the biosystem. Operational reaction pathways thus constitute a subset of systemic reaction pathways that are likely to actually exhibit flux in the biosystem. The subset of systemic pathways that are consistent with phenomenological information about the biosystem are determined to identify operational reaction pathways consistent with the reactants present or reaction fluxes through the biosystem.

Once a set of systemic reaction pathways and a set of phenomenological reaction pathways have been provided, the two sets are compared, and common pathways identified. As described above, the two sets of pathways can be represented in vectorial form, or in the form of groups of genes participating in the pathways, or in other convenient ways. There are a number of mathematical methods known in the art by which two vectors or two groupings can be compared.

For example, the two sets of vectors can be compared using a number of measures for pairwise similarity between vectors including: (1) Euclidean distance, which corresponds to the squared distance between two points in space, or in this case two vectors, taking into account both the direction and the magnitude of the vectors (Hubbard J. H. and Hubbard B. B. Vector Calculus, Linear Algebra, and Differential Forms, Prentice-Hall (1999)); (2) Pearson correlation coefficient, which measures the angle between two vectors whose length is normalized to one, and is thus independent of the length of the vectors (Larsen R. J. and Marx M. L. An Introduction to Mathematical Statistics and Applications, Prentice Hall, New Jersey (1986)); or (3) Jackknife correlation coefficient, which is similar to Pearson correlation coefficient, but is corrected for the effect of single outliers components of the vectors to provide a more robust distance measure (Heyer et al., Genome Res. 9:1106-1115 (1999)). Other methods for comparing vectors are known in the art.

Similarly, methods for comparing groupings of genes based on systemic and phenomenological definitions include: (1) the Rand index, which measures the overlap between two different groupings of the same set of genes (Yeung K. Y et al. Bioinformatics 17:177 (2001)); and (2) correspondence analysis, which provides a two-dimensional graphical representation of the agreement between two groupings such that the systemic and phenomenological pathways that are most similar to each other are shown to be located closest to each other (Johnson R. A. and Wichem D. W. Applied Multivariate Statistical Analysis, 5th Ed., Prentice Hall, New Jersey (2002)).

The skilled person can determine which method, or which combination of methods, is suitable for comparing systemic reaction pathways and phenomenological reaction pathways to identify operational reaction pathways.

The invention also provides a method determining the effect of a genetic polymorphism on whole cell function. The method consists of: (a) generating a reaction network representing a biosystem with a genetic polymorphism-mediated pathology; (b) applying a biochemical or physiological condition stressing a physiological state of the reaction network, and (c) determining a sensitivity to the applied biochemical or physiological condition in the stressed physiological state compared to a reaction network representing a normal biosystem, wherein the sensitivity is indicative of a phenotypic consequence of the genetic polymorphism-mediated pathology. The biochemical or physiological condition can be, for example, a change in flux load, pH, reactants, or products as well as system or subsystem changes such as those in oxidative or energy load.

Briefly, the above methods for analyzing physiological states of a biosystem, comparing them to systemic reaction pathways and determining one or more operational reaction pathways can similarly be employed to determine the effect of genetic polymorphisms on a biosystem or subcomponent thereof. For example, phenomenological information used for comparison with systemic reactions can be obtained from either actual or simulated genetic mutations of enzymes or other polypeptides. Changes in activity of the enzyme or polypeptide due to the mutation can be obtained from sources describing the defect or estimated based on available information or predictive computations using a variety of methods well known in the art. The activities that can be assessed include, for example, catalytic function of an enzyme or binding activity of a polypeptide such as a transcription regulator.

In silico models constituting a reaction network of a genetic polymorphism can be constructed as described previously and the effect of the polymorphism can be assessed in context of the biosystem as a whole. Conditions that the reaction network are subjected to can be varied and the effect of single or multiple, combined polymorphisms can be determined on whole biosystem function or as the polymorphism relates to subsystems thereof. For example, systemic pathways or operational pathways can be calculated in the presence or absence of the genetic polymorphism. Comparision of systemic pathways, operational pathways or a phenotypic manifestation between the two reaction networks can be performed to determine the differences, if any, between the native reaction network and the polymorphic counterpart. Such differences can include, for example, creation of a new systemic or operational pathway, omission of such a pathway and changes in the rate or magnitude of such a pathway. The result of such changes between the normal and polymorphic states also will reveal the consequential impact on biochemical or physiological function or on phenotypic expression of the genetic polymorphism.

Conditions that can be varied include, for example, any biochemical or physiological component of the system. Such conditions can be either external to the biosystem including, for example, external environmental growth conditions such as temperature, pH, carbon source and other input/output reactions which allow components to enter or exit the biosystem. Alternatively, such biochemical or physiological conditions can be internal to the biosystem. Specific examples of internal conditions include, for example, exchange reactions indicative of sources and sinks allowing passage of reactants across a system or subsystem boundary, intrasystem reactions that replenish or drain reactants, and demand reactions which represent categories of components produced by the cell. Biochemical or physiological conditions internal to the biosystem also can include changes in pH, utilization of carbon sources, availability of metabolites, cofactors, substrates and products. Other changed internal conditions can include, for example, alterations in system loads such as oxidative or energy load on its corresponding subsystem. Various other biochemical or physiological conditions well known to those skilled in the art can similarly be varied in the methods of the invention to obtain comparative reaction network simulations for determining the effect of a genetic polymorphism on biosystem function.

Altering or changing a condition for each biosystem will generally be sufficient for a comparison between a native and a counterpart polymorhic biosystem. However, the effect can be enhanced when the biochemical or physiological condition is applied to the native and polymorphic biosystem at a magnitude sufficient to stress the biosystem or a correlative subsystem thereof. For example, where the activity of a polymorphic enzyme is altered only slightly compared to its native counterpart, the difference in activity may not substantially affect cellular function within an activity range tested. In part, an insignificant impact on cellular function can be due to the production of sufficient product to perform normal cellular activity regardless of an activity deficiency. However, where the activity of the polymorphic enzyme is tested under stressed conditions, it can be unable to fulfill the added cellular demand due to the additional work required of the system. Accordingly, under stressed conditions, a comparison of the native reaction network functioning and that of the polymorphic reaction network will more readily reveal those activity effects of the polymorphic enzyme due to failure of product production under excess requirements.

The term "stress" or "stressing" as used in reference to applying a biochemical or physiological condition is intended to mean placing a biosystem, reaction network or subsystem thereof under a state of strain or influence of extra effort. The stress can be mild or intense so long as it applies demands, loads or effort on the components extra to that under the normal or nominal state of the biosystem, reaction network or subsystem thereof. Therefore, stressing a system state is intended to include imposing a condition that causes the system to exert additional effort toward achieving a goal. Specific examples of applying a biochemical or physiological condition to a biosystem that stresses a physiological state is described further below in Example III.

Genetic polymorphisms can constitute, for example, single nucleotide polymorphisms (SNPs) and well as multiple changes within a encoding gene resulting in a polymorphic region within the gene or its polypeptide coding region. Polymorphisms in gene or coding region structure can alter the expression levels of the harboring nucleic acid, activity of the encoded polypeptide or both. Polymorphisms well known to those skilled in the art of genetics and genomics include, for example, allelic variants of genes, SNPs and polymorphic regions of a referenced nucleic acid. Specific examples, of genetic polymorphisms include those variations in coding sequence described in Example III for glucose-6-phosphate dehydrogenase (G6PD) and pyruvate kinase (PK). Numerous other genetic polymorphisms and their associated diseases are similarly well known to those skilled in the art.

Given the teachings and guidance provided herein, the methods of the invention for determining the effect of a genetic polymorphism on cellular function can be used with any known or subsequently determined genetic polymorphism. Similarly, the linkage between the genetic defect and the pathology mediated also can be previously known or subsequently determined. Moreover, and as described further below, it can be used to diagnose previously undetermined genetic polymorphisms that alter an activity of an enzyme or polypeptide. However, by determining the effect of the defect in the context of a whole biosystem, a more accurate phenotype and assessment of the functional abilities of the biosystem can be obtained. Accurate determination of phenotypic and functional attributes of such complicated systems can be advantageously applied for a more meaningful treatment of the genetic polymorphism-mediated disease.

Sensitivities of the polymorphic enzyme to the stressed condition can be more or less pronounced depending on which polymorphisim is incorporated into the reaction system, the degree of polypeptide activity change due to the polymorphism and the level of stress that is exerted on the system. Those skilled in the art will know or can determine, given the teachings and guidance provided herein, what sensitivities are indicative of a particular polymorphic enzyme or other polypeptide. For example, glucoso-6-phosphate dehydrogenase (G6PD) functions in the oxidative branch of the pentose pathway and is sensitive to changes in maximum velocity ($V_{max}$) and cofactor binding affinity ($K_{i\text{-}NADPH}$). Enzymes with alterations in these activities result in changed in oxidative requirements which can be used as indicators of the metabolic state for G6PD's having altered activity. For example, one sensitive indicator of the metabolic state of the biosystem is the NADPH/NADP ratio. This ratio can be measured under stressed conditions and compared between the polymorphic reaction network with that of the normal network to determine the phenotypic and functional changes on the biosystem. As described further below in Example III, polymorphic enzymes having alterations in these G6PD activities can be distinguished in the methods of the invention as those mediating non-chronic and chronic hemolytic anemia.

Similarly, pyruvate kinase (PK) functions in glycolysis and is sensitive to changes in $V_{max}$ and the affinity for substrates such as phosphoenolpyruvate ($K_{PEP}$). Alterations in these activities result in changes in ATP concentration, and 2,3 DPG concentration. Sensitive indicators of $V_{max}$ and $K_{PEP}$ can include, for example, the concentration of ATP when the biosystem is under maximum energy loads or stress compared to normal conditions. As with G6PD, polymorphic PK enzymes having alterations in these activities show that anemic patients have a diminished ability to deviate from the normal homeostatic state.

For determining the effect on function, a reaction network specifying the activity of the polymorphic enzyme is constructed and the system is stressed as described above. Sensitivity to the stressed condition compared to that of the normal or native reaction network can then be determined using a variety of indicators. Those described above for G6PD and PK are exemplary indicators for enzyme activity. Those skilled in the art will understand, given the teachings and guidance provided herein that other indicators of biochemical or physiological activity of the particular enzyme or polypeptide being assessed can be used in the methods of the invention. For example, essentially any measure of substrate, product, cofactor, or other metabolite can be used as an indicator of polypeptide activity. Such indicators can be assessed directly or indirectly such as by measuring the products of downstream reactions and the like. Moreover, ratios of such indicators or of general indicators of a particular biochemical or physiological state can similarly be used. For example, ATP, and energy cofactors such as NADPH and NADP are general indicators of the oxidative state and energy charge, respectively, of a biosystem.

Changes in activity under stressed conditions of such biochemical or physiological indicators will identify the change in function of the biosystem due to the altered activity as well as show the phenotypic consequences of the polymorphic enzyme. For example, the inability of a biosystem to respond to excess oxidative or energy requirements can show, for example, that the polymorphic enzyme is unable to adequately produce components within its assigned subsystem to handle the increased work requirements caused by the stress. A functional biosystem change can correspond to, for example, altered demands and products that are produced as well as changes in flux or pathways which compensate the deficient enzyme activity. A phenotypic outcome can be, for example, inhibition of biosystem proliferation, decrease in biosystem mass or even biosystem lysis and death.

The methods of the invention also can be used for diagnosis of a genetic polymorphism-mediated pathology. The methods described above can be used to generate a biosystem reaction network representing activities of suspected genetic polymorphism. The biosystem reaction network can be stressed as described above and the reaction network containing the suspected polymorphic enzyme activity compared to that of a normal reaction network. A change in function or phenotype of the suspected polymorphic network compared to the normal will indicate that the genetic alteration is linked to the enzyme deficiency. Those skilled in the art will understand that a plurality of suspected enzyme defects can be identified and linked to a particular disease given the teachings and guidance provided herein. For example, those skilled in the art can use activity measurements from a suspected patient in the creation of a plurality of reaction networks. Comparison of the function or phenotype of the networks harboring suspect activities with normal networks will identify the differences in function or phenotype and whether any of such identified differences are sufficient to result in a pathological condition.

Therefore, the invention provides a method of diagnosing a genetic polymorphism-mediated pathology. The method consists of: (a) applying a biochemical or physiological condition stressing a physiological state of a reaction network representing a biosystem with a genetic polymorphism-mediated pathology, the applied biochemical or physiological condition correlating with the genetic polymorphism-mediated pathology, and (b) measuring one or more biochemical or physiological indicators of the pathology within the reaction network, wherein a change in the one or more biochemical or physiological indicators in the stressed state compared to an unstressed physiological state indicates the presence of a genetic polymorphism corresponding to the pathology.

The invention further provides a method of reconciling biosystem data sets. The method consists of: (a) providing a first regulatory network reconstructed from legacy data comprising a plurality of hierarchical regulatory events; (b) providing a second regulatory network obtained from empirical data, and (c) determining a consistency measure between the hierarchical regulatory events in the first regulatory network and elements in the second regulatory network, wherein a high degree of the consistency measure for the hierarchical regulatory events indicates the validity of the first regulatory network or a subcomponent thereof.

The method of the invention for reconciling data sets is useful for determining the accuracy of a biosystem model as well as for identifying new components, linkages, networks and subnetwork of a biosystem model. The model can be based on scientifically proven data, mathematical interpretations as well as on pure computational analysis or even theoretical prediction. Regardless of the source of a biosystem model, the method for reconciling data sets compares the model or a data set representation thereof to another source of data to identify the consistency between one model or data set and that of the comparison model or data set. The degree of consistency between the two models or data sets thereof will show how accurate the initial model is to its corresponding natural biosystem.

Data sets representing whole biosystems can be reconciled using the methods of the invention as well as any substructure thereof. Substructures can consist of subnetworks or modules of the biosystem reaction network. While the exact boundaries of subnetworks and boundaries can vary depending on the assessment criteria used, one feature is that such substructures can be evaluated, analyzed or identified as a unit in itself. Criteria for boundary determination can include, for example, functional attributes, structural attributes and graphical or mathematical separateness, for example. Specific examples of subnetworks or modules of a biosystem have been described above and below and are further shown in FIG. 16 and its associated Example IV. Other examples are well known to those skilled in the art and can be employed in the methods of the invention given the teachings provided herein.

Data sets applicable for comparison can include a broad range of different types and sizes. For example, the data sets can contain a large and complex number of diverse data elements or components of the reaction network. Alternatively, the data sets can be small and relatively simple such as when comparing subnetworks or modules of the reaction network. Those skilled in the art will appreciate that the more inclusive each data set for comparison is with respect to its system components, the more accurate and reliable will be the consistency measure. However, those skilled in the art will know, or can determine, a reliable means to compensate for inherent differences based on the character of one or both of the initial data sets. Therefore, the method of the invention can be used for reconciling data sets where the pair of data sets for comparison can be either large or small, or diverse or simple, as well as for comparison where the data sets within the pair are either large or small, or diverse or simple with respect to each other.

As used herein, the term "legacy" or "legacy data" is intended to refer to known information or data such as that obtainable from literature, other reports, computational data, databases or a combination thereof. The information can be obtained from the public domain or previously known by the user's own investigations. The term therefore is intended to include secondary data that has received the benefit of scientific evaluation and considerations toward the system to which it pertains, the scientific authenticity or the theory which it promotes. Legacy data in essentially any obtainable form can be used in the methods of the invention and can include, for example, literary, graphical, electronic, mathematical or computational forms as well as functional equivalents and transformations thereof. Given the teachings and guidance provided herein, those skilled in the art will known how to use a particular format either directly or following transformation into a useful format for representing a reaction network of the invention. A variety of such useful formats have been described above and below and others are well known to those skilled in the art.

As used herein, the term "empirical" or "empirical data" refers to data based on primary factual information, observation, or direct sense experience. Empirical data is therefore intended to refer to raw data or primary data that has not received the benefit of scientific evaluation and considerations toward the system to which it pertains, the scientific authenticity or the theory which it promotes. The term is intended to include, for example, data, data sets or equivalent transformational forms thereof corresponding to gene expression data, protein activity data and the like. It can include, for example, large, high throughput datasets such as that obtainable by genomic, proteomic, transcriptomic, metabolic and fluxomic data acquisition as well as small data sets obtainable by a variety of research methods well known to those skilled in the art. Other forms of primary data well known to those skilled in the art can similarly be employed in the methods of the invention.

Useful attributes of reconciling data sets include, for example, both validation of known reaction network and subnetwork models as well as the identification or discovery of new subnetworks or modules thereof. Validation of an existing model is useful in itself because it authenticates previous scientific theories as well as subsequent discoveries based on the original model. Similarly, invalidation of a network model can be useful, for example, because it informs the user that components, links or scientific premises may be omitted from the network model as a whole. Moreover, reconciliation of data sets can identify subnetworks or modules of the biosystem reaction network model by showing differential validation of a particular subsystem or of several subsystems within the whole. For example, discovery of new subnetworks or identification of valid subnetworks within the whole can occur when some, but not all, modules within the biosystem network are reconciled. Identifications are particularly striking where the subnetwork or module thereof constitute relatively independent entities within the biosystem reaction network or are relatively decoupled from the body of the biosystem network. Finally, information gained from reconciliation of data sets and validation of whole networks, subnetworks or modules thereof can be used to refine the network or subnetworks by altering the model determining whether the altered model reconciles with the comparative data set.

Validation and discovery methods of the invention are applicable to essentially any form or format of the reaction network. For example, data sets can be reconciled where a reaction network is represented by an in silico model, a mathematical representation thereof, a statistical representation, computational representation, graphical representation or any of a variety of other formats-well known to those skilled in the art.

Reconciliation of data sets allows for the validation of essentially any causal relationships within the compared biosystem networks. For example, the method for reconciliation of data sets can be employed on data sets specifying all types of reaction networks described herein. Therefore, the method is applicable to reaction networks corresponding to a metabolic reaction network, a regulatory reaction network, a transcriptional reaction network or a genome-scale reaction network, or any combination thereof. To perform the method of reconciliation, a first reaction network can be provided that is reconstructed from legacy data. As described previously, the legacy data can be obtained from a secondary source that has assembled primary data into a working model of the biosystem network components. The first reaction network is compared with a second reaction network obtained from empirical data. The empirical data can consist of, for example, any primary data representing an activity or other attribute of the components within the biosystem.

A comparison of data sets can be accomplished by, for example, any method known to those skilled in the art that provides a measure of consistency between the network representation and the empirical data. In one embodiment a consistency measure is determined between the empirical data and the legacy data, or the legacy-derived network model by, for example, grouping the network components into hierarchical organization of reaction categories. The reaction categories are useful for determining consistency measurements between the data sets to be reconciled. The reaction categories can include, for example, reactants and products, reaction fluxes, metabolic reactions, regulatory reactions and regulatory events. Moreover, the reaction categories can be arbitrary, or based on, for example, functional criteria, statistical criteria, or molecular associations so long as the categories provide an acceptable framework for obtaining a consistency measure between the legacy-derived network and the empirical data set.

Exemplary reaction categories for the specific embodiment of a regulatory reaction network are described further below in Example IV. Briefly, elements of a regulatory network can be separated into, for example, three categories based on functional interactions. These categories include, for example, pair-wise regulatory interactions, target-regulator units and regulons. Given the teachings and guidance provided herein, categories other than these for regulatory networks as well as categories for other types of reaction networks can be identified or generated by those skilled in the art. For example, other types of categories can include anabolic or catabolic reactions or cell signaling functions. The particular type of category will depend on the type of reaction network to be reconciled and the measure of consistency selected to be used in the method of the invention.

Consistency of the data sets to be reconciled can be determined by a variety of methods well known to those skilled in the art. Such methods can be employed to generate a value for each of category or element within a network that can be analyzed for significance. For example, in the above exemplary reaction categories, consistency measurements for pair-wise interactions can be obtained, for example, by Pearson correlation coefficients whereas consistency measurements for target-regulator units can be determined by, for example, multiple correlation coefficients. Further, consistency measurements for regulons can be determined by, for example, the average within regulon correlation. Other methods well known in the art also can be employed and include, for example, mutual information-based measures (Cover T M & Thomas J A. Elements of Information Theory, Wiley (1991)), or nonlinear regression methods (Hastie T, Thibshirani R & Friedman J. The Elements of Statistical Learning, Springer (2001)). The mutual information measures require discretization of the original data, but allow incorporating nonlinear dependencies that are not accounted for by Pearson or multiple correlation coefficients. Similarly non-linear correlation measures can be used as consistency metrics, but their added flexibility compared to linear correlation may result in overestimating the consistency between empirical data and a proposed network structure. The statistical significance of particular values of a consistency measure can be determined to assess whether the legacy data and empirical data constitute a good fit. A high degree of consistency measure, such as those that are statistically significant, indicate that the two networks, subnetworks or subcomonents reconcile. Further, those data sets that reconcile either as to the whole network or a subnetwork thereof indicate a validation of the legacy model whereas those that are inconsistent indicate a divergence between the legacy-derived model and the empirical data.

The invention further provides a method of refining a biosystem reaction network. The method consists of: (a) providing a mathematical representation of a biosystem; (b) determining differences between observed behavior of a biosystem and in silico behavior of the mathematical representation of the biosystem under similar conditions; (c) modifying a structure of the mathematical representation of the biosystem; (d) determining differences between the observed behavior of the biosystem and in silico behavior of the modified mathematical representation of the biosystem under similar conditions, and (e) repeating steps (d) and (e) until behavioral differences are minimized, wherein satisfaction of a predetermined accuracy criteria indicates an improvement in the biosystem reaction network.

The method can further include the steps of: (f) determining a behavior of the biosystem under different conditions, and (g) repeating steps (b) through (e) of the method for refining a biosystem reaction network under the different conditions. The method for refining a biosystem reaction network can additionally include repeating steps (f) and (g) until the minimized behavioral differences are exhausted, wherein the improved biosystem reaction network representing an optimal biosystem reaction network.

Figure 2B:
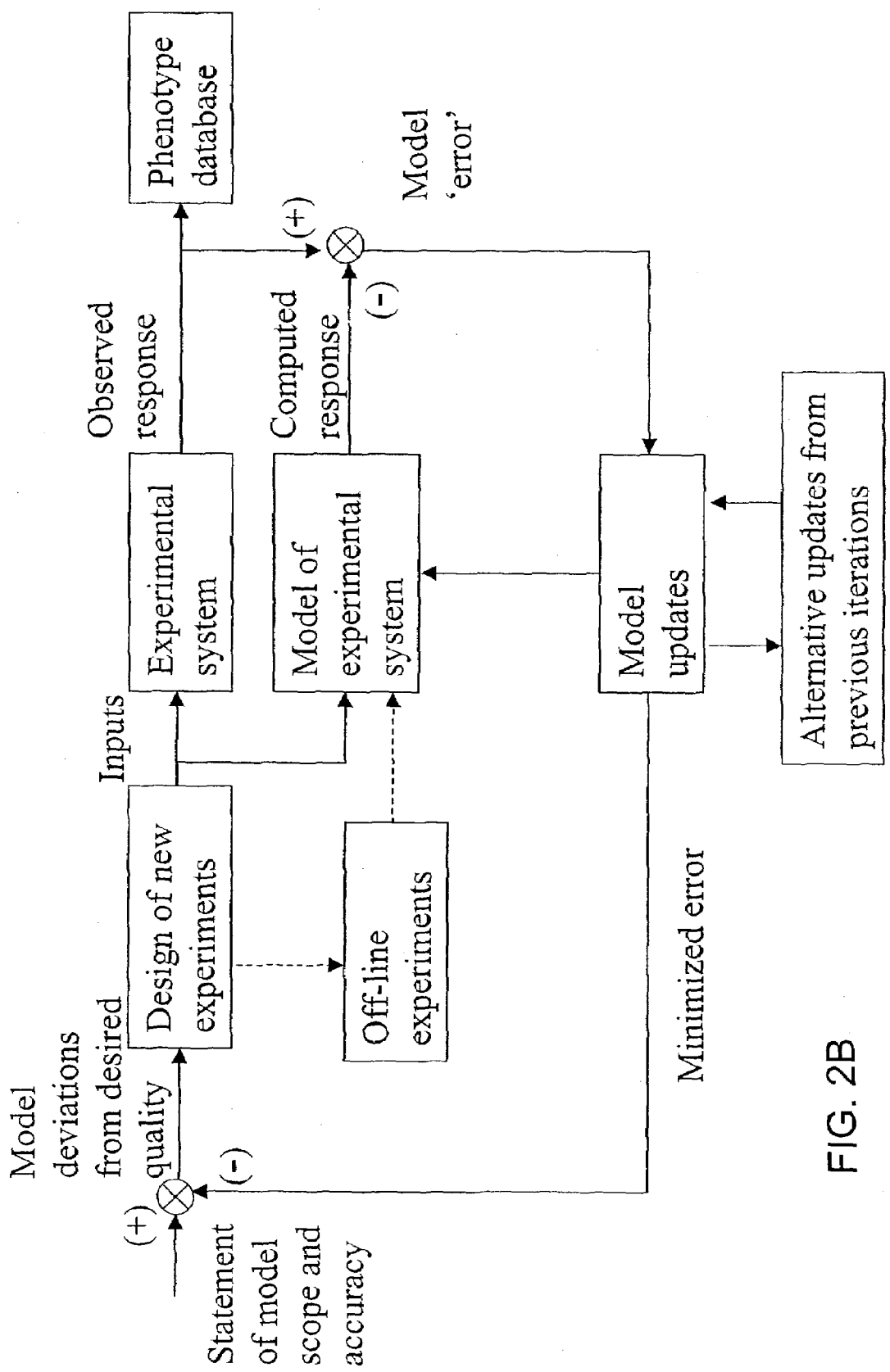
FIG. 2b shows a process by which mathematical representations of biosystems can be improved in an iterative fashion using algorithmic approaches and targeted experimentation.

The methods of the invention can also be applied in a general process by which mathematical representations of biosystems can be improved in an iterative fashion using algorithmic approaches and targeted experimentation. Many biological systems are incompletely characterized and additional experimentation can be required to reconstruct a reaction network of these systems. For such a process to converge quickly on an optimal model, an iterative experimentation can be systematized. FIG. 2b exemplifies such a procedure, which is further described in Example V.

The model building process can begin with a statement of model scope and accuracy. Alternatively, the model building process can proceed in the absence of such a predetermined assessment of scope or accuracy but terminated once a desired scope or accuracy is ultimately obtained.

The purpose for building the model leads to specification of expected accuracy and the scope of capabilities that the model is to have. The scope of a model can range from, for example, describing a single pathway to a genome-scale description of a wild type strain of an organism. An even broader scope would be to include sequence variations and thus insist that a model describes all the variants of the wild type strain.

The accuracy can be based on, for example, qualitative or quantitative criteria. A useful model can be qualitative and be able to make statements that predict, for example, that the growth rate of an organism is reduced when a particular gene product is inhibited under a particular growth condition. A quantitative model can insist, within measurement error, on predicting the percent reduction in growth rate of inhibition of all the gene products under one or more growth conditions. The extent of the iterative model-building process is therefore dictated and predetermined by the user who can specify a required scope and accuracy of the model to be generated.

A reconstructed biochemical reaction network can be envisioned as a model of an experimental system. In this regard, it is a duplicate of an actual organism that is capable of flexible manipulation and study under any conditions that is desirable to subject the actual organism to. One advantage of a reconstructed biosystem reaction network, or an in silico version thereof, is that it is capable of generating an immense amount of information that characterizes the function and phenotype of the organism. The accuracy of the in silico model can also be determined by, for example, using the methods described above for reconciliation and determining the consistency of the reconstructed network with that of empirical data obtained from the actual organism. The availability of both an actual organism and a reconstructed model of the organism that is readily manipulable can be used synergistically to harness the power of in silico models for reliable and accurate predictions of organism behavior and function.

An approach to reconstructing an in silico model of a biosystem is through iterative refinement of a biochemical reaction network. The refinement of a model can be accomplished by assessing a particular function of the actual organism and incorporating into the model new information gained from that particular study. Because the model is an duplicate of the organism, deviations in performance from the model compared to the actual organism when performed under similar conditions will yield data indicating that additions, omissions or revisions to the in silico that can account for the deviations. By successive iterations of studies duplicating conditions that the actual and in silico organisms are subjected to, altering the model structure to correct and be consistent with the empirical data obtained from the actual organism and repeating the condition or subjecting the pair to different conditions, the accuracy of the model to predict function and phenotype of the actual organism will successively increase.

Briefly, studies can be performed with the actual organism under defined conditions prescribed by an experiment design algorithm. Similarly, the in silico model that describes the actual organism can be used to simulate the behavior of the actual organism under the same conditions. Based on the available data at any given time, if the model fails to meet the desired scope or accuracy requirements, further studies can be performed to improve the model. These studies can be designed using, for example, a systematic procedure to stepwise or incrementally probe network function. One approach to probe network function can be, for example, to incrementally move from a robust or validated subsystem of the network to less validated parts. Another approach can be, for example, to target different types functions or different types of methods for probing function. Particular examples of such targeted methods of study include, for example, genomic knock-outs, expression profiling, protein-protein interactions, and the like. Therefore, the content and capabilities of the in silico model are subject to iterative updates.

The decision on what experiments to perform can be determined, for example, based on the nature of the deviation and the requirements in an accuracy specification. Deviations can include a gene expression array that is not predicted correctly by the model, a set of calculated flux values which does not match the experimentally-determined fluxome under given conditions, or a set of phenotypes, for example, growth, secretion and/or uptake rates, which shows discrepancy from model predictions. Experiments which could be performed to resolve such discrepancies include perturbation analysis wherein one or more genes thought to be responsible for the discrepancy are knocked out, upon which the resulting organism is characterized using transcriptomics, fluxomics and the like, or environmental analysis wherein one or more component of the extracellular environment thought to contribute to model deviations is removed and the system is re-characterized.

Algorithms can be devised that design such experiments automatically. An algorithm which can be used in the case of gene expression can be, for example (1) determine the gene(s) which exhibit a discrepancy from the predictions of the model, (2) use the regulatory network model to identify the regulatory protein(s) which control the gene(s) in step (1), (3) knockout one or more genes in the organism which encode one or more regulatory proteins (4) perform the same transcriptome experiment under the same environmental conditions but with the new knockout strain. A second such algorithm which could be used in the case of a high-throughput phenotype study with a reconstructed metabolic network could be (1) determine the phenotype(s) which exhibit discrepancy (e.g., growth rates do not correlate), (2) systematically add all biochemical reactions, one or more at a time, until the model prediction matches the observed phenotype(s), (3) identify gene locus/loci with significant sequence similarity to identified enzymes which catalyze the reaction(s) in step (2), (4) clone and characterize the gene in step (3) to verify whether it can catalyze the predicted reaction(s). The inputs into an algorithm are several, including the present model, the data that it has been tested against, the magnitude and nature of deviations, and so forth. The output from the algorithm can be component experiments of whole organism experiments.

An algorithm can identify, for example, missing components in the model and request that specific biochemical, protein-DNA binding, protein-protein interaction, or enzyme kinetic activity experiments be performed. As described above, the missing components in the two above examples would be regulatory interactions and identified enzymes. If these studies reveal missing components of the model appropriate model updates are performed.

An algorithm can be facilitated by, for example, the inclusion of additional data from whole cell behavior. It may request that growth, transcription profiling, metabolic profiling, DNA-transcription factor binding state, or proteomic experiments be performed under one or more environmental conditions in order to obtain sufficient information to allow model updating.

Given a set of inputs such as gene deletions or environmental inputs, the response of the biochemical reaction network can be examined both actually and computationally. The actual system will yield an observed response characterized through phenomenological pathways of the system, while the model of the actual system will predict a response characterized by the systemic pathways of the system. The observed and computed responses can be compared to identify operational pathways as described previously. The difference in the measured and computed cellular functions under the defined conditions where the experiment is performed can be characterized, for example, as an "error". This difference corresponds to those systemic pathways that are not operational. The error can then be used to update the model.

Model update also can be accomplished by, for example, using an algorithm for updating parameters in the model so that the model error is minimized. As identified in Example VI, an algorithm for characterization of a regulatory network can be, for example, (1) obtain the activity of each protein as predicted by the model, (2) for each protein, generate a rule based on the activity of the given protein which results in the correct expression value for T5a, (3) recalculate the overall expression array for the regulated genes, (4) evaluate the difference between the criterion for model accuracy by determining the new model error, and (5) choose the model(s) with the lowest error as the new model for future iterations. Following optimal model updates are implemented, the remaining "error" between corrected model predictions and actual responses can be used to design new studies to further probe the system. The process can be repeated, for example, one or more times to further update the model based on these new studies and until a desired scope or accuracy is obtained.

Model updates that can minimize error on a round of the iterative reconstruction process can be non-unique or very similar to each other in generating optimal model updates. To preserve the availability of such data and increase the efficiency of subsequent rounds, alternative model updates can be stored, for example, so that they capable of being retrieved and available for subsequent use on further rounds of iterative model building. Additionally, a collection of experimental outcomes can be stored as a historic record of the behavioral data or phenotypic data that has been obtained on a particular organism. Model updates and design algorithms can be optionally capable of querying this database during execution. Various other records and system data can be alternatively stored for later efficient utilization in one or more steps of the iterative process. Such computational approaches are well known in the art and can be routinely implemented given the teachings and guidance provided herein.

Further, combinations and permutations of the various methods of the invention can be combined in any desired fashion to facilitate the model building process or to augment a purpose or implementation of the method. Additionally, single or other "off-line" studies can be performed and the information generated used in any of the methods of the invention to facilitate, augment or optimize results or implementation. For example, in addition to studies designed for the iterative process, in some cases specific pair-wise interactions among molecules can be probed in separate off-line studies to further characterize individual molecular components.

Advantageous properties of the iterative model-building procedure include convergence of system components into an operative and optimal representation of the actual organism and efficiency of constructing such a model. Efficiency in convergence is important since it will minimize the number of studies that need to be performed.

The following examples are intended to illustrate but not limit the present invention.

EXAMPLE I

Decomposing a Set of Phenomenological Flux Distributions for the *E. Coli* Core Metabolic Network in Order to Identify Operational Extreme Pathways This example shows how a set of phenomenological pathways (flux distributions) can be decomposed into dominant modes these modes can be compared with a set of systemic pathways (extreme pathways) to identify operational reaction pathways of a metabolic reaction network (*E. coli* core metabolism).

An in silico-generated metabolic flux profile of core metabolism in *E. coli* was prepared. The reactions were taken from table 6.3 of Schilling, "On Systems Biology and the Pathway Analysis of Metabolic Networks," Department of Bioengineering, University of California, San Diego: La Jolla. p. 198-241 (2000), with the exception that reaction pntAB was not included, and instead of T3P2 in reaction tktA2, T3P1 was used. The reaction list is tabulated in Table 1.

Figure 3:
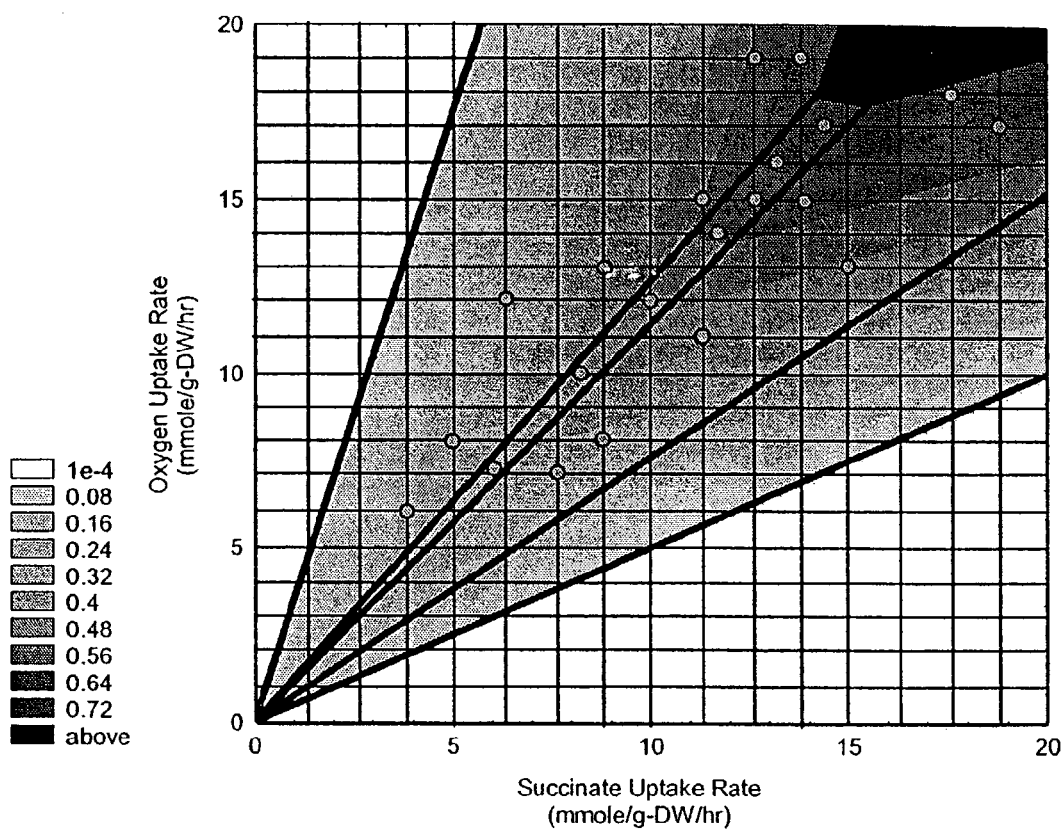
FIG. 3 shows a phase plane for succinate for an in silico-generated metabolic flux profile of core metabolism in E. coli was prepared.

The flux profile, which is the input matrix for Singular Value Decomposition (SVD) analysis, consists of 57 fluxes (rows) and 7 conditions in each phase (columns). The phase plane for succinate for this system is presented in FIG. 3; generation of Phase Planes is described in (Edwards J S, Ramakrishna R, Palsson B O. Characterizing the metabolic phenotype: a phenotype phase plane analysis. Biotechnol Bioeng. 2002 January 5;77(1):27-36). The points on FIG. 3 were chosen to define the upper limit of oxygen and succinate available to the system. Each point, therefore, represents a different condition (or column of the flux matrix) in constructing the flux profile.

SVD analysis was performed on each phase (each of the 7 conditions) separately. The decomposition of the flux matrix, A, results in three distinct matrices U (the left singular matrix), $\in$ (singular value matrix), and V (right singular matrix):

$$A = U \cdot \in \cdot VT$$

Figure 4:
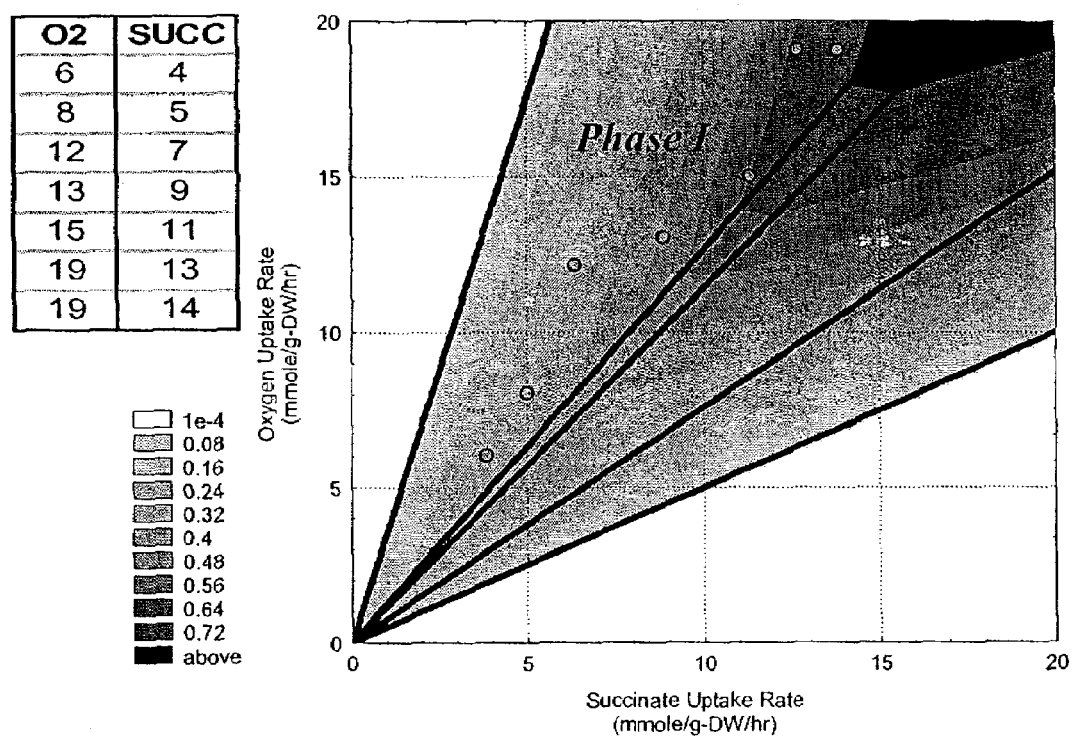
FIG. 4 shows phase I of a phase plane for a flux distribution matrix generated with the E. coli core metabolism using the oxygen and succinate input values show next to the figure.

For phase I of the phase plane, the flux distribution matrix was generated with the *E. coli* core metabolism using the oxygen and succinate input values that are tabulated next to FIG. 4. The points lie on phase I as shown.

Figure 5:
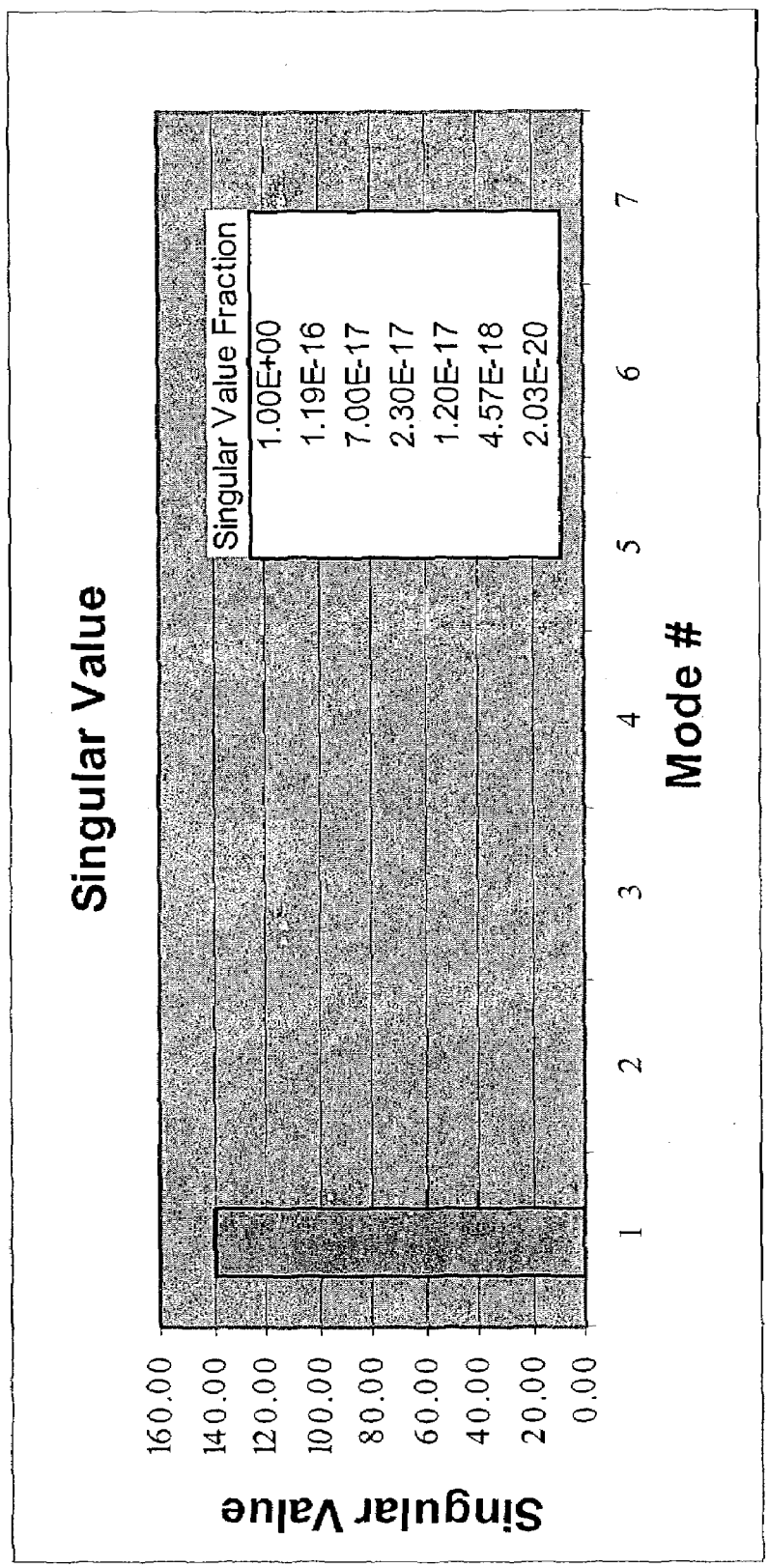
FIG. 5 shows an Singular Value Decomposition (SVD) analysis on the flux matrix shown in FIG. 4.

SVD analysis on the flux matrix revealed that there is only one dominant mode in phase I as demonstrated by the singular value fractions shown in FIG. 5. Therefore, there is a common expression that dominates nearly all of the system's behavior in this phenotypic phase, which can be called a phase invariant singular value.

Figure 6:
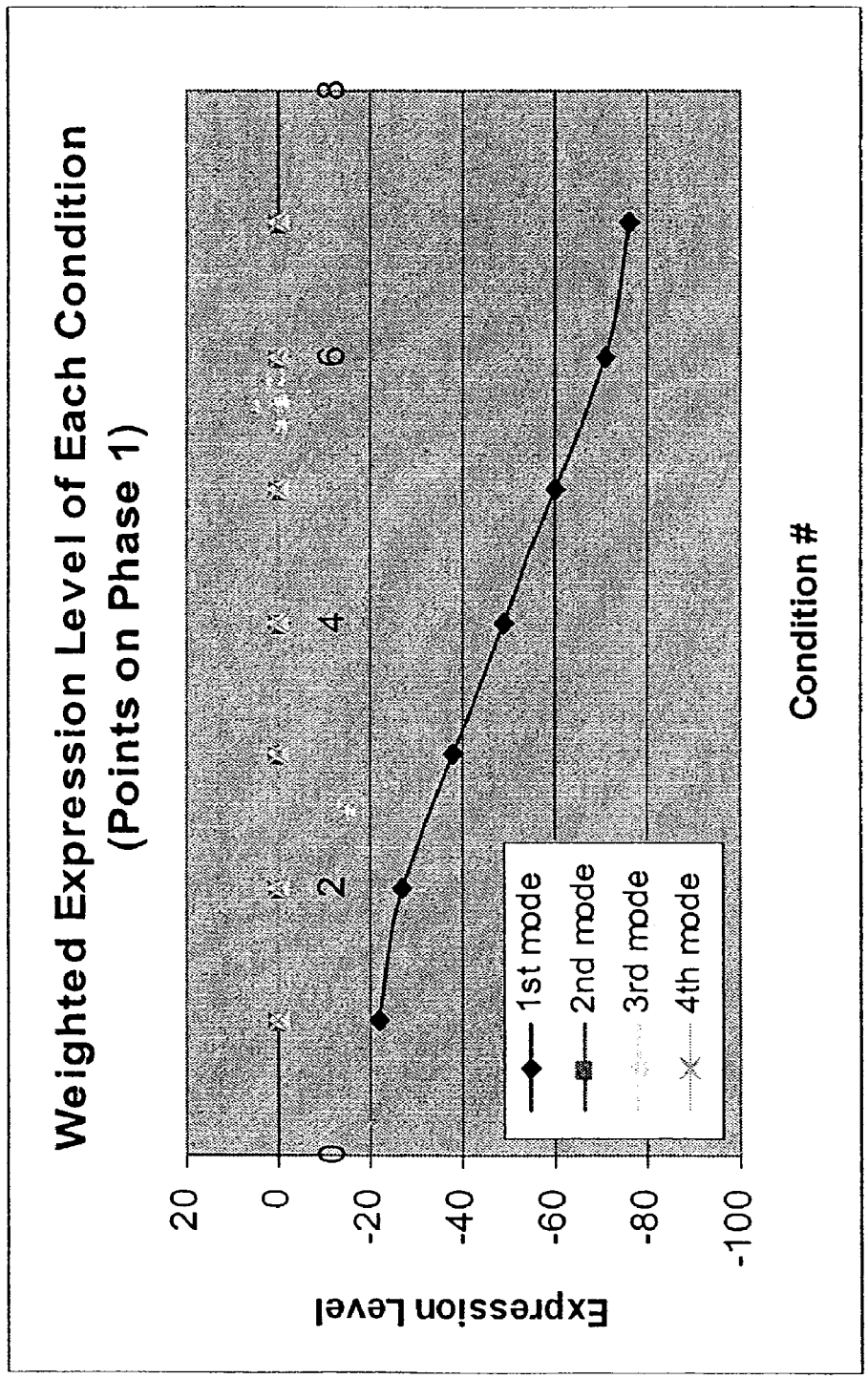
FIG. 6 shows the contribution level of each condition, or point shown in phase I of the FIG. 4 phase plane, for various modes obtained from SVD.
Figure 7:
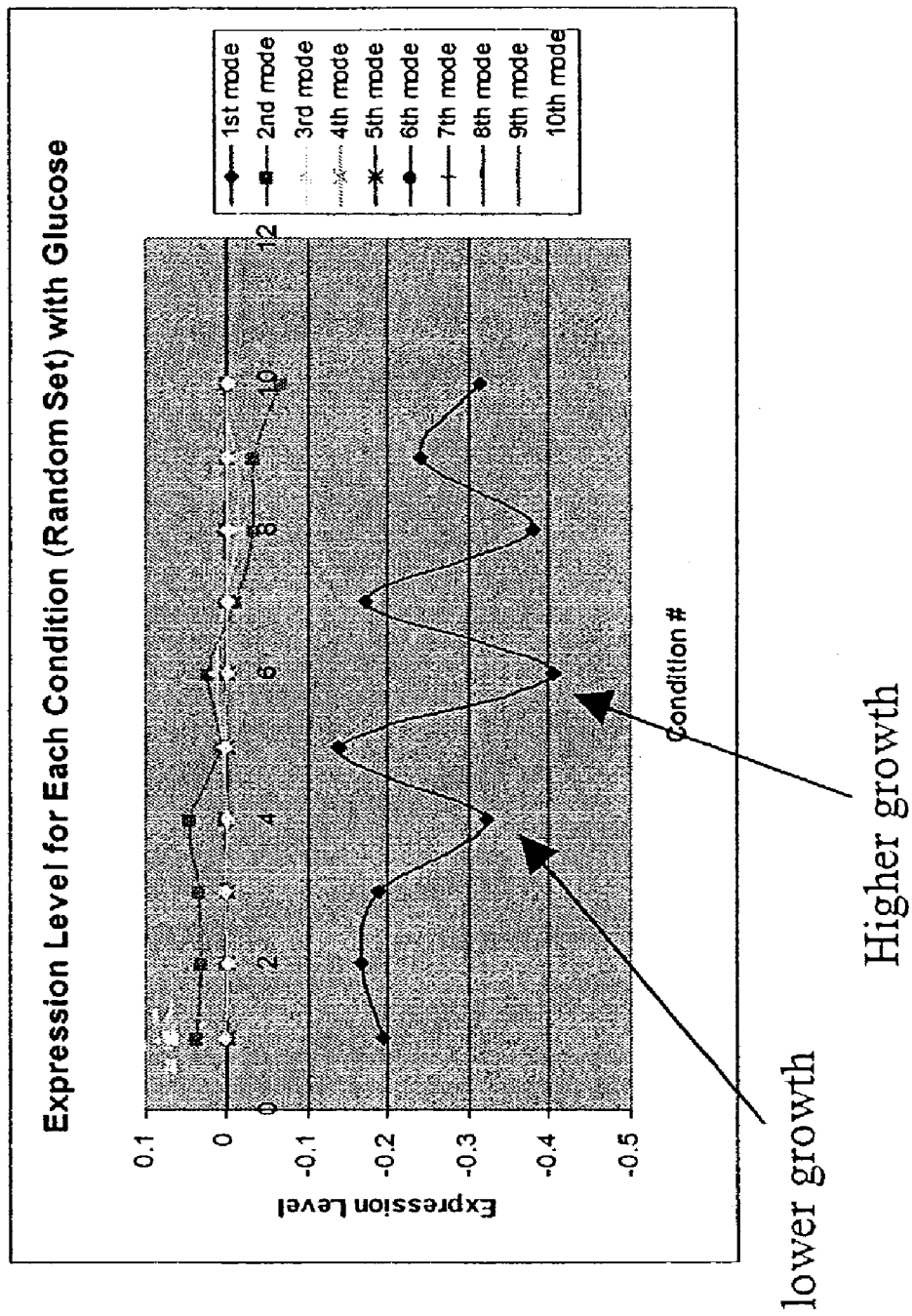
FIG. 7 shows the contribution level of each condition, or point shown in phase I of the FIG. 4 phase plane, for various modes obtained from SVD.

The contribution level of each condition (i.e. each point shown in Phase I of the phase plane) is shown in FIGS. 6 and 7 for various modes obtained from SVD. The weight that each mode has on the overall contribution of a pathway is seen by how far the curve of that mode is from the zero contribution level (horizontal zero level). Also, for each mode, the expression level increases with the condition number which shows how fluxes increase in the pathway represented by that mode. These representations provide information regarding where on the phase plane the point lies relative to other points (i.e. at a higher or lower growth rate). Thus, not only is information provided about the dominant modes, but also additional information is provided on biomass production rate. The slope of the first dominant mode ("first mode") should correspond to the slope of growth rate. The first mode captures nearly 100% of the overall contribution.

Figure 8:
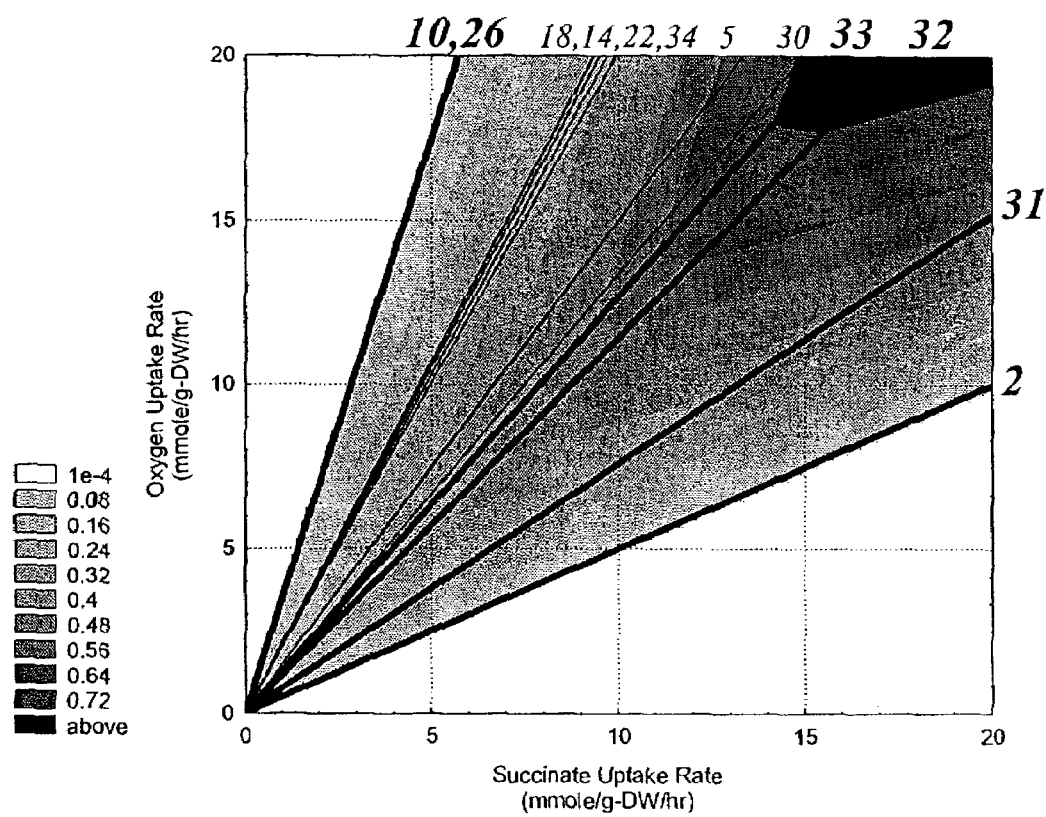
FIG. 8 shows the reduced set of extreme pathways for succinate that is presented in Table 2.
Figure 9:
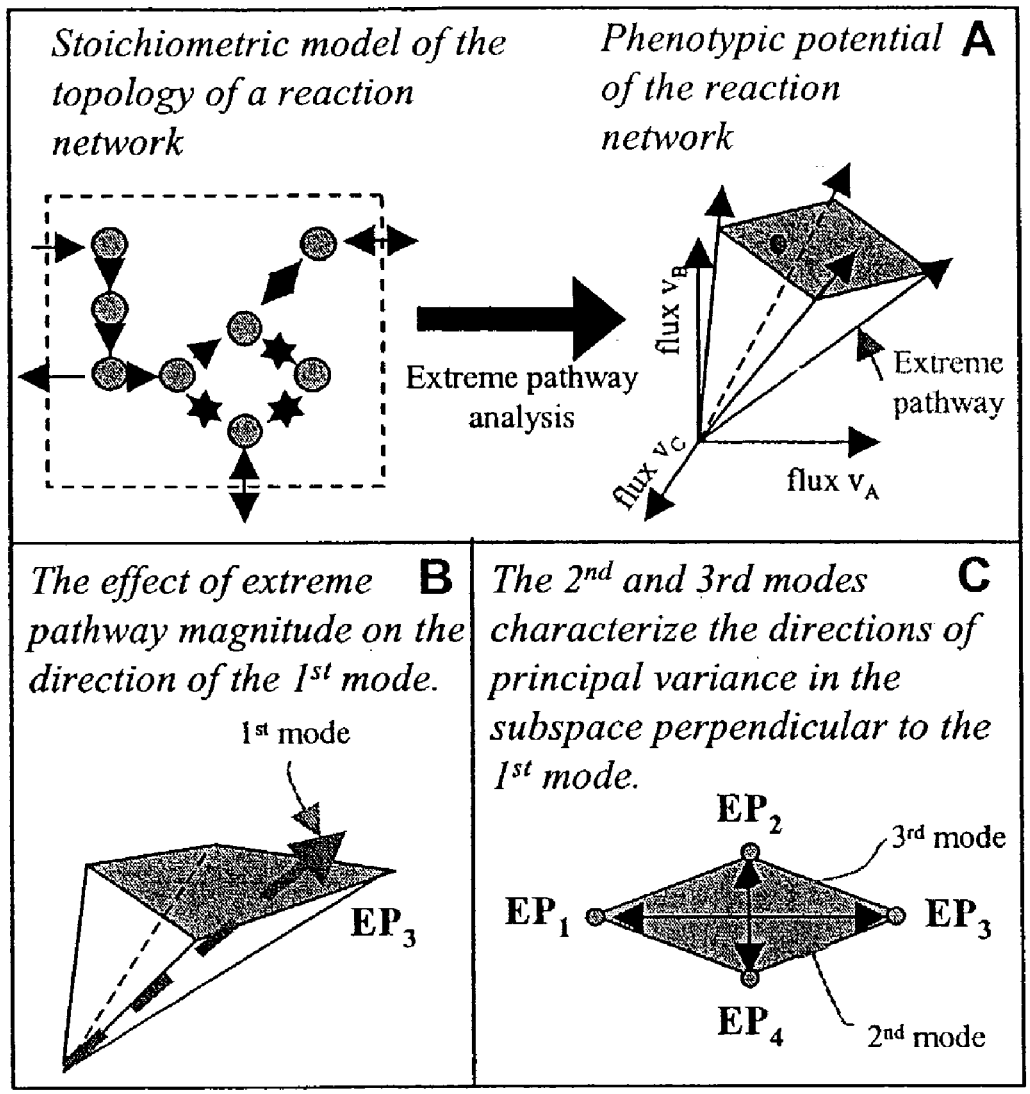
FIG. 9 shows a schematic diagram of flux balance analysis (FBA) and convex analysis to identify extreme and operational pathways of the invention.

To compare the results from SVD and with the results from pathway analysis, extreme pathways of the core *E. coli* system were calculated, using succinate as the sole carbon source. The reduced set of extreme pathways for succinate is presented in Table 2 (adopted from Schilling, supra (2000), Table 6.6) and shown in FIG. 8.

For the Phase I analysis described above, to compare the extreme pathways with the 1st mode, the genes were arranged in the same order and fluxes were normalized by succinate uptake rate. The angles between the 1st mode and each of the 12 extreme pathways were calculated and sorted in descending order. Also, the number of different fluxes (i.e. fluxes that are zero in one case and non-zero in the other case or have opposite signs) and the net flux difference between the first mode and each pathway were calculated and sorted in the same fashion. Table 3 provides the results of this analysis.

This analysis shows that the first mode in phase I is exactly equivalent to the line of optimality (i.e. P_33). It also shows that following this pathway, the first mode is the closest to pathways 32, 30, and so on. Therefore, column angle not only shows what pathways best describe flux distribution in phase I in the order of similarity, but it also shows how similar they are amongst themselves.

The analysis was repeated for Phases II and III, and for all phases together. When all phases were analyzed by SVD together, again a single dominant mode was identified (FIG. 14), with relatively low entropy (4.80E-3). The angle between this mode and each of the 12 extreme pathways was calculated. Table 4 provides the results of this analysis. By this analysis, the dominant mode was closest to extreme pathways 33 and 32 shown in Table 2.

EXAMPLE II

Identifying Human Red Blood Cell Extreme Pathways Corresponding to Physiologically Relevant Flux Distributions This example shows how a set of phenomenological pathways (flux distributions) generated by a kinetic model can be compared with the modal decomposition of a set of systemic pathways (extreme pathways) to identify dominant regulatory modes of a metabolic reaction network (human red blood cell metabolism).

The extreme pathways of the red blood cell (RBC) metabolic network have been computed (Wiback, S. J. & Palsson, B. O. Biophysical Journal 83, 808-818 (2002)). Here, SVD analysis was applied to the extreme pathway matrix, P, formed by these pathways. A full kinetic model of the entire metabolic network of the RBC has been developed (Jamshidi, N., Edwards, J. S., Fahland, T., Church, G. M., Palsson, B. O. Bioinformatics 17, 286-7 (2001); Joshi, A. & Palsson, B. O. Journal of Theoretical Biology 141, 515-28 (1991)), and was used to generate flux vectors (v) for physiologically relevant states. These flux vectors were decomposed using the modes obtained from SVD of P.

The rank of the $V_{max}$-scaled RBC extreme pathway matrix, P, was 23. The first mode represents 47% of the variance (FIG. 10F). Combined, the first five modes capture 86% of the variance of the solution space, while the first nine modes capture 95% of its variance.

Figure 10:
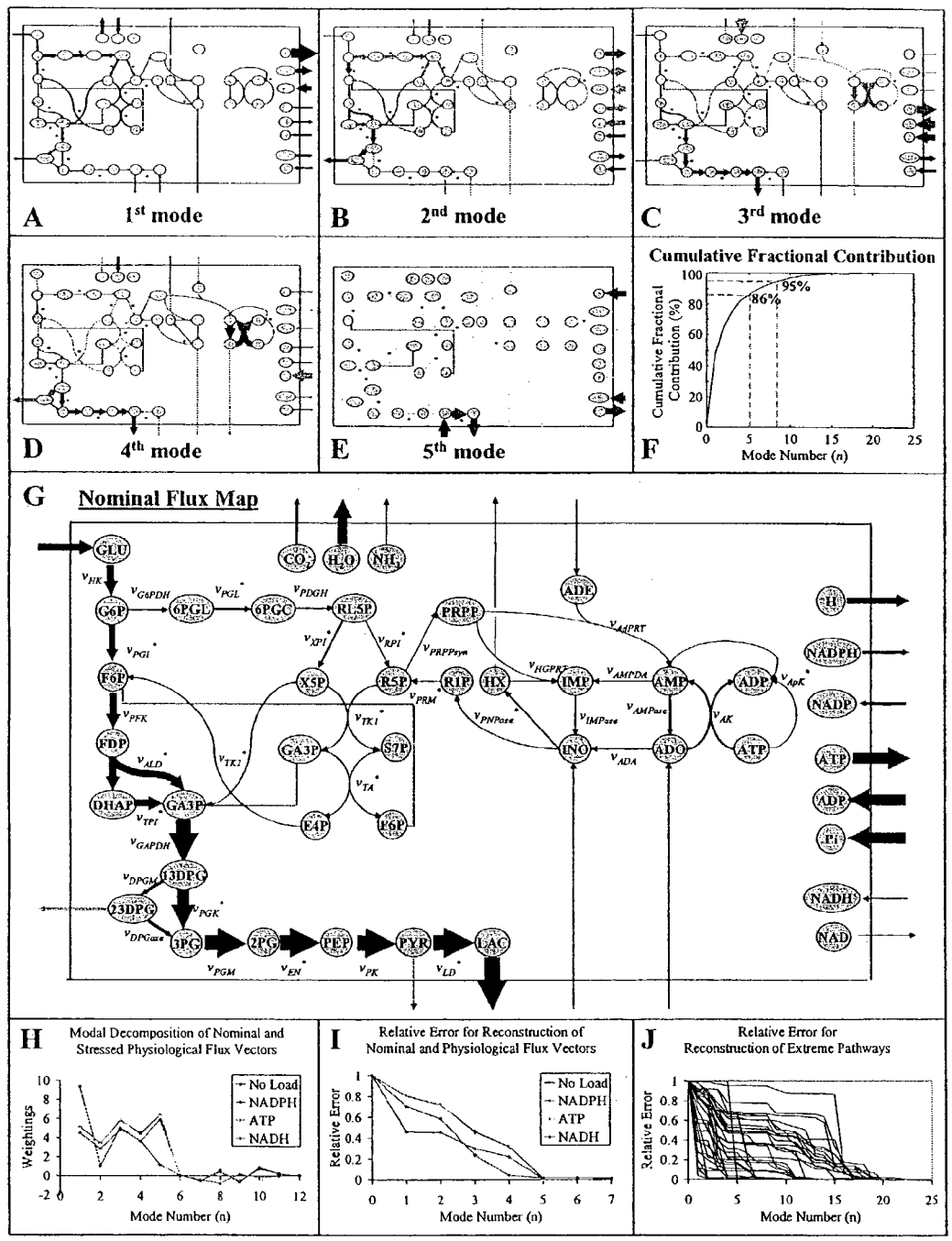
FIG. 10 shows decomposed flux vectors using the modes obtained from SVD of P for the extreme pathways of the red blood cell (RBC) metabolic network.
Figure 11:
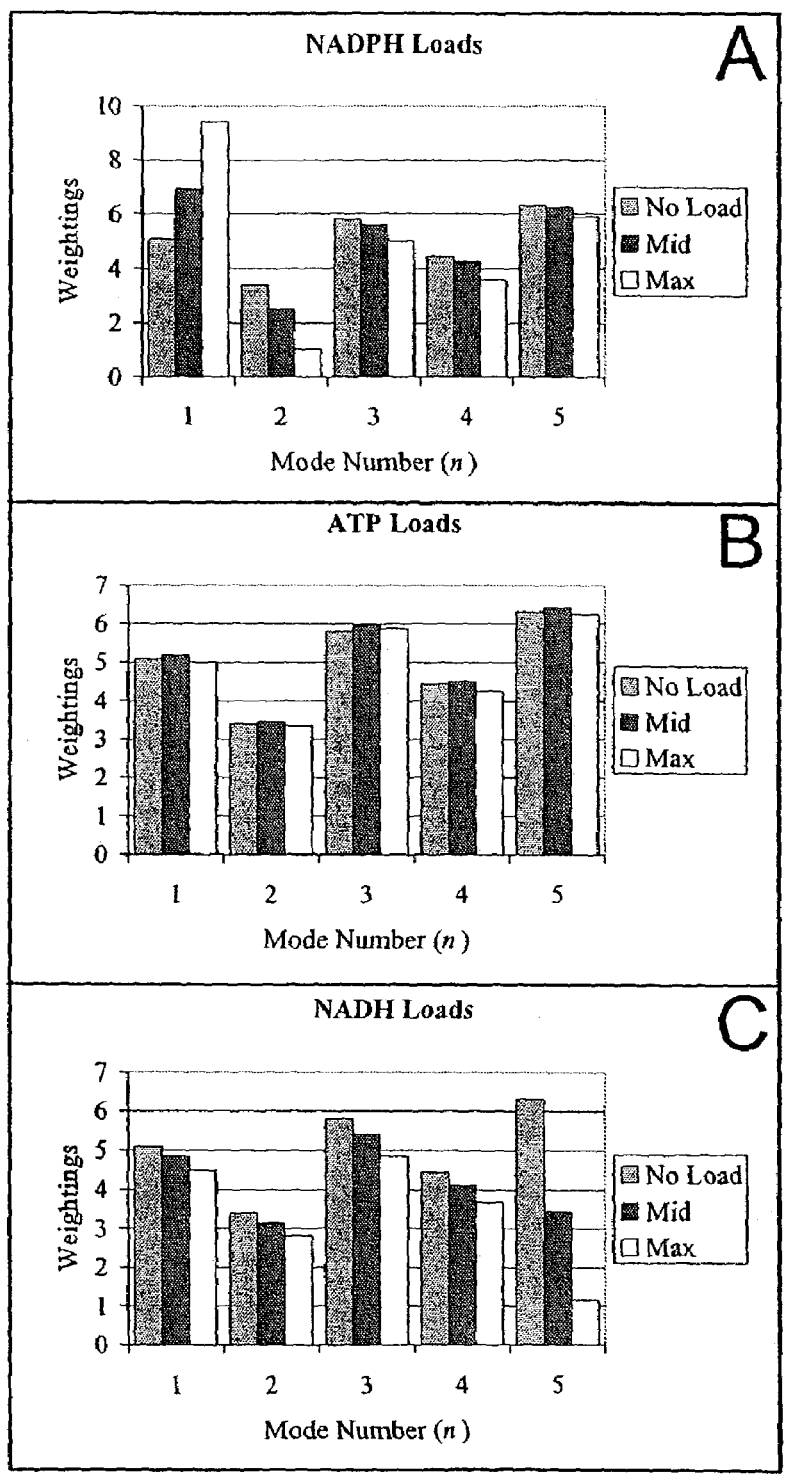
FIG. 11 shows a histogram of the first five modes of the SVD analysis shown in FIG. 10 under maximum (Max), moderate (Mid) and nominal state (no load) oxidative and energy loads.

The first five modes of P are shown on the metabolic maps in FIGS. 10(A-E). The first mode shows low flux values though the adenosine reactions, higher fluxes through the glycolytic reactions, with an exit through the R/L shunt, and the highest flux levels through the pentose phosphate pathway. This map describes the principal variance of the steady-state solution space. The subsequent modes describe the next directions of greatest variance in the steady-state solution space (FIG. 10). Movement along a mode in the positive direction corresponds to increasing the fluxes shown in red and decreasing those shown in green. Since the modes are required to be orthogonal, they specifically describe the directions of variance in the cone that are independent from each other. The subsequent modes can be interpreted biochemically as follows:

The second mode describes the flux split between glycolysis and the pentose phosphate pathway. If the contribution of this mode is added to the first mode it would lead to decreased flux through the pentose phosphate pathway and reduced production of NADPH. The increased glycolytic flux exits through the Rapoport-Leubering (R/L) shunt leading to decreased ATP production since ATP is used in upper glycolysis and not recovered in lower glycolysis. The production of NADH increases.

The third mode describes the glycolytic pathway down to pyruvate with production of ATP and NADH. It also describes lowered dissipation of ATP as a consequence of AMP dissipation by AMPase. This mode has a significant ATP production.

The fourth mode describes the flux split between lower glycolysis and the R/L shunt. It thus naturally interacts biochemically with the second mode. The fourth mode further describes an increase in ATP dissipation via the AMPase-AK cycle leading to little net production of ATP, and interacts with mode three.

The fifth mode is actually one of the extreme pathways. It describes importing pyruvate and converting it to lactate, thus dissipating one NADH. It thus will be important in balancing NADH redox metabolism.

As shown below the first five modes account for most of the RBC's physiological states.

The nominal state (no additional metabolic load) of the red blood cell metabolic network was calculated using a full kinetic model and is shown on the RBC metabolic map (FIG. 10G). This nominal physiologic steady state of the RBC was decomposed into 23 modes (FIG. 10H). The relative error remaining in the reconstructed solution after the addition of each mode to the reconstruction of the nominal steady state fell sharply (FIG. 10H). After the contribution of the first five modes, the reconstructed nominal state had a relative error of 0.013 (RE(5)=0.013).

An inspection of the first five modes (FIGS. 10 A-E) demonstrates how they reconstruct the physiologic steady state solution. Relative to the first mode (FIG. 10A), adding the second mode (FIG. 10B) increases the flux through the first half of glycolysis, decreases the flux through the pentose phosphate reaction, and decreases NADPH production, all of which moves the reconstructed solution significantly towards the physiologic steady state (FIG. 10G). Adding the third mode (FIG. 10C) increases the flux through all of glycolysis, particularly through lower glycolysis. The addition of the fourth mode (FIG. 10D) appropriately decreases the amount of 23DPG that is produced and instead sends that flux through lower glycolysis. Finally, the addition of the fifth mode increases the flux from pyruvate to lactate, which leads essentially to the steady state solution where lactate is the primary output of glycolysis. Thus, the significant features of the physiologic steady state are captured within the first five modes. A regulatory structure that can move the solution along these five independent directions in the solution space will be able to generate the desired physiological state.

Steady-state flux distributions for two load levels of NADPH, ATP, and NADH were calculated using the RBC kinetic model. These pairs of load levels each represented the maximum load the in silico RBC could withstand, as well as one value chosen within the tolerated load range. NADPH loads simulate physiologic states corresponding to the red blood cell's response to oxidative free radicals. The maximum NADPH load is 2.5 mM/hr. The ATP loads simulate conditions of increased energy loads, such as in hyperosmotic media. The maximum ATP load is 0.37 mM/hr. Two NADH loads, important for methemoglobin reduction in the RBC, were also applied. These six computed flux vectors thus represent extreme physiological states of the RBC, and help designate the region of physiologically meaningful states within the steady-state solution space.

The modal composition of each of the six "stressed" steady state flux solutions gives significant weighting to the first five modes (FIG. 10H). In addition, some "fine tuning" appears in modes 7 to 11. All of the other modes are essentially insignificant in reconstructing these solutions to the RBC kinetic model.

The application of metabolic loads changed the weighting of the first five modes to reconstruct the appropriate metabolic flux distribution (FIGS. 10H,I). Increases in the NADPH load resulted in a substantial increase of the weighting on the first mode, increasing the flux through the pentose phosphate reactions and thus elevating the production of NADPH. The weightings on the second, third, fourth, and fifth modes decrease with the application of higher NADPH loads largely because as NADPH production is maximized the flux distribution approaches that of the first mode. The reduction in the weighting of the second mode, however, is the most dramatic. The application of increasing ATP loads resulted in little change in the values of the weightings on all of the first five modes. The application of ATP load is handled in the RBC by a decrease in an ATP-consuming futile cycle, with the ATP generated instead being used instead to satisfy the load imposed upon the cell. Thus, the usage of an ATP-dissipating futile cycle in the unstressed state of the RBC acts to dampen the effects of changing ATP loads, allowing the RBC to respond to changing ATP loads with little change in the overall flux distribution in the cell. Related experimental findings have demonstrated that the concentration of ATP in the RBC does not change much as environmental conditions change within specified limits, as a result of this buffer, but then changes dramatically when the ATP load is pushed beyond those limits. The application of the NADH loads resulted in a significant decrease of all the mode weightings because the length of the flux vector decreases. The weighting on the fifth mode decreased most dramatically since it consumes NADH when utilized in the positive direction and thus had needed to be scaled down.

After the inclusion of the first five modes, the relative error (RE(5)) of all the reconstructed solutions ranged from 0.005 to 0.018. In all six cases, the first five modes reconstructed at least 98% of the steady state solutions. Thus, the physiologically relevant portion of the steady-state solution space appears to be only 5 dimensional, and therefore there are effectively only five degrees of freedom to the problem of regulating red cell metabolism.

Decomposition of the extreme pathway vectors into the modes shows that the most important mode, in the reconstruction, is often not one of the first five modes (FIG. 10J). Thus, many portions of the allowable solution space, as defined by the extreme pathways, are poorly characterized by the first five modes, which effectively reconstruct each solution to the full RBC kinetic model. Thus, many of the extreme pathways are physiologically irrelevant and they can be identified using SVD of P, if the approximate location of physiologically meaningful solutions is known.

Study of regulation of metabolism has historically focused on the identification and characterization of individual regulatory events. Now that we can reconstruct full metabolic reaction networks we can address the need for regulation from a network-based perspective. This study has focused on interpreting regulation from a network-based perspective using singular value decomposition of the extreme pathway matrix for human red blood cell metabolism. Two main results were obtained. First, the dominant modes obtained by SVD interpret RBC metabolic physiology well. Second, the first five modes effectively characterize all the relevant physiological states of the red cell.

RBC metabolic physiology is well interpreted by the dominant modes obtained from SVD. Using the calculated modes, seven physiologically relevant solutions to the full RBC kinetic model were reconstructed. The RE(5) for these solutions was within 0.017. Thus, the first five modes can be used to essentially completely recapture each of the physiologically relevant kinetic solutions. However, most of the extreme pathways could not be reconstructed to such a high degree by the first five modes. Thus, the first five modes represented the space relevant to solutions to the full kinetic model better than they did to the space as a whole, even though they were calculated to optimize their description of the entire space. This fact suggests that developing constraints-based methods that take into account kinetics and metabolomics will result in defining a solution space that is much smaller than the space circumscribed by the extreme pathways.

The results obtained herein were based on the topology of the metabolic network and knowledge of some $V_{max}$ values. The next step to bridge the gap between the network-based results and the study of individual regulatory events is to find the best ways to pair candidate regulatory molecules and the systemic regulatory needs. In control theory this is known as the 'loop-pairing' problem (Seborg, D. E., Edgar, T. F. & Mellichamp, D. A. Process dynamics and control (Wiley, N.Y., 1989)). As a part of its solution we may have to relax the need for strict orthonormality of the modes and look for oblique modal bases that are more in line with the underlying biochemistry of the network.

Taken together, this study presents a network-based approach to studying regulatory networks and defines the degrees of freedom of the regulatory problem. This method calculates the modalities needed to enable the metabolic network to navigate its solution space and thus could be used to infer candidate regulatory loops of metabolic systems for which the regulation is largely unknown. Further, based upon their contribution to the steady-state solution space, these regulatory loops can potentially be ordered in terms of their importance to the reconstruction of the space. Network-based approaches to studying regulation, such as the one offered herein, complement component-based studies and provide a potential framework to better understand the interaction of regulatory components needed to achieve the regulatory demands of the cell.

EXAMPLE III

In Silico Assessment of the Phenotypic Consequences of Red Blood Cell Single Nucleotide Polymorphisms The following example illustrates the application of the described methods to analysis of phenomenological pathways defined through pathological data.

Figure 12:
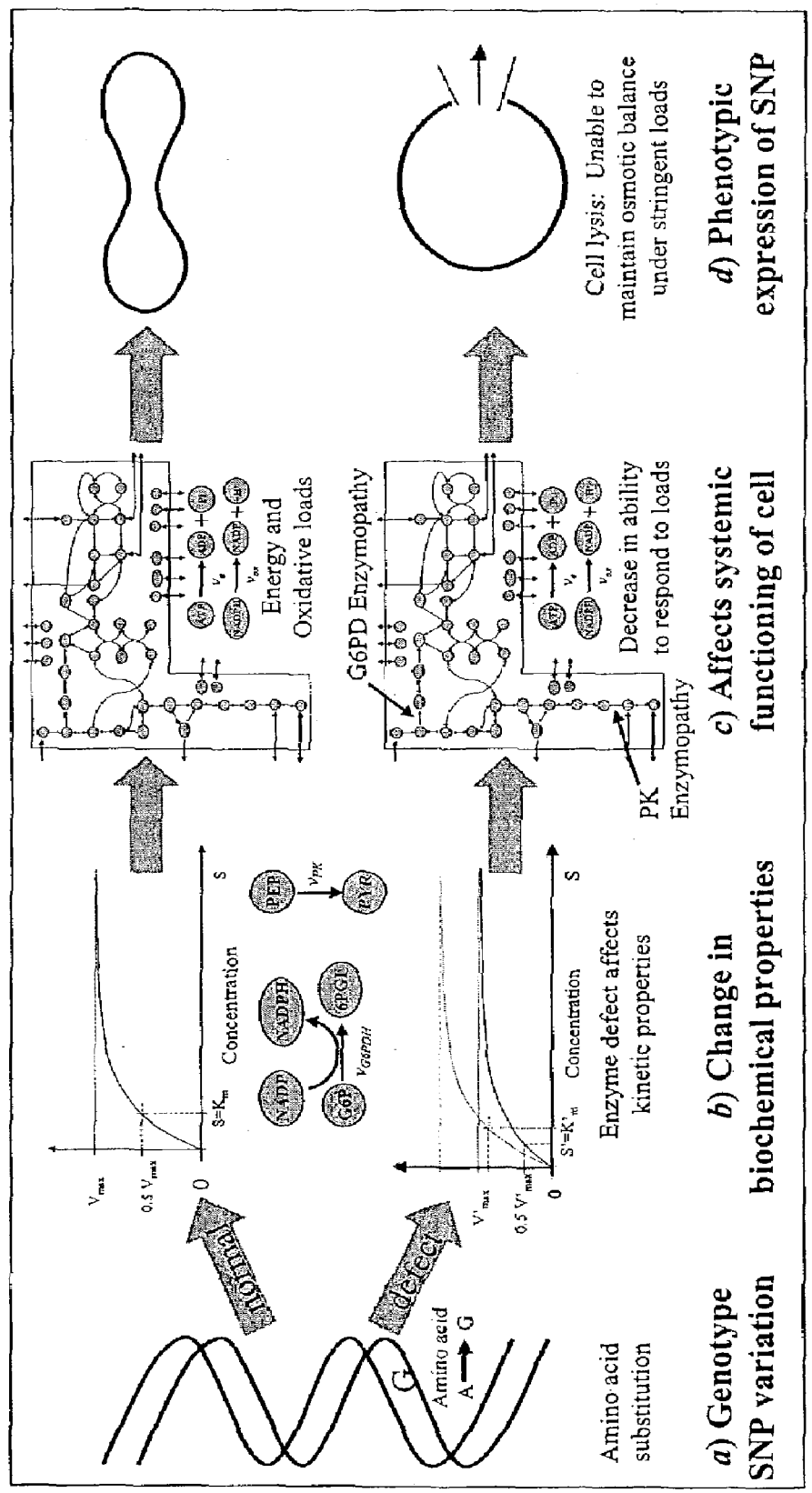
FIG. 12 shows a schematic diagram for building large-scale in silico models of complex biological processes.

The Human Genome Project (HGP) is now essentially complete. One result of the HGP is the definition of single nucleotide polymorphisms (SNPs) and their effects on the development of human disease. Although the number of SNPs in the human genome is expected to be a few million, it is estimated that only 100,000 to 200,000 will effectively define a unique human genotype. A subset of these SNPs are believed to be "informative" with respect to human disease (Syvanen, A., 2001. Accessing genetic variation: Genotyping single nucleotide polymorphisms. Nat Rev Genet 2: 930-942). Many of these SNPs will fall into coding regions while others will be found in regulatory regions. The human genotype-phenotype relationship is very complex and it will be hard to determine the causal relationship between sequence variation and physiological function. One way to deal with this intricate relationship is to build large-scale in silico models of complex biological processes (FIG. 12). Defects or alterations in the properties of a single component in complex biological processes can be put into context of the rest by using an in silico model. In this work, recent data on SNPs in key red blood cell enzymes (FIG. 12a) and corresponding alterations in their kinetic properties (FIG. 12b) were used in an in silico red blood cell model (FIG. 12c) to calculate the overall effect of SNPs on whole cell function (FIG. 12d).

The study of variations in the kinetic properties of red blood cell enzymes is not merely an academic study of the quality of a mathematical model, but has real utility in the clinical diagnosis and treatment of enzymopathies and can provide a link to the underlying sequence variation (FIG. 12). Here, an in silico model is used to study SNPs in two of the most frequent red blood cell enzymopathies: glucose-6-phosphate dehydrogenase (G6PD) and pyruvate kinase (PK).

For both enzyme deficiencies, clinical data was obtained from the published literature to determine measured values for the various kinetic parameters ($V_{max}$'s, Km's, Ki's) associated with each clinically diagnosed variant. These numerical values were then used in the in silico model (Jamshidi, N., Edwards, J. S., Fahland; T., Church, G. M., Palsson, B. O. Bioinformatics 17, 286-7 (2001)) and sensitivities to various oxidative and energy loads (above normal, baseline values) were simulated. The results are interpreted with respect to the genetic basis of the enzymopathy in an attempt to establish a direct link between the genotype and phenotype (FIG. 12).

Glucose-6-phosphate dehydrogenase (G6PD) catalyzes the first step in the oxidative branch of the pentose pathway (FIG. 12c) and is thus of critical importance in maintaining the red blood cell's resistance to oxidative stresses. G6PD is the most common erythrocyte enzymopathy, affecting approximately 400 million people worldwide.

G6PD from normal patients and patients with hemolytic anemia have been characterized on the molecular level. A total of 61 G6PD class I variants have been described at the molecular level. Of the 61 class I chronic variants, 55 are the result of SNPs involving amino acid changes, 5 result from frame deletions and one results from a splicing defect (Fiorelli, G., F. M. d. Montemuros and M. D. Cappellini, Bailliere's Clinical Haematology 13: 35-55 (2000)).

Figure 13:
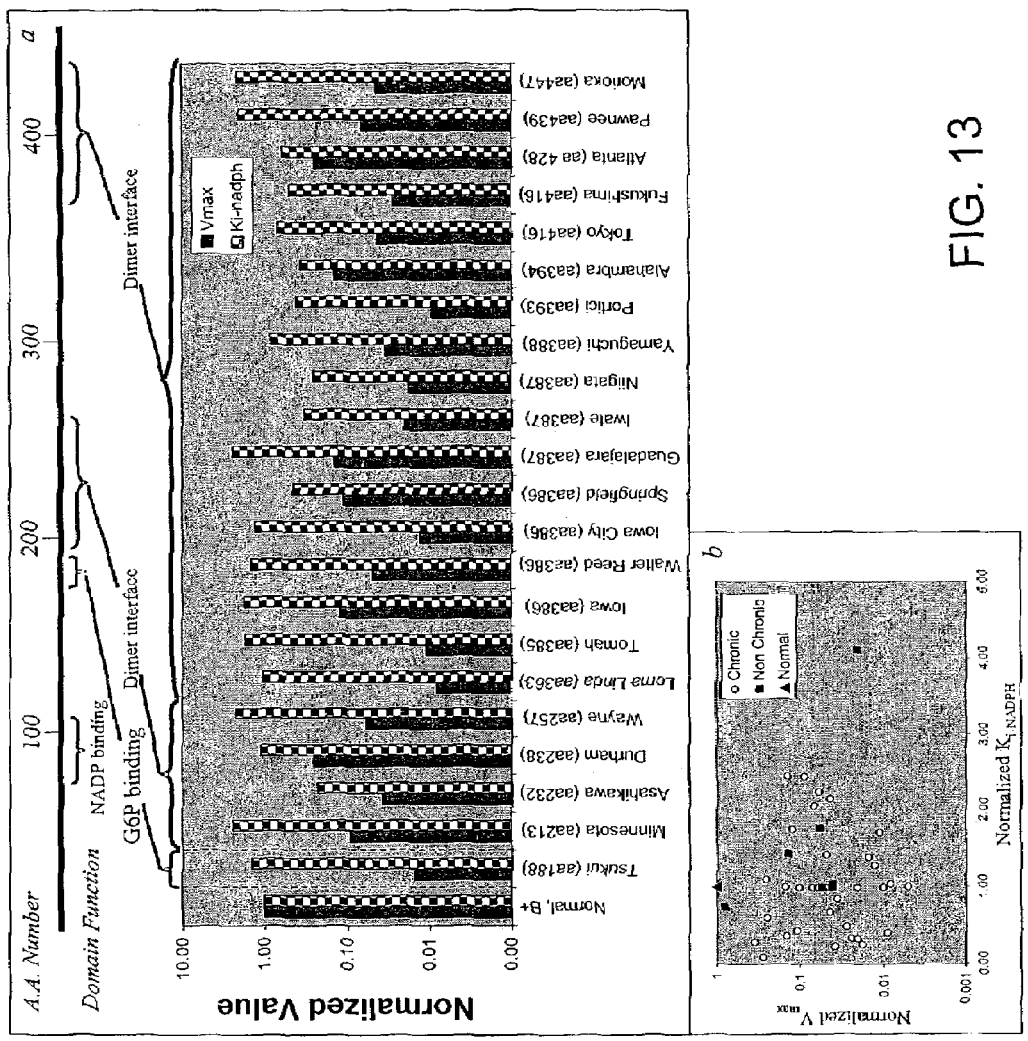
FIG. 13 shows the localization of single nucleotide polymorphism clusters found in clinically diagnosed glucose-6-phosphate dehydrogenase (G6PD) patients.

Clinically diagnosed SNPs cluster around important, active regions of G6PD enzyme including the dimer interface and substrate binding sites (FIG. 13a). Numerical values of G6PD kinetic parameters were varied in silico to determine the sensitivity of red blood cell metabolic functions to these changes in enzyme function. The most sensitive parameters were found to be $V_{max}$ and Ki-NADPH. The NADPH/NADP ratio proved to be the most informative indicator of metabolic status as it was the most sensitive to changes in these two parameters and it gives an indication as to the oxidative state of the cell (Kirkman, H. N., G. D. Gaetani, E. H. Clemons and C. Mareni, Journal of Clinical Investigation 55: 875-8 (1975)). For each documented variant there appears to be no direct correlation between $V_{max}$ and Ki-NADPH (FIG. 13b). Clinically, G6PD deficiencies are broken down into two main categories: chronic and non-chronic hemolytic anemia. Chronic cases show clinical symptoms and are very sensitive to the environment. Non-chronic cases appear normal under homeostatic conditions but can experience problems when subjected to large oxidative stresses (Jacobasch, G., and S. M. Rapoport, in Molecular Aspects of Medicine (1995)). For this study, kinetic data for 12 chronic and 8 non-chronic cases from Yoshida and 19 chronic cases from Fiorelli were used (Fiorelli, G., F. M. d. Montemuros and M. D. Cappellini, Bailliere's Clinical Haematology 13: 35-55 (2000); Yoshida, A., pp. 493-502 in Glucose-6-Phosphate Dehydrogenase. Academic Press 1995).

Figure 14:
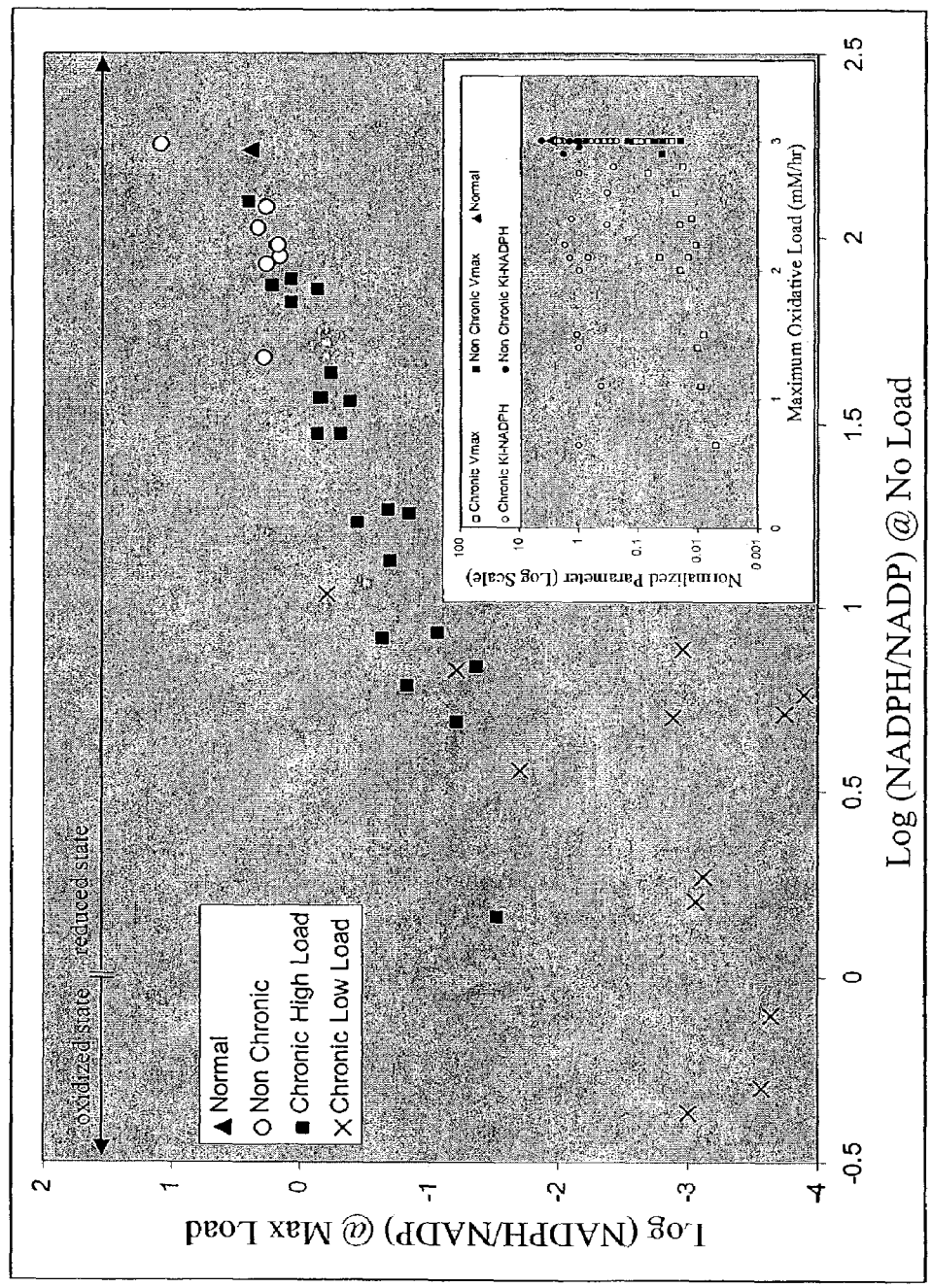
FIG. 14 shows the toleration of oxidative load between chronic and non-chronic hemolytic anemia states having G6PD SNPs.

Under normal conditions (i.e. oxidative load, $V_{ox}=0$) there are differences between the chronic and non-chronic groups with the chronic group having a somewhat lower homeostatic steady state NADPH/NADP ratio than the non-chronic group. When subjected to an oxidative load ($V_{ox}>0$), noticeable differences between the two groups (chronic and non-chronic) appear (FIG. 14). The NADPH/NADP ratio at the maximum tolerated oxidative load ($V_{ox}$=max value) correlates with this ratio in the un-stressed situation ($V_{ox}=0$). The group of chronic hemolytic anemia patients are clearly separated from the normal and non-chronic group. A number of the chronic cases can only withstand a very modest oxidative load. Of the variant cases studied, a handful have been characterized at the molecular (amino acid) level (Table 5). Of the cases considered, most of the single base changes in the chronic (class I) variants occur at or near the dimer interface (exons 10,11 and 6,7) or near the NADP binding site, leading to an impaired ability to respond to systemic oxidative challenges.

Pyruvate kinase (PK) is a key glycolytic regulatory enzyme. There have only been about 400 documented variants since PK's first description in 1961 (Jacobasch, G., and S. M. Rapoport, in Molecular Aspects of Medicine (1996); Tanaka, K. R., and C. R. Zerez, Seminars in Hematology 27: 165-185 (1990); Zanella, A., and P. Bianchi, Balliere's Clinical Hematology 13: 57-81 (2000)). PK accounts for 90% of the enzyme deficiencies found in red blood cell glycolysis. It is autosomal recessive where clinical manifestations appear only in compound heterozygotes (2 mutant alleles). There are four isozymes: L, R, M1, and M2, with the R type being exclusive to the red blood cells. PK is encoded by the PK-LR gene on chromosome 1q21. The kinetics of the enzyme have been extensively studied (Otto, M., R. Heinrich, B. Kuhn and G. Jacobasch, European Journal of Biochemistry 49: 169-178 (1974)). PK activity is regulated by F6P, ATP, Mg, and MgATP. Anemic heterzygotes have 5-40% of normal PK activity.

A summary of the PK variants is presented in Table 6. The Sassari variant only has a SNP (cDNA nt 514) transversion of a G to a C resulting in a change of Glu to Gln at aa 172 which is in between the β1 and β2 in the B domain. Here a basic (negatively charged amino acid) is replaced by a polar uncharge amino acid. Parma has 2 SNPs, one at aa 331 or 332 and another at aa 486 or 487, neither of whose amino acid changes have been elucidated yet. Soresina and Milano share the amino acid change Arg to Trp at aa 486 (positively charged to non-polar). Brescia has a deletion of Lys at aa 348 and another change at aa 486 or 487 that has not been defined yet. Mantova has an exchange at amino acid 390 Asp to Asn (negatively charged to polar uncharged). (Bianchi, P., and A. Zanella, 2000 Hematologically important mutations: red cell pyruvate kinase. Blood Cells, Molecules, and Diseases 15: 47-53; Zanella, A., and P. Bianchi, Balliere's Clinical Hematology 13: 57-81 (2000)).

Figure 15:
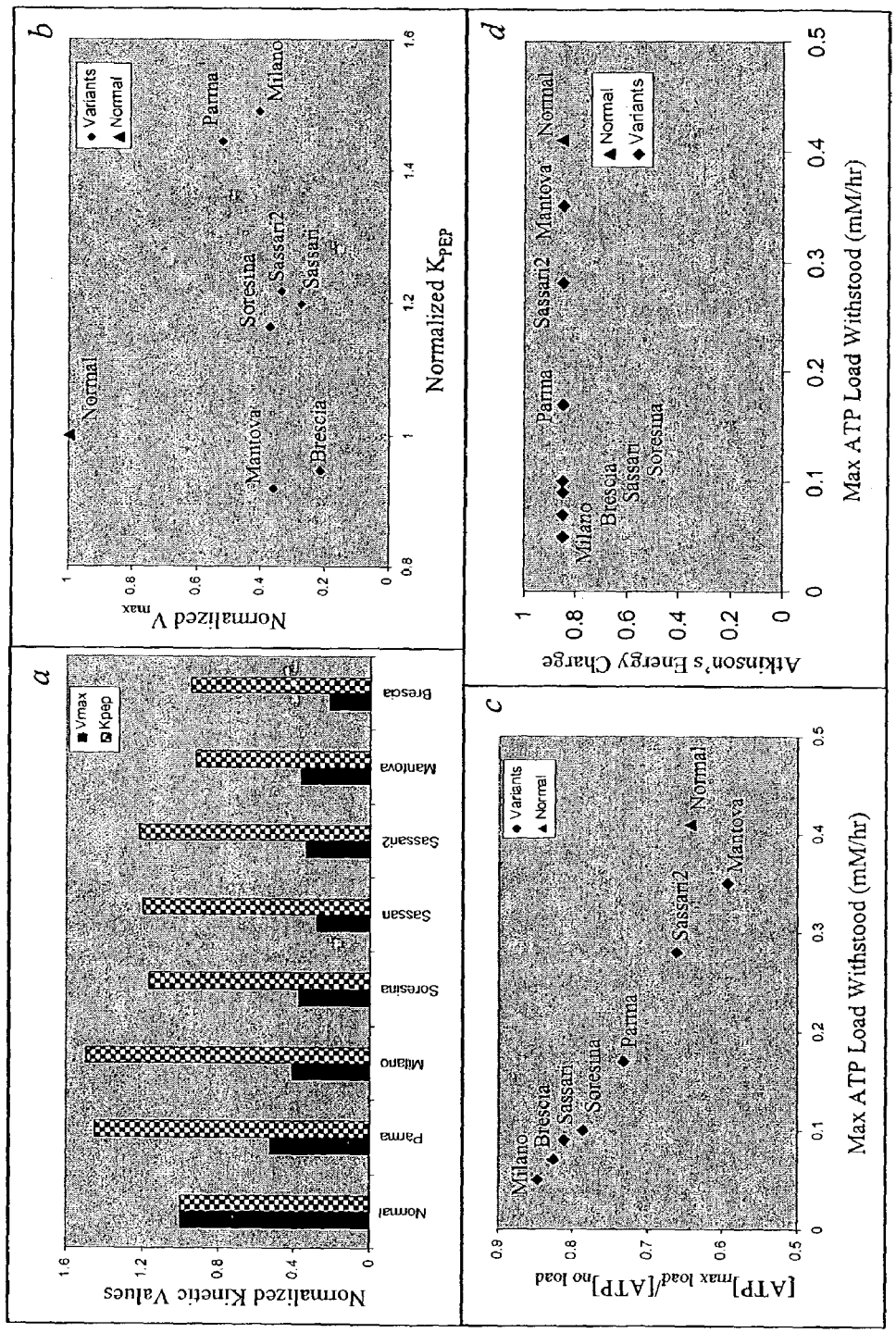
FIG. 15 shows the characterization and toleration of energy loads for glycolytic states harboring different pyruvate kinase (PK) SNP variants.

Unlike for G6PD, the characterized PK SNPs are scattered throughout the protein coding region and do not appear to cluster near the corresponding active site of the enzyme. The documented kinetic values for the main kinetic parameters $V_{max}$ and KPEP are shown (FIG. 15a). Similar to the G6PD variants, there is not a clear correlation between changes in the numerical $V_{max}$ and KPEP amongst the PK variants (FIG. 15b). Although changes in KADP are also documented for each variant and accounted for in the simulations, increases or decreases in its value did not significantly affect the red blood cell's steady state metabolite concentrations or its ability to withstand energy loads (data not shown). Changes in KPEP and $V_{max}$ influence the concentration of ATP and 2,3DPG most significantly. When increased energy loads ($V_e>0$) are applied in silico, differences between the variants are observed. The ratio between the ATP concentration at maximum tolerated load (ve=max value) and the ATP concentration in the unchallenged state ($V_c$=0) varies approximately linearly with the maximum tolerated load when all the variants are evaluated (FIG. 15c). Thus the variants that tolerated the lowest maximum load have a [ATP]max/[ATP]no load ratio close to unity indicating their sharply diminished ability to deviate from the nominal homeostatic state. Interestingly, the computed energy charge (EC=(ATP+½ADP)/(ATP+ADP+AMP)) (Atkinson, D. E., 1977 Cellular energy metabolism and its regulation. Academic Press, New York) stays relatively constant (FIG. 15d). This result indicates that red blood cell metabolism strives to maintain its EC within the tolerated load range, thus allowing for an energetically consistent metabolic function.

Sequence variations in coding regions for metabolic enzymes can lead to altered kinetic properties. The kinetic properties of enzymes are described by many parameters and a single SNP can alter one or many of these parameters. For the variants of G6PD and PK considered here, there appears to be no clear relationship between their kinetic parameters as a function of sequence variation. Thus consequences of sequence variations on the function of a gene product must be fully evaluated to get a comprehensive assessment of the altered biochemical function.

The consequences of many simultaneously altered enzyme properties must in turn be evaluated in terms of the function of the enzyme in the context of the reaction network in which it participates. The assessment of sequence variation on biochemical and kinetic properties of enzymes may seem difficult and this challenge is currently being addressed (Yamada, K., Z. Chen, R. Rozen and R. G. Matthews, Proc Natl Acad Sci U S A 98: 14853-14858 (2001)), but the assessment of sequence variation on entire network function is even more complicated. This highly complex and intricate relationship between sequence variation and network function can be studied through the use of a computer model,. Here we have shown that a large number of variants in red blood cell G6PD and PK can be systematically analyzed using an in silico model of the red blood cell. Correlation between sequence variation and predicted overall cell behavior is established, and in the case of G6PD, it in turn correlates with the severity of the clinical conditions.

EXAMPLE IV

Consistency Between Known Regulatory Network Structures and Transcriptomics Data The following example illustrates the use of the described methods to validate and expand known regulatory network structures by reconciling these structures with large-scale gene expression data sets.

The availability of large genome-scale expression data sets has initiated the development of methods that use these data sets to infer large-scale regulatory networks (D'Haeseleer, P., Liang, S. & Somogyi, R Bioinformatics 16:707-26 (2000); de Jong, H. J. Comput. Biol. 9:67-103 (2002); Yeung, M. K., Tegner, J. & Collins, J. J. Proc. Natl. Acad. Sci. USA 99:6163-8 (2002)). Alternatively, such regulatory network structures can be reconstructed based on annotated genome information, well-curated databases, and primary research literature (Guelzim, N., Bottani, S., Bourgine, P. & Kepes, F. Nat. Genet. 31, 60-3. (2002); Shen-Orr, S. S., Milo, R., Mangan, S. & Alon, U. Nat. Genet. 31, 64-8 (2002)). Here we examine how consistent existing large-scale gene expression data sets are with known genome-wide regulatory network structures in *Echerichia coli* and *Saccharomyces cerevisiae*. We find that approximately 10% of the known pair-wise regulatory interactions between transcription factors and their target genes are consistent with gene expression data in both organisms. We show that accounting for combinatorial effects due to multiple transcription factors acting on the same gene can improve the agreement between gene expression data and regulatory network structures. We also find that regulatory network elements involving repressors are typically less consistent with the data than ones involving activators. Taken together these results allow us to define regulatory network modules with high degree of consistency between the network structure and gene expression data. The results suggest that targeted gene expression profiling data can be used to refine and expand particular subcomponents of known regulatory networks that are sufficiently decoupled from the rest of the network.

The known genome-scale transcriptional regulatory network structures for yeast (Guelzim, N., Bottani, S., Bourgine, P. & Kepes, F. Nat. Genet. 31, 60-3. (2002)) and *E. coli* (Shen-Orr, S. S., Milo, R., Mangan, S. & Alon, U. Nat. Genet. 31, 64-8 (2002)) were obtained and pre-processed to remove autoregulation. These structures were represented as graphs with directed regulatory interaction edges between a regulator node (typically a transcription factor) and a target gene node, with the mode of regulation (activation, repression, or both) indicated for each interaction. The yeast network has 108 regulatory genes regulating 414 target genes through 931 regulatory interactions, whereas the *E. coli* network has 123 regulatory genes regulating 721 target genes through 1367 regulatory interactions. We used data from a total of 641 diverse gene expression profiling experiments organized into five separate data sets for yeast and 108 experiments organized into three separate data sets for *E. coli*.

There were three basic types of regulatory network elements analyzed in this study: 1) pair-wise regulatory interactions, 2) target-regulator units, and 3) regulons. A target-regulator unit (TRU) is defined as a single target gene together with all of its transcriptional regulators. A regulon is defined as the set of all target genes for a single transcriptional regulator. For each instance of the individual network elements present in the network, we computed a consistency measure between a particular gene expression data set and the network element structure. The particular measures we used were Pearson correlation coefficients for pairwise interactions, multiple coefficients of determination for TRUs, and average within regulon correlation for regulons. The statistical significance of a particular value of a consistency measure was determined by a randomization procedure.

The simplest elements in the regulatory network are pair-wise regulator-target interactions. Overall only a relatively small fraction (less than 10% at P<0.01) of pairwise interactions are in agreement with the gene expression data given the criteria stated above. In particular, virtually none of the repressor-target interactions are supported by any of the gene expression data sets examined. Most repressors actually have positive correlation with the expression of their target genes—not negative as would be expected for a repressor. These results for repressing pair-wise interactions highlights the problems associated with detecting transcripts expressed at a low level as a result of a transcriptional repressor bound to the promoter of the target gene.

Analysis of pair-wise correlations could overestimate correlations between transcription factor and target gene expression levels in the presence of transcriptional feed-forward loops. In such cases two or more transcription factors act on the same gene, but some of them (primary regulators) also regulate another (secondary) regulator directly. Feed-forward loops can lead to an indirect effect by which the secondary regulator-target correlation is solely due the influence of the primary regulators. In the framework used here, this effect can be accounted for by replacing standard correlation coefficients with partial correlation coefficients for secondary regulator-target interactions. Although there is a significant number of feed-forward loops in both networks (240 in yeast, 206 in E. coli), the overall effect of accounting for feed-forward loops is small (0-3 percentage points).

Target-regulator units represent more complex combinatorial effects than feed-forward loops. The percentage of TRUs consistent with gene expression data is higher than the percentage of consistent pair-wise interactions for E. coli at all confidence levels. This result indicates that combinatorial effects between transcription factors play a significant role in many cases. Conversely for TRUs in yeast, we do not observe a significant change in the percentage of units in agreement with expression data compared to the calculations that considered only pairwise interactions.

TRUs can be categorized by the number of regulators that act on the target gene. In yeast, the TRUs with four regulators are in general best supported by the gene expression data. These four-regulator TRUs include genes participating in diverse cellular functions including nitrogen utilization, oxygen regulation, and stress response. Hence the high degree of consistency observed for four-regulator TRUs does not appear to be solely due to a particular subcomponent of the network, but is a more general feature of the network structure. In E. coli, no clear dependence between the number of regulators and the fraction of consistent TRUs can be detected.

In order to investigate the agreement between regulatory network structures and gene expression data from a different perspective that does not assume correlation between the expression levels of transcription factors and their target genes, we studied the coherence of gene expression within known regulons. A large fraction of regulons (over 40%) have coherent gene expression in both yeast and E. coli even for the most stringent confidence level (P<0.001) in at least one data set. This result indicates that a clustering-like approach to analyzing gene expression data can indeed be expected to be successful in detecting truly co-regulated genes. The most interesting feature of this calculation is the relatively low level of regulon coherence for regulons regulated by transcriptional repressors in yeast. In contrast, E. coli regulons controlled by repressors tend to be more coherent than those controlled by activators.

Figure 16:
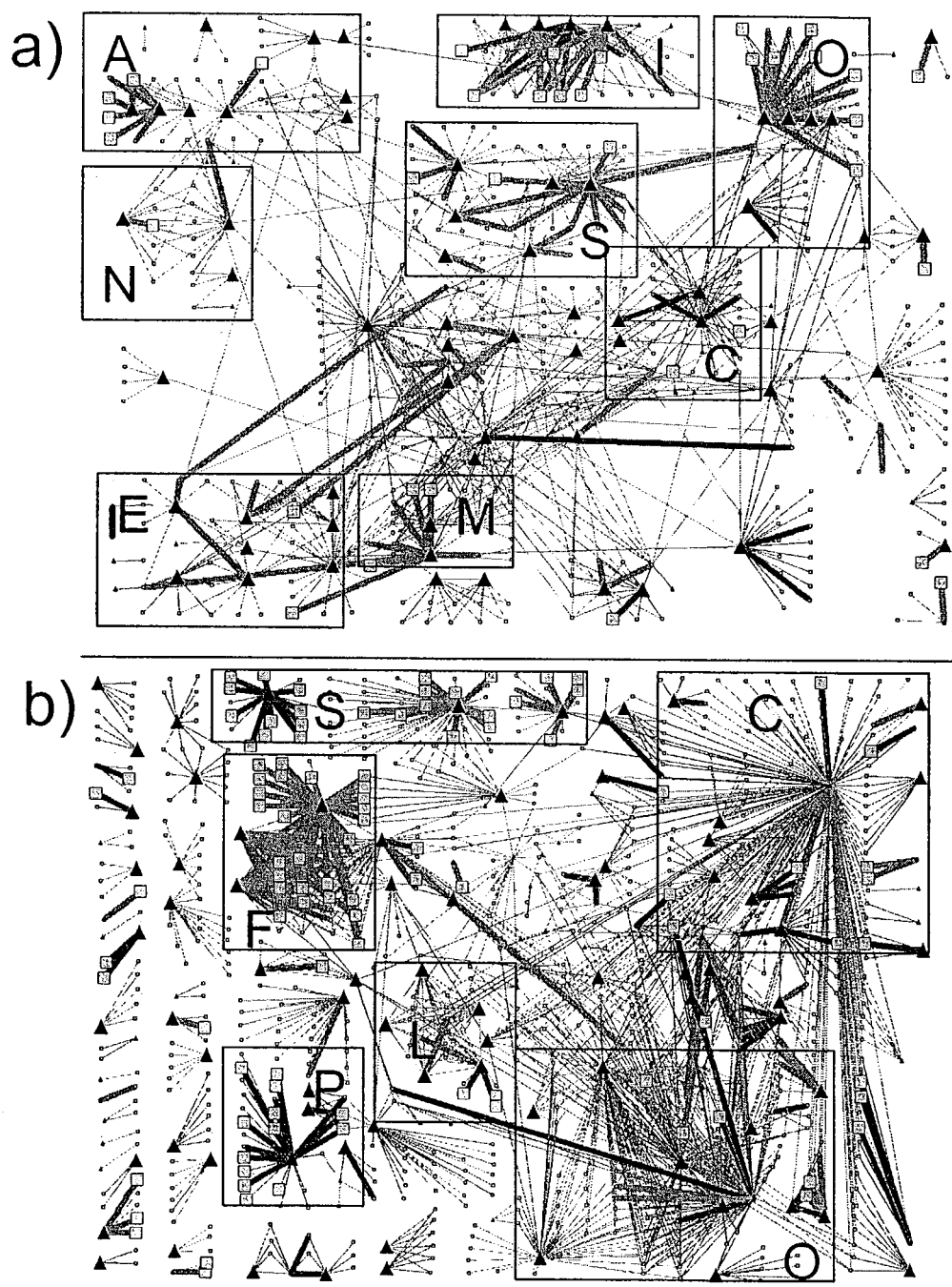
FIG. 16 shows the reconciliation of legacy and empirical data sets for regulatory networks of yeast and E. coli.
Figure 17:
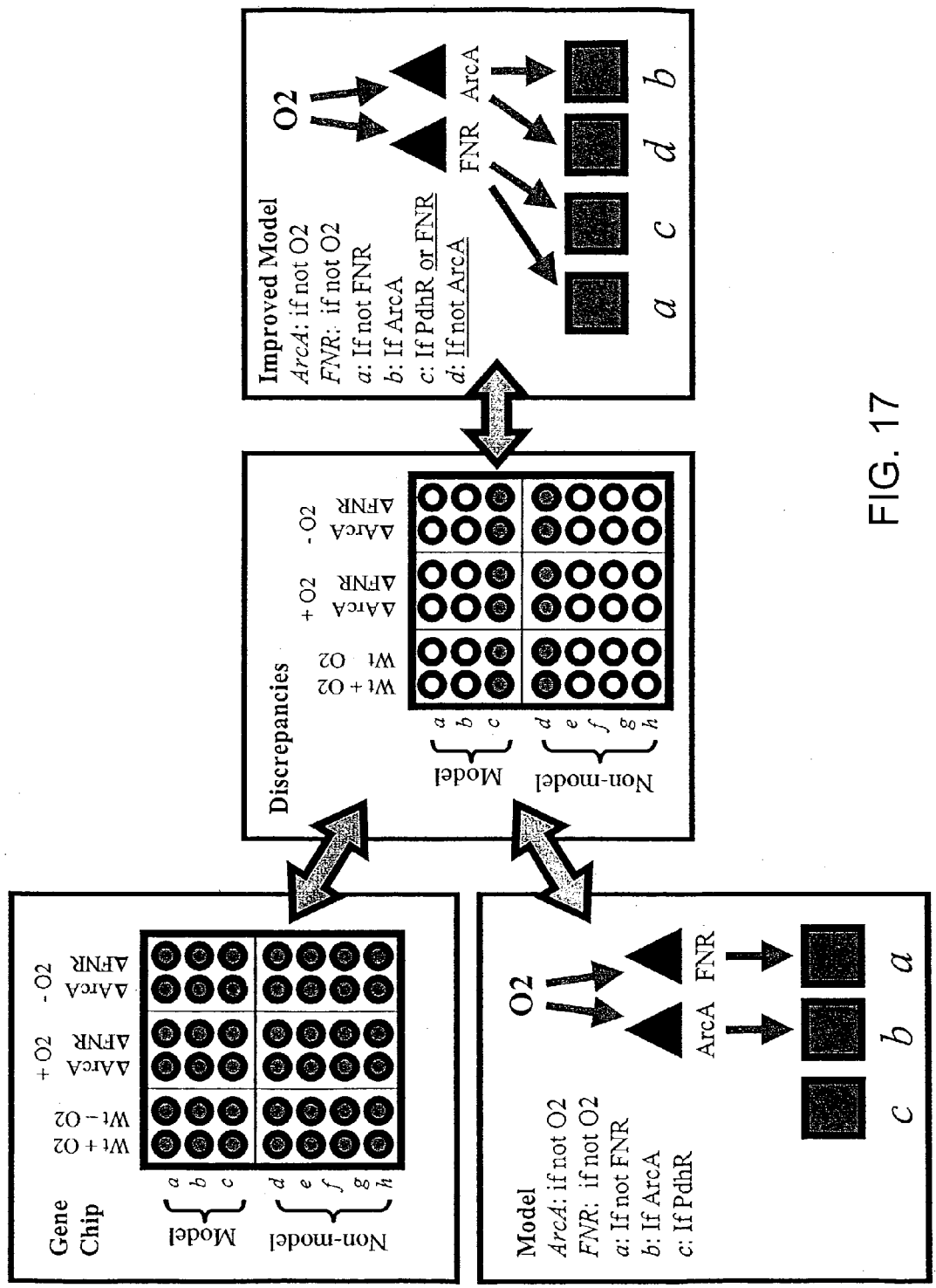
FIG. 17 shows a schematic diagram of an algorithm for reconciliation of data sets and iterative improvement of a mathematical or in silico model.

All the results described above for both yeast and E. coli can be displayed on a map of the regulatory network (FIG. 16). This data display allows identifying subcomponents of the networks that have high degree of agreement with the gene expression data sets analyzed. For example in yeast the nitrogen utilization (I in FIG. 16a) and oxygen response (O) systems have many highly consistent elements, but the elements in the carbon utilization (C) network are generally not consistent with the gene expression data. Similarly in E. coli components such as the flagellar biosynthesis network (F in FIG. 16b) are highly consistent, but the carbon utilization (C) network again does not have many consistent network elements.

Some of the variability in consistency between regulatory network structures and gene expression data appears to be due to the types of data sets utilized in this work. For example, the DNA repair system in E. coli was specifically activated in one of the gene expression data sets and the response to nitrogen depletion was studied in one of the yeast data set. However, there are also general network structural features that appear to influence consistency. The most prominent feature is the tendency of relatively isolated subcomponents of the network such as flagellar biosynthesis in E. coli or nitrogen utilization in yeast to be consistent with gene expression data whereas highly interconnected components such as carbon utilization regulation are typically inconsistent. However, not every isolated sub-network is consistent indicating that the network reconstruction may be incomplete and these subnetworks may in fact be more strongly connected to other parts of the network than is currently known.

Taken together, the results shown here indicate that combining information on known regulatory network structures with gene expression data is a productive way to validate and expand regulatory networks structures. It is important to note that, because the overall level of consistency was generally found to be low, genome-scale reconstruction of regulatory networks based on gene expression data alone does not appear to be feasible, even if large quantities of data is available as is the case for yeast. The results show that different features of the network structure influence consistency. In particular, we observe that network elements involving repressors (pair-wise interactions, regulons) are typically less consistent than those involving activators indicating that reconstruction of these types of network components would pose a challenge. Further, in yeast TRUs with four regulators are generally more consistent than other types of TRUs indicating that in such cases the known network structure appears to be sufficiently complete whereas for the TRUs with fewer regulators there may be regulators missing. The discovery of highly consistent network subcomponents indicates that a gene expression data based reconstruction of regulatory networks can be a powerful strategy for particular subcomponents that are sufficiently isolated and for which sufficient quantities of relevant data is available. Future availability of other high-throughput data types such as genome-wide DNA-binding site occupancy data (Ren, B. et al. Science 290:2306-9. (2000)) will further improve the prospects of such reconstruction as additional data types can be used to resolve inconsistencies. The full utilization of all high-throughput data types, however, will require the combination prior biological knowledge extracted from databases and literature with the statistical analysis of the large-scale data sets. Thus, full reconstruction of regulatory networks will rely on a combination of 'bottom-up' and 'top-down' approaches with targeted prospective experimentation to successively resolve inconsistencies between the two. Ultimately, all such data types are expected to be reconciled in the context of genome-scale in silico models of regulatory networks that can be used to analyze, interpreted and ultimately predict their function.

EXAMPLE V

Iterative Refinement of a Regulatory Network Model

The purpose of this example is to illustrate how the methods described can be used for regulatory network identification, improvement and the identification of regulatory states in regulatory or combined regulatory/metabolic models.

The "bottom-up" approach to genome-scale transcriptional regulatory network model reconstruction is initiated by incorporation of knowledge into a computational model to analyze, interpret and predict phenotype. The process begins with first pass reconstruction of metabolic and transcriptional regulatory networks for the organism of interest. Reconstruction of such genome-scale models has been described elsewhere in detail (Covert M W, Schilling C H, Famili I, Edwards J S, Goryanin I I, Selkov E, Palsson B O. Trends Biochem Sci 26:179-86 (2001); Covert M W, Schilling C H, Palsson B. J Theor Biol 213:73-88 (2001)) and leads to the representation of metabolic behavior as a linear programming problem, with a matrix describing all known metabolic reactions, and certain measured parameters (e.g., maximum uptake rates, biomass composition) defined as constraints on the metabolic system. Transcriptional regulatory behavior is represented as a set of regulatory rules written as Boolean logic statements. These rules are dependent on environmental and internal conditions and determine the expression and/or repression of various metabolic genes in the metabolic network.

The regulatory and metabolic models are integrated as the outcomes of the logic statements impose time-dependent constraints on the metabolic linear programming problem. The outcome of the linear programming problem is then used to recalculate environmental conditions (Varma A, Palsson B O, Appl Environ Microbiol. 60:3724-31 (1995); Covert M W, Schilling C H, Palsson B. J Theor Biol. 213:73-88 (2001)), and the Boolean logic equations are reevaluated.

The Boolean logic rules are derived from the primary literature to represent the conditions required for expression of a particular gene or set of genes. Experimental studies are examined to obtain a set of potential transcription factors for all known promoters of expression of a particular target gene. The presence of multiple promoters from which transcription may occur indicates an OR relationship, and the presence of two interacting transcription factors which effect one promoter indicates an AND relationship. For example, if gene A has two promoters, one of which is activated by transcription factor X and the other which is repressed by the integrated product of transcription factors Y and Z, then a rule may be derived which states that A is transcribed IF (X) OR NOT (Y AND Z).

Such a model is in process of being built for E. coli. For this organism, a genome-scale metabolic network model had already been reconstructed (Edwards J S, Palsson B O, Proc Natl Acad Sci U S A. 97:5528-33 (2000)). The regulatory network model was first implemented for core metabolic processes. The first combined metabolic/regulatory model accounts for 149 genes, the products of which include 16 regulatory proteins and 73 enzymes. These enzymes catalyze 113 reactions, 45 of which are controlled by transcriptional regulation. The combined metabolic/regulatory model can predict the ability of mutant E. coli strains to grow on defined media, as well as time courses of cell growth, substrate uptake, metabolic by-product secretion and qualitative gene expression under various conditions, as indicated by comparison to experimental data under a variety of environmental conditions. The in silico model may also be used to interpret dynamic behaviors observed in cell cultures (Covert M W, Palsson B O. J Biol Chem 277:28058-64 (2002)).

When integrated as mentioned above, the regulatory/metabolic models represent a first-pass reconstruction and may be used for the generation of testable hypotheses (see FIG. 16). First, a phenotypic or behavioral shift of interest must be specified for a particular organism (e.g., glucose-lactose diauxie in E. coli), as well as important regulatory genes. The regulatory/metabolic model may then be used to simulate behavior of the wild type strain over the course of the shift, as well as behavior of knockout and/or mutant strains of the relevant regulatory genes. These simulations represent hypotheses about the growth behavior, substrate uptake, by-product secretion, and gene expression over the course of the shift for each strain.

Strains of the organism are then obtained and/or constructed to build a full complement of the wild type as well as all corresponding knockout strains. Each strain is then cultured to monitor experimentally the shift in question. Rates of growth, uptake and secretion as well as gene expression are monitored over the course of the shift using practices that are well known in the art (Ideker T, Thorsson V, Ranish J A, Christmas R, Buhler J, Eng J K, Bumgarner R, Goodlett D R, Aebersold R, Hood L. Science 294:929-34 (2001)).

Once the necessary experimental data has been obtained, the experimental outcomes are compared rigorously to the computationally-generated data. This comparison will lead to (1) validation of certain regulatory relationships described by the model; (2) the identification of regulatory relationships included in the model but for which the experimental results were contradictory; and (3) the identification of regulatory relationships which were not previously known which must be incorporated into the model. Both (2) and (3) represent areas where the model may be improved.

Many genes are regulated by more than one transcription factor in certain organisms. Such genes correspond to complex Boolean logic rules, which must obtained by further experimentation. Specifically, for genes which are shown by the process above to be regulated by more than one transcription factor, the multiple knockout strains may be constructed, in which to determine complex interactions. If two transcription factors are required to affect the regulation of a gene, they have an AND relationship; if only one factor is required they have an OR relationship.

The method is applied to the study of anaerobiosis in E. coli (FIG. 16). A large-scale model of metabolism and transcriptional regulation was generated for E. coli previously (Covert M W, Palsson B O, J Biol Chem 277:28058-64 (2002)). This model will be built up to the genome-scale (currently in progress) and used to generate predictions about growth, uptake and secretion rates as well as gene expression of E. coli under conditions of aerobic and anaerobic growth in glucose minimal media. Six strains—the appY, soxS, oxyR, fnr and arcA knockout strains as well as the wild type—will be grown in batch culture as described above, with growth, uptake and secretion monitored continually. A sample will be taken at mid-log phase from which the mRNA will be extracted and analyzed using Affymetrix Gene Chip technology. From this data, the model will be evaluated both in terms of regulation (e.g., its ability to predict gene induction/repression) and metabolism (e.g., its ability to predict growth behavior of the wild type and mutant strains). This information will then be used to iteratively improve the model in terms of anaerobiosis prediction.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

EXAMPLE VI

Iterative Refinement of a Regulatory Network Model Via a Systematic Model Improvement Algorithm The purpose of this example is to illustrate the importance of the systematic approach described above and depicted in FIG. 2b to converge quickly on the best model of a biological process. Although a hypothetical regulatory network is used here as an example, this process is equally applicable to metabolic networks, signaling pathways, protein interaction networks and any other biological processes.

Figure 18:
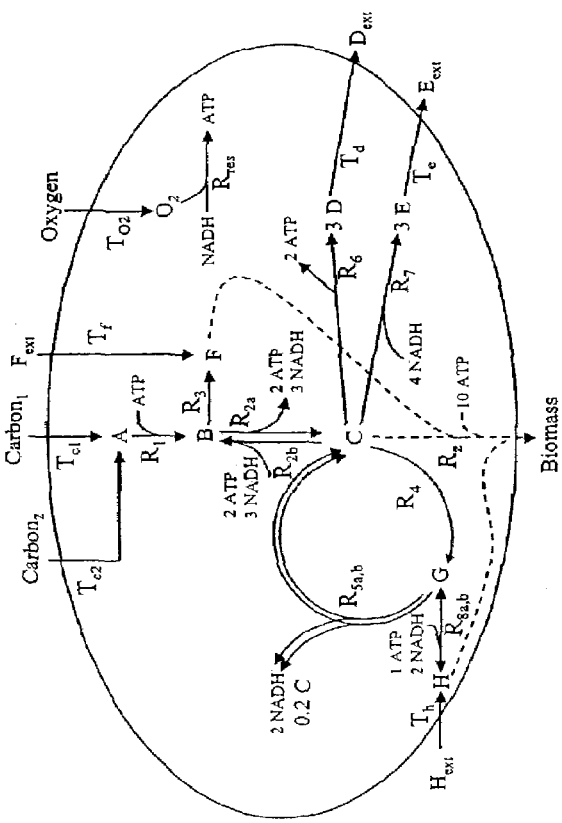
FIG. 18 shows a skeleton network of core metabolism and regulation, together with a table containing relevant chemical reactions and regulatory rules which govern the transcriptional regulation.

A skeleton network of core metabolism was formulated earlier (Covert M W, Schilling C H, Palsson B. J Theor Biol. 213:73-88 (2001)). It includes 20 reactions, 7 of which are governed by regulatory logic. This network is a highly simplified representation of core metabolic processes (e.g. glycolysis, the pentose phosphate pathway, TCA cycle, fermentation pathways, amino acid biosynthesis and cell growth), along with corresponding regulation (e.g. catabolite repression, aerobic/anaerobic regulation, amino acid biosynthesis regulation and carbon storage regulation). A schematic of this skeleton network is shown in FIG. 18, together with a table containing all of the relevant chemical reactions and regulatory rules which govern the transcriptional regulation. In terms of FIG. 2b, this network will be considered the actual experimental system which is to be characterized.

To the right of the experimental system in FIG. 18 is the model of the experimental system. The model is fairly complete, with one exception: the regulation of R5a in the model has not been correctly characterized, with no regulatory rule given (i.e., the reaction is expressed under all conditions).

A statement of scope and accuracy is determined for the model; namely, that the model will model the entire transcriptional regulatory component of the system qualitatively, using Boolean logic, where a "1" indicates that the gene corresponding to a given reaction has been expressed and a "0" indicates that the gene has been down-regulated. The experiments of interest are growth of the system on metabolite Carbon2 under aerobic and anaerobic conditions. For this example, the criterion for the desired accuracy of the model is that the model error, calculated as the sum of the squared difference between the observed and predicted expression of all regulated genes in the system, is equal to zero.

In Phase I of the process, an experiment is run with Carbon2 and Oxygen available to the system. The expression of the regulated genes in the experimental and model system are calculated and shown in FIG. 19. The model error is equal to zero in this case, indicating that the experimental data and the model predictions agree completely in this case.

Next, an experiment is run with Carbon2, but not Oxygen, available to the system. In this case, there is a discrepancy between the observed and calculated expression of T5a, resulting in an error of one. Because the model error is greater than allowed by the stated criterion, a procedure is implemented to alter the composition of the mathematical model in such a way that the model error is minimized under the given experimental conditions. The procedure used in this case is developed with the following assumption: the regulation of T5a depends on only one of the known regulatory proteins (RPc1, RPb, RPh, and RPO2) in the system. The procedure is therefore as follows: (1) Obtain the activity of each protein as predicted by the model, (2) for each protein, generate a rule based on the activity of the given protein which results in the correct expression value for T5a, (3) recalculate the overall expression array for the regulated genes, (4) evaluate the difference between the criterion for model accuracy by determining the new model error, and (5) choose the model(s) with the lowest error as the new model for future iterations.

Figure 19:
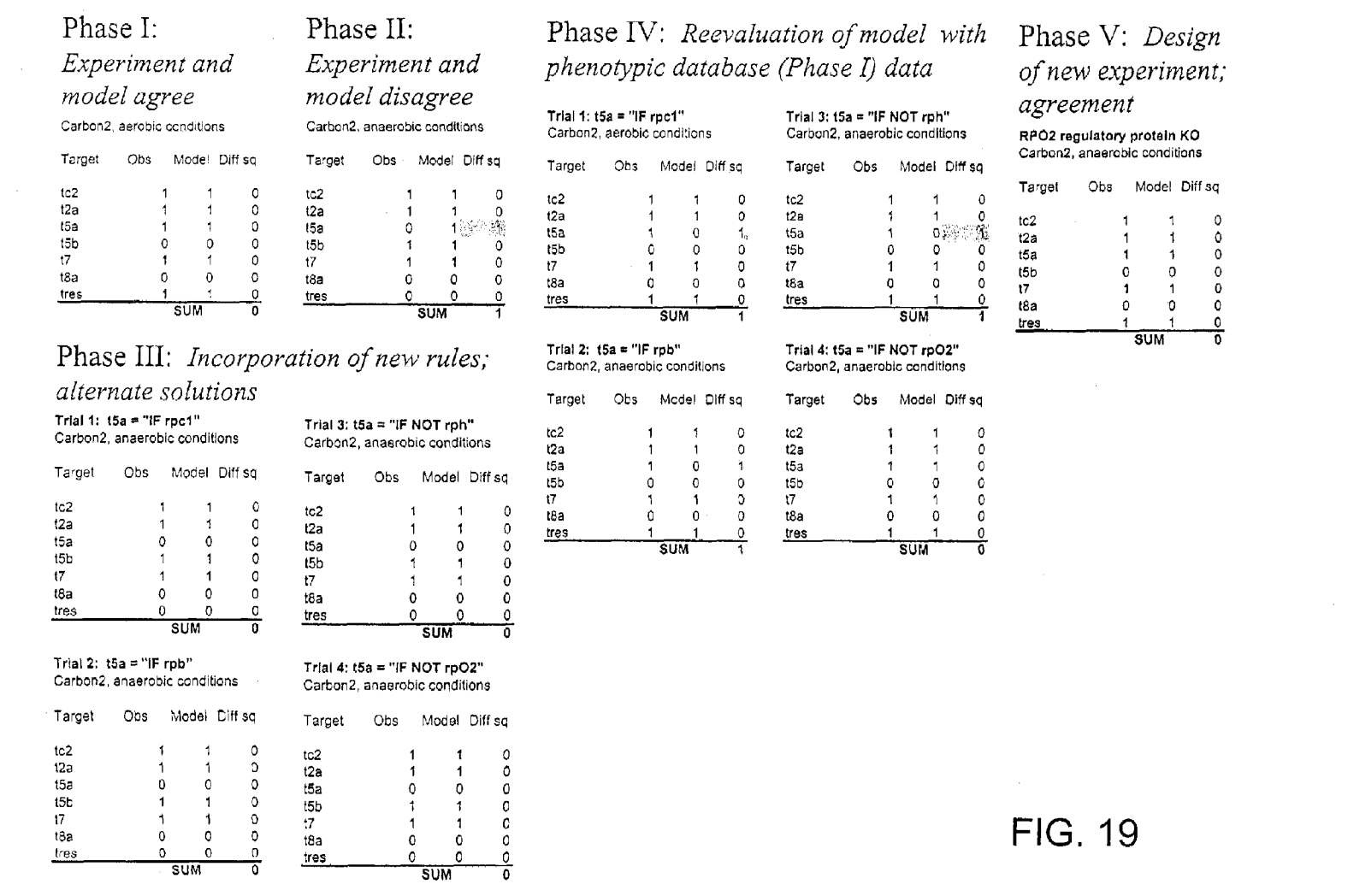

The activity of the regulatory proteins under the given conditions are: RPc1=0, RPb=0, RPh=1, RPO2=1. For T5a to have a value of zero, the rules which could be implemented are therefore: T5a =IF (RPc1), T5a=IF (RPb), T5a=IF NOT (RPh), and T5a=IF NOT (RPO2). The error of the model is calculated with each new rule; and the new models all have an error of zero, as shown in FIG. 19 (Phase III). As a result, one of the models (with new rule T5a=IF (RPc1); for example) is picked arbitrarily and the other equivalent solutions are stored.

The new model may then be reevaluated with data in the Phenotypic database. For this example, data from the experiment where Carbon2 and Oxygen were available to the system is compared to the predictions of the new model. The new model has an error with respect to these conditions (shown in Phase IV of FIG. 19); as the other alternative solutions are considered, only the model with new rule T5a=IF NOT (RPO2) fits the data with zero error. This model is kept for future iterations.

The process suggests a new experiment to further characterize the regulatory network: specifically, creating a RPO2 knockout strain of the system and testing the ability of the knockout strain to grow where Carbon2 is available but Oxygen is not. As shown in FIG. 19, the model predictions and experimental data are also in agreement for this experiment.

The model has therefore been used to drive an experimental process where new data has been generated to improve model predictions and better characterize the experimental system itself, as well to suggest a new round of experiments which can be performed to gain further knowledge and insight.

EXAMPLE VII

Decomposing Steady State Flux Distributions into Extreme Pathways Using the Alpha-Cone Method This example shows how an arbitrary steady state phenomenological flux distribution can be decomposed in a principled fashion into systemic pathways (here extreme pathways) to identify operational pathways in a biosystem. The alpha-cone decomposition method allows identifying the range of systemic pathway weightings for a given flux distribution as well as defining the minimal set of systemic pathways required to describe a phenomenological pathway. This minimal set of systemic pathways together with the range of possible weightings of these pathways defines the operational pathways of the biosystem.

The sample metabolic network used for this analysis has been published previously (Covert M W, Schilling C H, Palsson B. J Theor Biol 213:73-88 (2001)). The network consists of 20 reactions and 16 internal metabolites. The example network was designed to mirror some of the core metabolic processes such as glycolysis, the citric acid cycle, and respiration. The extreme pathways of this network were calculated previously (Covert M W & Palsson B O. J Theor Biol 216 (2003)). The network has 80 Type I extreme pathways that are included in this analysis. Each extreme pathway, pi, was scaled to its maximum possible flux based on the maximum value of the uptake reactions ($V_{max}$). A matrix P is then formed using $p_i$ (i=1 . . . n, where n is the number of extreme pathways for the system) as its columns.

To mimic phenomenological flux distributions produced by experimental measurements the steady state flux distributions for this network were calculated using the well-established technique of flux balance analysis (FBA). For the purposes of this study, unique steady state flux distributions were calculated for various environmental conditions.

For a given phenomenological flux distribution the decomposition weightings on the extreme pathways (denoted by α) are not usually unique. The rank of the P matrix determines the number of consistent equations and is usually smaller than the number of extreme pathways, resulting in extra degrees of freedom. This results in an "alpha space" of allowable extreme pathway weightings. In order to elucidate the range of possible alpha values that could contribute to the steady state solution, the alpha-spectrum was developed based on the equation P.α=v where P is a matrix of extreme pathway vectors (extreme pathways are the columns, reactions are the rows), α is a vector of alpha weightings on the pathways and v an arbitrary steady state flux distribution that is to be decomposed. For each individual extreme pathway defined for the network, the alpha weighting for that pathway was both maximized and minimized using linar programming while leaving all other extreme pathway alpha weightings free. This resulted in an allowable alpha range for each extreme pathway. The results were then plotted on a 2-dimensional graph with the extreme pathways on the x-axis and the range of alpha weightings on the y-axis. Since the pathways are normalized to $V_{max}$, the alpha weightings correspond to a percentage usage of each extreme pathway. Some extreme pathways are not used while others can have a range of alpha weightings.

In addition to defining the alpha-spectrum, mixed integer linear programming (MILP) (Williams, H P Model building in mathematical programming. Chichester; N.Y., Wiley (1990)) was used to find the minimum number of extreme pathways that were needed to describe a given phenomenological flux distribution in cases where multiple pathway combinations exist. The usage of a specific extreme pathway was represented by a Boolean variable $\beta_j$ which was assumed to have a value of 1 when the corresponding pathway is used and zero when the pathway is not used. The sum of all Boolean variables representing pathway usage was minimized to obtain the alpha weightings corresponding to the case where the least number of pathways was used. The corresponding optimization problem can be formally described as:

$$\text{Min} \sum_{i=1}^{n_p} \beta_i$$

where β is the vector of the Boolean variables corresponding to the pathway usage and α is the vector of the pathway weightings. The solution is a set of alpha weightings such that the minimum number of extreme pathways are used to obtain the decomposition of the desired phenomenological flux distribution.

The methods described above were applied to the case of aerobic growth with no regulation included. This case was essentially unrestricted as all possible substrates (Carbon 1, Carbon 2, F, H, and Oxygen) were provided to the network.

Figure 20:
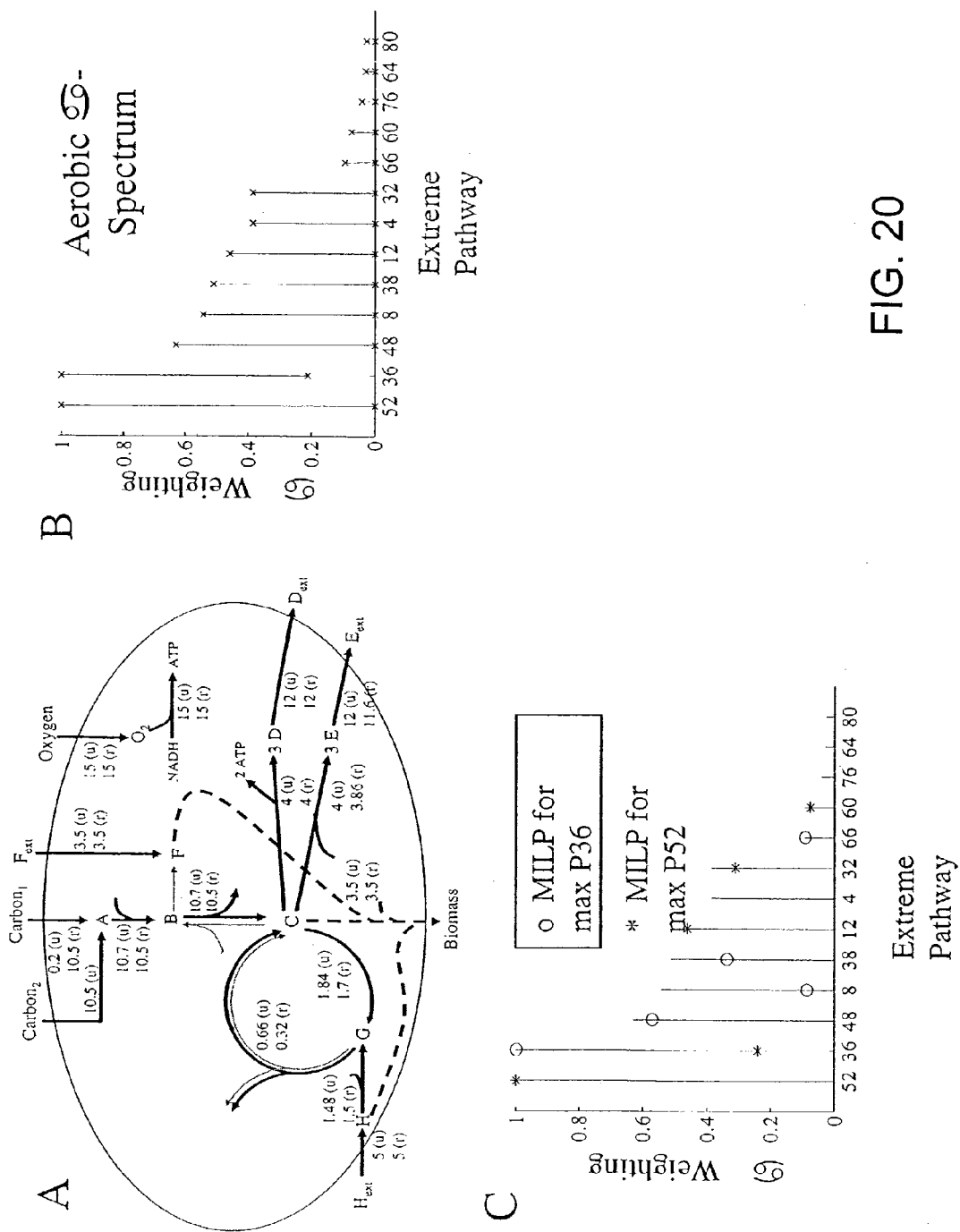
FIG. 20 shows computed flux distributions using flux balance analysis (FBA) for the aerobic growth without regulation using an in silico model of the invention.

The resulting flux distribution computed using FBA can be seen in FIG. 20A. The calculated alpha-spectrum shows that of the 80 Type I pathways, only 13 could be used in reconstructing the aerobic flux distribution (FIG. 20B). Pathway 52 can range from 0 to 1 (0 to 100% of its maximum possible usage). Pathway 36 must be used as indicated by the non-zero minimum alpha value. The remaining 11 pathways vary from 0 to various sub-maximum values. An MILP analysis was done to determine the minimum number of pathways needed to produce the aerobic steady state flux distribution. When the MILP was solved without additional constraints, P36 was used to its maximum capacity (100%) with sub-maximal contributions from pathways 48, 38, 66, and 8. Interestingly, when the network was forced to maximally use the pathway with the greatest alpha range (P52), pathway 36 was also used, albeit sub-maximally, along with pathways 12, 32, and 60. Note that with the exception of P36, which has a non-zero minimum possible weighting and thus has to be used in all possible solutions, there are no pathways in common between the two sets of MILP solutions (FIG. 20C).

While the alpha-cone method was demonstrated above for a flux distribution obtained through an FBA calculation, it is be possible to use experimentally determined metabolic flux data in the analysis as well. Even given partial or fragmented flux data, it will be possible to determine the candidate alpha-spectrum and hence obtain the operational pathways active in a cell in a given external condition.

| Enzyme | Reaction/Gene Name | Reaction |
|---|---|---|
| Membrane Transport | | |
| Phosphotransferase system | pts | GLCxt + PEP → G6P + PYR |
| Succinate transport | SUCC trx | SUCCxt ↔ SUCC |
| Acetate transport | AC trx | ACxt ↔ AC |
| Ethanol transport | ETH trx | ETHxt ↔ ETH |
| Oxygen transport | O2 trx | O2xt ↔ O2 |
| Carbon dioxide transport | CO2 trx | CO2xt ↔ CO2 |
| Phosphate transport | Pi trx | PIxt ↔ PI |
| Glycolysis | | |
| Phosphoglucose isomerase | pgi | G6P ↔ F6P |
| Phosphofructokinase | pfkA | F6P + ATP → FDP + ADP |
| Fructose-1,6-bisphosphatase | fbp | FDP → F6P + PI |
| Fructose-1,6-bisphosphatate aldolase | fba | FDP ↔ T3PI + T3P2 |
| Triosphosphate Isomerase | tpiA | T3P2 ↔ T3PI |
| Glyceraldehyde-3-phosphate dehydrogenase | gapA | T3PI + PI + NAD → NADH + 13PDG |
| Phosphoglycerate kinase | pgk | 13PDG + ADB → 3PG + ATP |
| Phosphoglycerate mutase 1 | gmpA | 3PG ↔ 2PG |
| Enolase | eno | 2PG ↔ PEP |
| Pyruvate Kinase II | pykA | PEP + ADP → PYR + ATP |
| Phosphoenolpyruvate synthase | ppsA | PYR + ATP → PEP + AMP + PI |
| Pyruvate dehydrogenase | aceE | PYR + COA + NAD → NADH + CO2 + ACCOA |

-continued

| Enzyme | Reaction/Gene Name | Reaction |
|---|---|---|
| Pentose Phosphate Shunt | | |
| Glucose 6-phosphate-1-dehydrogenase | zwf | G6P + NADP ↔ D6PGL + NADPH |
| 6-Phosphogluconolactonase | pgl | D6PGL → D6PGC |
| 6-Phosphogluconate dehydrogenase | gml | D6PGC + NADP ↔ NADPH + CO2 + RL5P |
| Ribose-5-phophate isomerase A | rpiA | RL5P ↔ R5P |
| Ribulose phosphate-3-epimerase | rpe | RL5P ↔ X5P |
| Transketolase I | tktAI | R5P + X5P ↔ T3PI + S7P |
| Transaldolase B | talA | T3PI + S7P ↔ E4P + F6P |
| Transketolase II | tktA2 | X5P + E4P ↔ F6P + T3PI |
| TCA cycle | | |
| Citrate synthase | gltA | ACCOA + AO → COA + CIT |
| Aconitase A | acnA | CIT ↔ ICIT |
| Icositrate dehydrogenase | icdA | ICIT + NADP ↔ CO2 + NADPH + AKR |
| 2-Ketoglutarate dehydrogenase | sucA | AKG + NAD + COA → CO2 + NADH + SUCCOA |
| Succinyl-CoA synthetase | sucC | SUCCOA + ADP + PI ↔ ATP + COA + SUCC |
| Succinate dehydrogenase | sdhAI | SUCC + FAD → FADH + FUM |
| Fumarate reductase | frdA | FUM + FADH → SUCC + FAD |
| Fumarase A | fumA | FUM ↔ MAL |
| Malate dehydrogenase | mdh | MAL + NAD → NADH + OA |
| Dissimilation of Pyruvate | | |
| Acetaldehyde dehydrogenase | adhE | ACCOA + 2 NADH ↔ ETH + 2 NAD + COA |
| Phosphotransacetylase | pta | ACCOA + PI ↔ ACTP + COA |
| Acetate kinase A | ackA | ACTP + ADP ↔ ATP + AC |
| Anapleurotic Reactions | | |
| Phosphoenolpyruvate carboxykinase | pckA | OA + ATP → PEP + CO2 + ADP |
| Phosphoenolpyruvate carboxylase | ppc | PEP + CO2 → OA + PI |
| Energy/Redox Metabolism | | |
| NADH dehydrogenase I | nuoA | NADH + Q → NAD + QH2 + 2 HEXT |
| Cytochrome oxidase bo3 | cyoA | QH2 + 1/2 O2 → Q + 2 HEXT |
| Pyridine nucleotide transhydrogenase | pntA | NADPH + NAD → NADP + NADH |
| Succinate dehydrogenase complex | sdhA2 | FADH + Q → FAD + QH2 |
| F0F1-ATPase | atpABCDEFGHI | ADP + PI + 3 HEXT → ATP |
| Adenylate kinase | adk | ATP + AMP ↔ 2 ADP |
| ATP drain | ATP_dr | ATP → ADP + PI |
| Growth Flux | | |
| Growth flux | GRO | 41.3 ATP + 3.5 NAD + 18.2 NADPH + 0.2 G6P + 0.1 F6P + 0.9 R5P + 0.4 E4P + 0.1 T3PI + 1.5 3PG + 0.5 PEP + 2.8 PYR + 3.7 ACCOA + 1.8 OA + 1.1 AKG → 41.3 ADP + 41.3 PI + 3.5 NADH + 18.2 NADP + 3.7 COA + 1.0 BIOMASS |
| Exchange Fluxes | | |
| Glucose external | GLCxt | GLCxt→ |
| Succinate external | SUCCxt | SUCCxt→ |
| Ethanol external | ETHxt | ETHxt→ |
| Acetate external | ACxt | ACxt→ |
| Biomass drain | BIOMASS | BIOMASS→ |
| Phosphate external | PIxt | PIxt→ |
| Carbon dioxide external | CO2xt | CO2xt→ |
| Oxygen external | O2xt | O2xt→ |

TABLE 2

| | Exchange Fluxes | | | | | | | |
|---|---|---|---|---|---|---|---|---|
| Pathway Number | SUCCxt/ SUCCxt | ETHxt/ SUCCxt | ACxt/ SUCCxt | GRO/ SUCCxt | PIxt/ SUCCxt | CO2xt/ SUCCxt | O2xt/ SUCCxt | Net Pathway Reaction Balance |
| 33 | −1.000 | 0 | 0 | 0.051 | −0.188 | 1.825 | −1.267 | SUCCxt + 0.188 PIxt + 1.267 O2xt ---> 0.051 GRO + 1.825 CO2xt |
| 30 | −1.000 | 0 | 0 | 0.034 | −0.125 | 2.553 | −2.014 | SUCCxt + 0.125 PIxt + 2.014 O2xt ---> 0.034 GRO + 2.553 CO2xt |
| 32 | −1.000 | 0 | 0 | 0.033 | −0.121 | 2.600 | −2.062 | SUCCxt + 0.121 PIxt + 2.062 O2xt ---> 0.033 GRO + 2.6 CO2xt |
| 34 | −1.000 | 0 | 0 | 0.049 | −0.182 | 1.895 | −1.338 | SUCCxt + 0.182 PIxt + 1.338 O2xt ---> 0.049 GRO + 1.895 CO2xt |
| 22 | −1.000 | 0 | 0 | 0.032 | −0.117 | 2.644 | −2.108 | SUCCxt + 0.117 PIxt + 2.108 O2xt ---> 0.032 GRO + 2.644 CO2xt |
| 14 | −1.000 | 0 | 0 | 0.031 | −0.114 | 2.679 | −2.144 | SUCCxt + 0.114 PIxt + 2.144 O2xt ---> 0.031 GRO + 2.679 CO2xt |
| 18 | −1.000 | 0.549 | 0 | 0.025 | −0.092 | 1.837 | −0.759 | SUCCxt + 0.092 PIxt + 0.759 O2xt ---> 0.025 GRO + 1.837 CO2xt + 0.549 ETHxt |
| 31 | −1.000 | 0 | 0.158 | 0.047 | −0.172 | 1.696 | −1.142 | SUCCxt + 0.172 PIxt + 1.142 O2xt ---> 0.047 GRO + 1.696 CO2xt + 0.158 ACxt |

TABLE 2-continued

| Pathway Number | Exchange Fluxes | | | | | | | Net Pathway Reaction Balance |
|---|---|---|---|---|---|---|---|---|
| | SUCCxt/ SUCCxt | ETHxt/ SUCCxt | ACxt/ SUCCxt | GRO/ SUCCxt | PIxt/ SUCCxt | CO2xt/ SUCCxt | O2xt/ SUCCxt | |
| 10 | −1.000 | 0 | 0 | 0 | 0 | 4.000 | −3.500 | SUCCxt + 3.5 O2xt ---> 4.0 CO2xt |
| 5 | −1.000 | 0 | 1.000 | 0 | 0 | 2.000 | −1.500 | SUCCxt + 1.5 O2xt ---> 2.0 CO2xt + 1.0 ACxt |
| 2 | −1.000 | 1.000 | 0 | 0 | 0 | 2.000 | −0.500 | SUCCxt + 0.5 O2xt ---> 2.0 CO2xt + 1.0 ETHxt |
| 26 | −1.000 | 0 | 0 | 0 | 0 | 4.000 | −3.500 | SUCCxt + 3.5 O2xt ---> 4.0 CO2xt |

TABLE 3

| Angles (degree) | Pathway # | Diff Fluxes (%) | Pathway # | Net Diff (%) | Pathway # |
|---|---|---|---|---|---|
| 4.62E−05 | P_33 | 0 | P_33 | 5.84E−05 | P_33 |
| 4.9 | P_32 | 3.5 | P_34 | 11.3 | P_32 |
| 11.1 | P_30 | 5.3 | P_22 | 22.4 | P_30 |
| 22.6 | P_31 | 5.3 | P_30 | 36.8 | P_31 |
| 25.2 | P_34 | 8.8 | P_14 | 67.1 | P_2 |
| 26.1 | P_22 | 8.8 | P_31 | 67.8 | P_34 |
| 27.0 | P_14 | 10.5 | P_32 | 70.7 | P_5 |
| 27.7 | P_18 | 14.0 | P_18 | 72.2 | P_22 |
| 38.8 | P_10 | 22.8 | P_26 | 76.3 | P_14 |
| 40.1 | P_5 | 38.6 | P_10 | 79.6 | P_18 |
| 40.4 | P_26 | 52.6 | P_2 | 177.0 | P_10 |
| 41.5 | P_2 | 52.6 | P_5 | 233.1 | P_26 |

TABLE 4

| Angles (degree) | Pathway # | Diff Fluxes (%) | Pathway # | Net Diff (%) | Pathway # |
|---|---|---|---|---|---|
| 2.3 | P_32 | 3.5 | P_32 | 5.2 | P_32 |
| 2.6 | P_33 | 7.0 | P_33 | 6.4 | P_33 |
| 10.9 | P_30 | 10.5 | P_34 | 25.1 | P_30 |
| 21.9 | P_31 | 12.3 | P_22 | 35.8 | P_31 |
| 25.9 | P_34 | 12.3 | P_30 | 66.9 | P_2 |
| 26.9 | P_22 | 15.8 | P_14 | 71.4 | P_5 |
| 27.8 | P_14 | 15.8 | P_31 | 75.3 | P_34 |
| 28.4 | P_18 | 21.1 | P_18 | 79.9 | P_22 |
| 39.5 | P_10 | 29.8 | P_26 | 84.1 | P_14 |
| 39.5 | P_5 | 45.6 | P_10 | 87.5 | P_18 |
| 40.5 | P_26 | 45.6 | P_5 | 187.6 | P_10 |
| 41.0 | P_2 | 59.6 | P_2 | 241.7 | P_26 |

TABLE 5

| Variant | Type | Nucleotide Change | Amino Acid Change | Result |
|---|---|---|---|---|
| B+ | normal | none | none | |
| A+ | non-chronic | 376 A → G | Asn → Asp | polar to acidic |
| A− | non-chronic | 376 A → G | Asn → Asp | polar to acidic |
| | | 202* G → A | Val → Met | nonpolar to nonpolar |
| Mediterranean | non-chronic | 563 C → T | Ser → Phe | polar to nonpolar |
| Tsukui | chronic | 561-563 del | 188/189 del | |
| Minnesota | chronic | 637 G → T | 213 Val → Leu | nonpolar to nonpolar |
| Asahikawa | chronic | 695 G → A | 232 Cys → Tyr | slightly polar to nonpolar |
| Durham | chronic | 713 A → G | 238 Lys → Arg | basic to basic |
| Wayne | chronic | 769 C → G | 257 Arg → Gly | basic to nonpolar |
| Loma Linda | chronic | 1089 C → A | 363 Asn → Lys | polar to basic |
| Tomah | chronic | 1153 T → C | 385 Cys → Arg | slightly polar to basic |
| Iowa | chronic | 1156 A → G | 386 Lys → Glu | basic to acidic |
| Walter Reed | chronic | 1156 A → G | 386 Lys → Glu | basic to acidic |
| Iowa City | chronic | 1156 A → G | 386 Lys → Glu | basic to acidic |
| Springfield | chronic | 1156 A → G | 386 Lys → Glu | basic to acidic |
| Guadalajara | chronic | 1159 C → T | 387 Arg → Cys | basic to slightly polar |
| Iwate | chronic | 1160 G → A | 387 Arg → His | basic to acidic/basic |
| Niigata | chronic | 1160 G → A | 387 Arg → His | basic to acidic/basic |
| Yamaguchi | chronic | 1160 G → A | 387 Arg → His | basic to acidic/basic |
| Portici | chronic | 1178 G → A | 393 Arg → His | basic to acidic/basic |
| Alhambra | chronic | 1180 G → C | 394 Val → Leu | nonpolar to nonpolar |
| Tokyo | chronic | 1246 G → A | 416 Glu → Lys | acidic to basic |
| Fukushima | chronic | 1246 G → A | 416 Glu → Lys | acidic to basic |
| Atlanta | chronic | 1284 C → A | 428 Tyr → End | |
| Pawnee | chronic | 1316 G → C | 439 Arg → Pro | basic to nonpolar |
| Morioka | chronic | 1339 G → A | 447 Gly → Arg | nonpolar to basic |

TABLE 6

| Variant | Nucleotide Change | Amino Acid Change | Result |
|---|---|---|---|
| Sassari | 514 G → C | Glu → Gln | acidic to slightly polar |
| Parma | not characterized | — | — |
|  | 1456 C → T | Arg → Trp | basic to nonpolar |
| Soresina | 1456 C → T | Arg → Trp | basic to nonpolar |
|  | 1552 C → A | Arg → Ser | baic to slightly polar |
| Milano | 1456 C → T | Arg → Trp | basic to nonpolar |
| Brescia | 1042-1044 del | Lys deleted | basic deleted |
|  | 1456 C → T | Arg → Trp | basic to nonpolar |
| Manatova | 1168 G → A | Asp → Asn | acidic to slightly polar |

We claim:

1. A method of identifying an operational reaction pathway of a biosystem, wherein the steps of said method are performed on a suitably programmed computer programmed to execute the steps comprising:
  (a) providing a set of systemic reaction pathways through a reaction network representing said biosystem;
  (b) providing a set of phenomenological reaction pathways of said biosystem;
  (c) comparing said set of systemic reaction pathways with said set of phenomenological reaction pathways; and
  (d) providing an output to a user of the selection of a pathway common to said set of systemic reaction pathways and said phenomenological reaction pathways of said biosystem, wherein said pathway common to said sets is an operational reaction pathway of said biosystem.

2. The method of claim 1, wherein said biosystem is a prokaryotic cell, or biological process thereof.

3. The method of claim 2, wherein said prokaryotic cell is selected from the group consisting of *E. coli*, *B. subtilis*, *H. influenzae* and *H. pylori*.

4. The method of claim 2, wherein said biological process is metabolism.

5. The method of claim 3, wherein said prokaryotic cell is *E. coli*.

6. The method of claim 3, wherein said prokaryotic cell is *B. subtilis*.

7. The method of claim 3, wherein said prokaryotic cell is *H. influenzae*.

8. The method of claim 3, wherein said prokaryotic cell is *H. pylori*.

9. The method of claim 1, wherein said biosystem is a eukaryotic cell, or biological process thereof.

10. The method of claim 9, wherein said eukaryotic cell is selected from the group consisting of *S. cerevisiae* and *H. sapiens*.

11. The method of claim 9, wherein said biological process is metabolism.

12. The method of claim 10, wherein said eukaryotic cell is *S. cerevisiae*.

13. The method of claim 10, wherein said eukaryotic cell is *H. sapiens*.

14. The method of claim 1, wherein step (a) comprises determining a set of extreme pathways of said reaction network.

15. The method of claim 1, wherein step (a) further comprises constructing an in silico model of said reaction network to produce said set of systemic reaction pathways.

16. The method of claim 15, wherein said constructing an in silico model comprises determining the sequence of a genome containing open reading frames.

17. The method of claim 16, wherein said constructing an in silico model comprises determining open reading frames of a sequence of a genome for identifying the function of said open reading frames.

18. The method of claim 17, wherein said constructing an in silico model comprises assigning biochemical functions to open reading frames of a genome, whereby a biochemical function of an open reading frame is included in said set of systemic reaction pathways of said in silico model.

19. The method of claim 1, wherein said set of phenomenological reaction pathways in step (b) is provided by a process comprising analyzing gene expression data to produce said set of phenomenological reaction pathways.

20. The method of claim 19, wherein said gene expression data is obtained by determining said gene expression.

21. The method of claim 1, wherein said set of phenomenological reaction pathways in step (b) is provided by a process comprising analyzing protein expression data to produce said set of phenomenological reaction pathways.

22. The method of claim 21, wherein said protein expression data is obtained by determining said protein expression.

23. The method of claim 1, wherein said set of phenomenological reaction pathways in step (b) is provided by a process comprising analyzing metabolite production data to produce said set of phenomenological reaction pathways.

24. The method of claim 23, wherein said metabolite production data is obtained by determining said metabolite production.

25. The method of claim 1, wherein said set of phenomenological reaction pathways in step (b) is provided by a process comprising analyzing reaction usage data to produce said set of phenomenological reaction pathways.

26. The method of claim 25, wherein said reaction usage data is obtained by determining said reaction usage.

27. The method of any of claims 19-26 wherein said data is analyzed using a method selected from the group consisting of clustering analysis, singular value decomposition, principal component analysis and multivariable time series analysis.

28. The method of claim 27, wherein said data is analyzed using singular value decomposition.

29. The method of claim 27, wherein said data is analyzed using clustering analysis.

30. The method of claim 27, wherein said data is analyzed using principal component analysis.

31. The method of claim 27, wherein said data is analyzed using multivariable time series analysis.

* * * * *